United States Patent
Griffith

(10) Patent No.: US 7,329,658 B2
(45) Date of Patent: Feb. 12, 2008

(54) CANNABINOID RECEPTOR LIGANDS AND USES THEREOF

(75) Inventor: David A. Griffith, Old Saybrook, CT (US)

(73) Assignee: Pfizer Inc, New York, NY (US)

( * ) Notice: Subject to any disclaimer, the term of this patent is extended or adjusted under 35 U.S.C. 154(b) by 92 days.

(21) Appl. No.: 10/763,105

(22) Filed: Jan. 21, 2004

(65) Prior Publication Data

US 2004/0157839 A1 Aug. 12, 2004

Related U.S. Application Data

(60) Provisional application No. 60/445,728, filed on Feb. 6, 2003.

(51) Int. Cl.
C07D 487/04 (2006.01)
A61K 31/53 (2006.01)
A61P 3/04 (2006.01)

(52) U.S. Cl. ............... 514/245; 544/194; 544/219; 544/112; 544/60; 514/234.5; 514/227.8

(58) Field of Classification Search ........... 544/194, 544/219; 514/245
See application file for complete search history.

(56) References Cited

U.S. PATENT DOCUMENTS

| | | |
|---|---|---|
| 3,865,824 A | 2/1975 | Kobe et al. |
| 3,910,907 A | 10/1975 | O'Brien et al. |
| 3,995,039 A | 11/1976 | Rooney et al. |
| 4,183,930 A | 1/1980 | Cohen |
| 4,734,414 A | 3/1988 | Kim |
| 4,767,858 A | 8/1988 | Kim |
| 4,824,834 A | 4/1989 | Fujii et al. |
| 4,925,846 A | 5/1990 | Deacon et al. |
| 4,944,790 A | 7/1990 | Moser et al. |
| 4,992,442 A | 2/1991 | Tsujitani et al. |
| 5,051,518 A | 9/1991 | Murray et al. |
| 5,055,479 A | 10/1991 | Takiguchi et al. |
| 5,086,057 A | 2/1992 | Sasagawa et al. |
| 5,134,142 A | 7/1992 | Matsuo et al. |
| 5,137,887 A | 8/1992 | Hashimoto et al. |
| 5,246,932 A | 9/1993 | Caulkett et al. |
| 5,270,311 A | 12/1993 | Caulkett et al. |
| 5,290,776 A | 3/1994 | Caulkett et al. |
| 5,356,894 A | 10/1994 | Rodney et al. |
| 5,380,714 A | 1/1995 | Jones et al. |
| 5,420,128 A | 5/1995 | Kiyokawa et al. |
| 5,462,960 A | 10/1995 | Barth et al. |
| 5,571,813 A | 11/1996 | Ruhter et al. |
| 5,596,106 A | 1/1997 | Cullinan et al. |
| 5,602,136 A | 2/1997 | Ruhter et al. |
| 5,602,137 A | 2/1997 | Ruhter et al. |
| 5,624,941 A | 4/1997 | Barth et al. |
| 5,744,491 A | 4/1998 | Boigegrain et al. |
| 5,744,493 A | 4/1998 | Boigegrain et al. |
| 5,747,524 A | 5/1998 | Cullinan et al. |
| 5,925,768 A | 7/1999 | Barth et al. |
| 6,028,084 A | 2/2000 | Barth et al. |
| 6,060,478 A | 5/2000 | Gilligan et al. |
| 6,100,259 A | 8/2000 | Xiang et al. |
| 6,124,289 A | 9/2000 | He et al. |
| 6,136,809 A | 10/2000 | Gilligan et al. |
| 6,191,131 B1 | 2/2001 | He et al. |
| 6,194,410 B1 | 2/2001 | Bos et al. |
| 6,313,124 B1 | 11/2001 | He et al. |
| 6,344,474 B1 | 2/2002 | Maruani et al. |
| 6,355,631 B1 | 3/2002 | Bouchard et al. |
| 6,358,950 B1 | 3/2002 | He et al. |
| 6,372,743 B1 | 4/2002 | Darrow et al. |
| 6,432,984 B1 | 8/2002 | Barth et al. |
| 6,476,038 B1 | 11/2002 | Darrow et al. |
| 6,476,060 B2 | 11/2002 | Lange et al. |
| 6,479,479 B2 | 11/2002 | Achard et al. |
| 6,509,338 B1 | 1/2003 | Olson et al. |

(Continued)

FOREIGN PATENT DOCUMENTS

CA 2387138 4/2001

(Continued)

OTHER PUBLICATIONS

Wolft Manfred E. "Burger's Medicinal Chemistry, 5ed, Part 1", John Wiley & Sons, 1995, pp. 975-977.*

(Continued)

Primary Examiner—Venkataraman Balasubram
(74) Attorney, Agent, or Firm—Gregg C. Benson; Arlene K. Musser

(57) ABSTRACT

Compounds of Formula (I) that act as cannabinoid receptor ligands and their uses in the treatment of diseases linked to the mediation of the cannabinoid receptors in animals are described herein.

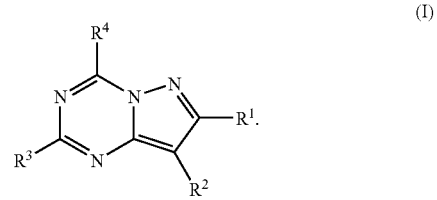

(I)

65 Claims, No Drawings

U.S. PATENT DOCUMENTS

| | | |
|---|---|---|
| 6,509,367 B1 | 1/2003 | Martin et al. |
| 6,518,264 B2 | 2/2003 | Achard et al. |
| 6,566,356 B2 | 5/2003 | Achard et al. |
| 6,642,258 B1 | 11/2003 | Bourrie et al. |
| 2001/0027193 A1 | 10/2001 | Achard et al. |
| 2001/0053788 A1 | 12/2001 | Lange et al. |
| 2002/0019383 A1 | 2/2002 | Achard et al. |
| 2002/0019421 A1 | 2/2002 | Biberman et al. |
| 2002/0035102 A1 | 3/2002 | Achard et al. |
| 2002/0091114 A1 | 7/2002 | Plot-Grosjean et al. |
| 2002/0119972 A1 | 8/2002 | Leftheris et al. |
| 2002/0128302 A1 | 9/2002 | Maruani et al. |
| 2002/0188007 A1 | 12/2002 | Barth et al. |
| 2003/0003145 A1 | 1/2003 | Abramovici et al. |
| 2003/0008885 A1 | 1/2003 | He et al. |
| 2003/0055033 A1 | 3/2003 | Achard et al. |
| 2003/0087933 A1 | 5/2003 | Blanchard et al. |
| 2003/0114495 A1 | 6/2003 | Finke et al. |
| 2003/0125330 A1 | 7/2003 | Gilligan |
| 2003/0139386 A1 | 7/2003 | Cote et al. |
| 2003/0199536 A1 | 10/2003 | Thomas et al. |
| 2004/0077650 A1 | 4/2004 | Dow |
| 2004/0092520 A1 | 5/2004 | Griffith |
| 2004/0122074 A1 | 6/2004 | Dow et al. .................. 514/397 |
| 2005/0124616 A1 | 6/2005 | Gudmundsson .......... 514/234.5 |

FOREIGN PATENT DOCUMENTS

| | | |
|---|---|---|
| EP | 293220 B1 | 8/1994 |
| EP | 269 859 B2 | 10/1995 |
| EP | 1354884 | 10/2003 |
| WO | WO 96/02248 A1 | 2/1996 |
| WO | WO 9803510 | 7/1997 |
| WO | WO 00/15609 A1 | 5/2000 |
| WO | WO 01/24798 A1 | 4/2001 |
| WO | WO 01/028557 A1 | 4/2001 |
| WO | WO 01/029007 A1 | 4/2001 |
| WO | WO 01/032629 A1 | 5/2001 |
| WO | WO 01/032663 A2 | 5/2001 |
| WO | WO 01/58450 A2 | 8/2001 |
| WO | WO 01/85092 A2 | 11/2001 |
| WO | WO 02072202 | 3/2002 |
| WO | WO 02053565 | 7/2002 |
| WO | WO 02/076949 A1 | 10/2002 |
| WO | WO 03/006007 A1 | 1/2003 |
| WO | WO 03/007887 A2 | 1/2003 |
| WO | WO 03076441 | 2/2003 |
| WO | WO 03/018060 A1 | 3/2003 |
| WO | WO 03/020217 A2 | 3/2003 |
| WO | WO 03/020314 A1 | 3/2003 |
| WO | WO 03/026647 A1 | 4/2003 |
| WO | WO 03/026648 A1 | 4/2003 |
| WO | WO 03/027069 A1 | 4/2003 |
| WO | WO 03/027076 A2 | 4/2003 |
| WO | WO 03/027114 A1 | 4/2003 |
| WO | WO 03/040107 A1 | 5/2003 |
| WO | WO 03/051850 A1 | 6/2003 |
| WO | WO 03/051851 A1 | 6/2003 |
| WO | WO 01/54695 A1 | 8/2003 |
| WO | WO 03/075660 A1 | 9/2003 |
| WO | WO 03/077847 A2 | 9/2003 |
| WO | WO 03/078413 A1 | 9/2003 |
| WO | WO 03076441 | 9/2003 |
| WO | WO 2004022054 | 9/2003 |
| WO | WO 03/082190 A2 | 10/2003 |
| WO | WO 03/082191 A2 | 10/2003 |
| WO | WO 03/082256 A2 | 10/2003 |
| WO | WO 03/082833 A1 | 10/2003 |
| WO | WO 03/084943 A2 | 10/2003 |
| WO | WO 03/086288 A2 | 10/2003 |
| WO | WO 03/087037 A1 | 10/2003 |
| WO | WO 03095455 | 11/2003 |
| WO | WO 04/012617 A2 | 2/2004 |

OTHER PUBLICATIONS

Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Petrocellis et al., British Journal of Pharmacology, 141, 765-774, 2004.*
Black, Curr. Opin . . Investig. Drugs 5(4): 389-394, 2004.*
Sato, Yasunobu, et al., "Studies on Cardiovascular Agents. 6. Synthesis and Coronary Vasodilating and Antihypertensive Activities of 1,2,4-Triazolo[1,5-a]pyrimidines Fused to Heterocyclic Systems," *J. Med. Chem*, 23, 927-937 (1980).
Senga, Keitaro, et al., "Synthesis and Antischistosomal Activity of Certain Pyrazolo[1,5-a]pyrimidines," *J. Med Chem*, 24, 610-613 (1981).
Senga, Keitaro, et al., "Synthesis and Enzymic Activity of Various Substituted Pyrazolo[1,5-a]-1,3,5-triazines as Adenosine Cyclic 3',5'-Phosphate Phosphodiesterase Inhibitors," *J Med Chem*, 25, 243-249 (1982).
He, Liqi, et al., "4-(1,3-Dimethoxyprop-2-ylamino)-2,7-dimethyl-8-(2,4-dichlorophenyl)-pyrazolo[1,5-a]-1,3,5-triazine: A Potent, Orally bioavailable CRF3 Receptor Antagonist," *J Med Chem*, 43, 449-456 (2000).
Almansa, Carmen, et al., "Synthesis and SAR of a New Series of COX-2 Selective Inhibitors: Pyrazolo[1,5-a]pyrimidines," *J Med Chem*, 44, 350-361 (2001).
C. Bellec et al., Can. J. Chem., 1981, vol. 59, pp. 2826-2832, "Deaminative Electrochemical Reduction of pyrazolo[1,5-a]pyrimidine-7-amines".
A. Takamizawa et al., Chem. Pharm. Bull., 1965, vol. 13, 10, pp. 1207-1220, "Syntheses of Pyrazole Derivatives. XI.[*1] Acetylation Products of 7-Aminopyrazolo[1,5-a]pryrimidines. Supplement".
Y. Sawaki et al., Bull. Chem. Soc. Jpn., 1981, vol. 54, pp. 793-799, "Mechanism of the Reaction of Nitriles with Alkaline Hydrogen Peroxide. Reactivity of Peroxycarboximidic Acid and Application to Superoxide Ion Reaction".
H. Beyer et al., 1960, pp. 2209-2216, Zur Umsetzung von Ketonitrilen mit Hydrazinderivaten der Kohlensäure.
J. Kobe et al., Dec. 1974, vol. 11, pp. 991-996, "The Chemistry of 4-Hydrazino-7-phenylpyrazolo{1,5-a]-1,3,5-triazines".
Tzavara, E.T., et al., "The CB1 Receptor Antagonist SR141716A selectively increases monoaminerigic neurotransmission in the medial prefrontal cortex: Implications cortex: Implications for Therapeutic Actions," *J Pharmacol*, 138, 544-553 (2003).
Racz, I., et al., "A Critical Role for the Cannabinoid CB1 Receptors in Alcohol Dependence and Stress-Stimulated Ethanol Drinking," *J Neurosci*, 23(6), 2453-2458 (2003).
Croci, T., et al., "Role of Cannabinoid CB1 Receptors and Tumor Necrosis Factor-α in the gut and systemic anti-inflammatory activity of SR 141716 (Rimonabant) in rodents," *Brit J Pharmacol*, 140, 115-122 (2003).
DaSilva, G.E., et al., "Potentiation of Penile Erection and Yawning Responses to Apomorphine by Cannabinoid Receptor Antagonists in Rats," *Neurosci Let*, 349, 49-52 (2003).
Wang, L., et al., "Endocannabinoid Signaling via Cannabinoid Receptor 1 is Involved in Ethanol Preference and its Age-Dependent Decline in Mice," *PNAS*, 100(3), 1393-1398 (2003).
Ruiu, S., et al., "Synthesis and Characterization of NESS 0327: A Novel Putative Antagonist of the CB1 Cannabinoid Receptor," *J Pharmacol Exp Therap*, 306, 363-370 (2003).
Howlett, A.C., et al., "International Union of Pharmacology. XXVII. Classification of Cannabinoid Receptors," *Pharmacol Rev*, 54, 161-202 (2002).
Gomez, R., et al., "A Peripheral Mechanism for CB1 Cannabinoid Receptor-Dependent Modulation of Feeding," *J. Neurosci*, 22(21), 9612-9617 (2002).

Wiley, J.L., et al., "Novel Pyrazole Cannabinoids: Insights into CB1 Receptor Recognition and Activation," *J Pharmacol Exp Therap*, 296(3), 1013-1022 (2001).

Lellemand, F., et al., "Effects of CB1 Cannabinoid Receptor Blockade on Ethanol Preference After Chronic Ethanol Administration," *Alcohol Clin Exp Res*, 25(9), 1317-1323 (2001).

Pertwee, R.G., "Cannabinoids and the Gastronintestinal Tract," *Gut*, 48, 859-867 (2001).

Pertwee, R.G., "Cannabinoid Receptor Ligands: Clinical and Neuropharmacological Considerations, Relevant to Future Drug Discovery and Development," *Exp. Opin. Invest. Drugs*, 9(7), 1573-1571 (2000).

Hungund, B.L and B.S. Basavarajappa, "Are Anadamide and Cannabinoid Receptors involved in Ethanol Tolerance? A Review of the Evidence," *Alcohol & Alcoholism*. 35(2) 126-133, (2000).

Freedland C.S., et al., "Effects of SR141716A, a Central Cannabinoid Receptor Antagonist, on Food-maintained Responding," *Pharmacol Biochem Behav*, 67, 265-270 (2000).

Lan, R., et al., "Structure-Activity Relationships of Pyrazole Derivatives as Cannabinoid Receptor Antagonists" *J. Med. Che.m*, 42, 769-776 (1999).

Pertwee, R.G., "Pharmacology of Cannabinoid Receptor Ligands" *Curr Med Chem*, 6, 635-664 (1999).

Basavarajappa, B.S., et al., "Chronic Ethanol Administration Downregulates Cannabinoid Receptors in Mouse Brain Synaptic Plasma Membrane," *Brian Res*, 793, 212-218 (1998).

Thomas, B.F., et al., "Comparative Receptor Binding Analyses of Cannabinoid Agonists and Antagonists," *J Pharmacol Exp Therap*, 285, 285-292 (1998).

Colombo, G., et al., "Appetite Suppression and Weight Loss after the Cannabinoid Antagonist SR141716," *Life Sci.*, 63, PL113-PL117 (1998).

Simiand, J., et al., "SR141716, a CB1 Cannabinoid Receptor Antagonist, Selectively Reduces Sweet Food Intake in Marmose," *Behav. Pharmacol.*, 9, 179-181 (1998).

Chaperon, F., et al., "Involvement of Central Cannabinoid (CB1) Receptors in the Establishment of Place Conditioning in Rats," *Psychopharmacology*, 135, 324-332 (1998).

Arnone, M., et al., "Selective Inhibition of Sucrose and Ethanol Intake by SR141716, an Antagonist of Central Cannabinoid (CB1) Receptors," *Psychopharmacol*, 132, 104-106 (1997).

Savontaus, E., et al., "Anti-Obesity Effect on MPV-1743 A III, a Novel Imidazoline Derivative, in Genetic Obesity," *Eur J Pharmacol*, 328, 207-215 (1997)

Sanudo-Pena, M.C., et al., "Endogenous Cannabinoids as an Aversive or Counter-rewarding System in the Rat," *Neurosci Let*, 223, 125-128 (1997).

Gifford, A.N., et al., "Electrically Evoked Acetylcholine Relase from Hippocampal Silices is inhibited by the Cannabinoid Receptor Agonist, WIN 55212-2 and is Potentiated by the Cannabinoid Antagonist, SR 141716A," *J Pharmacol Exp Ther*, 277, 1431-1436 (1996).

Compton, D.R., et al., "In Vivo Characterization of a Specific Cannabinoid Receptor Antagonist (SR141716A); Inhibition of Delta-9-Tetrahydrocannabinol-Induced Responses and Apparent Agonist Activity," *J Pharmacol Exp Ther*, 277, 586-594 (1996).

Mansbach, R.S., et al., "Effects of the Cannabinoid CB1 Receptor Antagonist SR141716A on the Behavior of Pigeons and Rats," *Psychopharmacology*, 124, 315-322 (1996).

Lichtman, A.H., et al., "Delta-9-Tetrahydrocannabinol Impairs Spatial Memory through a Cannabinoid Receptor Mechanism," *Psychopharmacology*, 126, 125-131 (1996).

Perio, A., et al., "Central Mediation of the Cannabinoid Cue: Activity of a Selective CB1 Antagonist, SR141716A," *Behavioral Pharmacology*, 7, 65-71 (1996).

Rinaldi-Carmona, M., et al., "Biochemical and Pharmacological Characteriszation of SR141716A, The First Potent and Selective Brain Cannabinoid Receptor Antagonist," *Life Sci*, 56, 1941-1947 (1995).

Pertwee, R., et al., "AM630, A Competititve Cannabinoid Receptor Antagonist," *Life Sci*, 56, 1949-1955 (1995).

Rinaldi-Carmona, M., et al., "SR141716A, a Patent and Selective Antagonist of the Brain Cannabinoid Receptor," *FEBS Letters*, 350, 240-244 (1994).

Dutta, A., et al., "The Synthesis and Pharmacological Evaluation of the Cannabinoid Antagonist SR 141716A", *Med. Chem. Rev.* 5, 54-62 (1994).

Drummond, J., et al., "Evaluation and Synthesis of Aminohydroxyisoxazoles and Pyrazoles as Potential Glycine Agonists," *J. Med. Chem*, 32, 2116-2128 (1989).

Murray, W., et al., "A Simple Regioselective Synthesis of Ethyl 1,5-Diarylpyrazole-3-carboxylates" *J. Heterocyclic Chem*, 26, 1389 (1989).

Dewey, W.L. "Cannabinoid Pharmacology," *Pharmacological Reviews*, 38(2)m 151-178 (1986).

Tewari, R.S., et al., "1,3-Dipolar Cycloaddition and Nucleophylic Substitution Reactions of C-Acetyl and C-Ethoxycarbonyl Derivative of Hydrazidoyl Bromides" *Tetrahedron*, 39(1) 129-136 (1983).

Birkofer, L. and K. Richtzenhain, "Silyl-Derivate von Pyrazol, Isoxazol und 1,2,3-Triazol" *Chem. Ber*. 112, 2829-2836 (1979).

Franke, H. et al., "Polare Cycloadditionen von elektronenreichen Mehrfach-bindungssystemen an 1,3,4-oxadiazolium-Salze: Synthese von 3aH-[1,3,4]Oxadiazolo[3,2-a]chinolinen" *Chem. Ber*. 112, 3623-3636 (1979).

Sucrow, W., et al., "Bimolekulare Cyclisierung von 2-(1-Methylhydrazino)maleinsaure-dimethylester" *Chem. Ber*. 112, 1712-1718 (1979).

* cited by examiner

CANNABINOID RECEPTOR LIGANDS AND USES THEREOF

FIELD OF THE INVENTION

The present invention relates to substituted pyrazolo[1,5-a][1,3,5]triazine compounds as cannabinoid receptor ligands, in particular CB1 receptor antagonists, and uses thereof for treating diseases, conditions and/or disorders modulated by cannabinoid receptor antagonists.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207-12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," *Obes Res.,* 3(suppl 4), 415s-7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., "Selective Inhibition of Sucrose and Ethanol Intake by SR141716, an Antagonist of Central Cannabinoid (CB1) Receptors," *Psychopharmacol,* 132, 104-106 (1997); Colombo, G., et al., "Appetite Suppression and Weight Loss after the Cannabinoid Antagonist SR141716," *Life Sci.,* 63, PL113-PL117 (1998); Simiand, J., et al., "SR141716, a CB1 Cannabinoid Receptor Antagonist, Selectively Reduces Sweet Food Intake in Marmose," *Behav. Pharmacol.,* 9, 179-181 (1998); and Chaperon, F., et al., "Involvement of Central Cannabinoid (CB1) Receptors in the Establishment of Place Conditioning in Rats," *Psychopharmacology,* 135, 324-332 (1998). For a review of cannabinoid CB1 and CB2 receptor modulators, see Pertwee, R. G., "Cannabinoid Receptor Ligands: Clinical and Neuropharmacological Considerations, Relevant to Future Drug Discovery and Development," *Exp. Opin. Invest. Drugs,* 9(7), 1553-1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., "Selective Inhibition of Sucrose and Ethanol Intake by SR141716, an Antagonist of Central Cannabinoid (CB1) Receptors," *Psychopharmacol,* 132, 104-106 (1997). For a review, see Hungund, B. L. and B. S. Basavarajappa, "Are Anadamide and Cannabinoid Receptors involved in Ethanol Tolerance? A Review of the Evidence," *Alcohol & Alcoholism.* 35(2) 126-133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I) that act as cannabinoid receptor ligands (in particular, CB1 receptor antagonists)

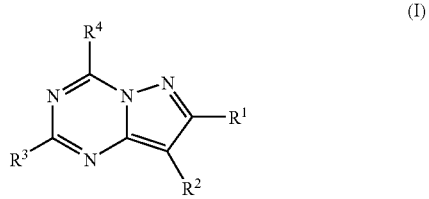

wherein $R^1$ is an optionally substituted aryl or an optionally substituted heteroaryl (preferably, $R^1$ is a substituted phenyl, more preferably a phenyl substituted with one to three substituents independently selected from the group consisting of halo (preferably, chloro or fluoro), $(C_1-C_4)$alkoxy, $(C_1-C_4)$alkyl, halo-substituted $(C_1-C_4)$alkyl (preferably fluoro-substituted alkyl), and cyano, most preferably, $R^1$ is 2-chlorophenyl, 2-fluorophenyl, 2,4-dichlorophenyl, 2-fluoro-4-chlorophenyl, 2-chloro-4-fluorophenyl, or 2,4-difluorophenyl);

$R^2$ is an optionally substituted aryl or an optionally substituted heteroaryl (preferably, $R^2$ is a substituted phenyl, more preferably a phenyl substituted with one to three substituents independently selected from the group consisting of halo (preferably, chloro or fluoro), $(C_1-C_4)$alkoxy, $(C_1-C_4)$alkyl, halo-substituted $(C_1-C_4)$alkyl (preferably fluoro-substituted alkyl), and cyano, most preferably, $R^2$ is 4-chlorophenyl or 4-fluorophenyl);

$R^3$ is hydrogen, $(C_1-C_4)$alkyl, halo-substituted $(C_1-C_4)$alkyl, or $(C_1-C_4)$alkoxy;

$R^4$ is (i) a group having Formula (IA) or Formula (IB)

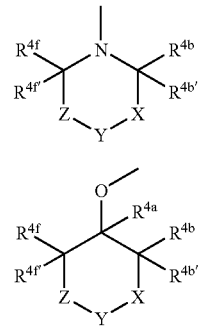

where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl $(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —$C(R^{4d})(R^{4d'})$—, where $R^{4d}$ and $R^{4d'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated heterocyclic ring, a 5-6 membered lactone ring, or a 4-6 membered lactam ring, where said heterocyclic ring, said lactone ring and said lactam ring are optionally substituted with one or more substituents and said lactone ring and said lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

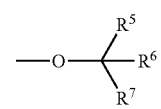

where $R^5$ and $R^6$ are each independently hydrogen or $(C_1-C_4)$alkyl, and $R^7$ is an optionally substituted $(C_1-C_4)$alkyl-, or an optionally substituted 4-6 membered partially or fully saturated heterocyclic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents; or (iii) an amino group having attached thereto at least one chemical moiety selected from the group consisting of $(C_1-C_8)$alkyl, aryl$(C_1-C_4)$alkyl, a partially or fully saturated $(C_3-C_8)$cycloalkyl, hydroxy$(C_1-C_6)$alkyl, $(C_1-C_3)$alkoxy $(C_1-C_6)$alkyl, heteroaryl$(C_1-C_3)$alkyl, aryl, heteroaryl, and a fully or partially saturated heterocycle, where said moiety is optionally substituted with one or more substituents and provided that $R^4$ is not n-butylamine or diethylamine when $R^1$ is phenyl, o-tolyl, or p-methoxyphenyl, and $R^2$ is phenyl or m-tolyl;

a pharmaceutically acceptable salt thereof, a prodrug of the compound or the salt, or a solvate or hydrate of the compound, the salt or the prodrug.

In another embodiment of the present invention, a compound of Formula (II) is provided.

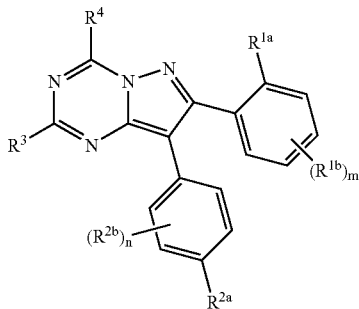
(II)

wherein $R^{1a}$, $R^{1b}$, $R^{2a}$, and $R^{2b}$ are each independently halo, $(C_1-C_4)$alkoxy, $(C_1-C_4)$alkyl, halo-substituted $(C_1-C_4)$alkyl, or cyano;

n and m are each independently 0, 1 or 2;

$R^3$ is hydrogen, $(C_1-C_4)$alkyl, halo-substituted $(C_1-C_4)$ alkyl, or $(C_1-C_4)$alkoxy; and $R^4$ is (i) a group having Formula (IA) or Formula (IB)

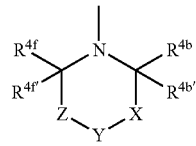
IA

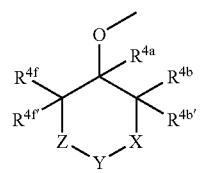
IB where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$ alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$ alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —$C(R^{4d})(R^{4d'})$, where $R^{4d}$ and $R^{4d'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$ alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where the carbocyclic ring, the heterocyclic ring, the lactone ring and the lactam ring are optionally substituted with one or more substituents and the lactone ring and the lactam ring optionally contain an additional heteroatom selected from oxygen, nitrogen or sulfur, or Y is —$NR^{4d''}$, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$ alkyl-O—C(O)—, aryl, and heteroaryl, where said moiety is optionally substituted with one or more substituents;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl)$_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$ alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

(ii) a group having Formula (IC)

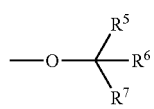

IC where $R^5$ and $R^6$ are each independently hydrogen or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $(C_1-C_4)$alkylamino$(C_1-C_4)$alkyl-, di$(C_1-C_4)$alkylamino$(C_1-C_4)$alkyl-, or a 4-6 membered partially or fully saturated heterocylic ring containing 1 to 2 heteroatoms independently selected from oxygen, sulfur or nitrogen, or $R^5$ and $R^6$ or $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where said lactone, said lactam and said heterocycle are optionally substituted with one or more substituents;

(iii) an amino group having attached thereto at least one chemical moiety selected from the group consisting of $(C_1-C_8)$alkyl, aryl$(C_1-C_4)$alkyl, a partially or fully saturated $(C_3-C_8)$cycloalkyl, hydroxy$(C_1-C_6)$alkyl, $(C_1-C_3)$alkoxy $(C_1-C_6)$alkyl, heteroaryl$(C_1-C_3)$alkyl, aryl, heteroaryl, and a fully or partially saturated heterocycle, where the moiety is optionally substituted with one or more substituents; or (iv) an $(C_1-C_6)$alkyl or $(C_1-C_6)$alkenyl group having attached thereto at least one chemical moiety selected from the group consisting of hydroxy, $(C_1-C_6)$alkoxy, amino, $(C_1-C_6)$alkylamino, di$((C_1-C_6)$alkyl)amino $(C_1-C_3)$alkylsulfonyl, $(C_1-C_3)$alkylsulfamyl, di$((C_1-C_3)$alkyl)sulfamyl, acyloxy, a partially or fully saturated heterocycle, and a partially or fully saturated carbocyclic ring, where said chemical moiety is optionally substituted with one or more substituents;

a pharmaceutically acceptable salt thereof, a prodrug of the compound or the salt, or a solvate or hydrate of the compound, the salt or the prodrug.

A preferred compound of the present invention is a compound of Formula (I) or Formula (II) where $R^4$ is a group of Formula (IA). Preferably, $R^{4b}$ and $R^{4b'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl$)_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a partially or fully saturated carbocyclic ring, where the moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl$)_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —$C(R^{4d})(R^{4d'})$—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl$)_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where the carbocyclic ring, the heterocyclic ring, the lactone ring and the lactam ring are optionally substituted with one or more substituents and the lactone ring and the lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$ alkyl-O—C(O)—, aryl, and heteroaryl, where the moiety is optionally substituted with one or more substituents;

Z is a bond, —$CH_2CH_2$—, or —$C(R^{4e})(R^{4e'})$—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Preferably, $R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge; $R^{4b'}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge; $R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge, and even more preferably, $R^{4b}$, $R^{4b'}$, $R^{4f}$, and $R^{4f'}$ are all hydrogen.

When Y is —$NR^{4d''}$—, then $R^{4d''}$ is preferably a hydrogen or a chemical moiety selected from the group consisting of $(C_1-C_6)$alkyl, $(C_3-C_6)$cycloalkyl, $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, aryl, and heteroaryl, where the moiety is optionally substituted with one or more substituents (more preferably, $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, and heteroaryl, where the moiety is optionally substituted with one or more substituents (preferably the $(C_1-C_3)$alkylsulfonyl, $(C_1-C_3)$alkylaminosulfonyl, di$(C_1-C_3)$alkylaminosulfonyl, acyl, and $(C_1-C_6)$alkyl-O—C(O)— are optionally substituted with 1-3 fluorines, and the heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl);

X is —$C(R^{4c})(R^{4c'})$—, where $R^{4c}$ and $R^{4c'}$ are each independently hydrogen, $H_2NC(O)$—, or a chemical moiety selected from $(C_1-C_6)$alkyl, $(C_1-C_4)$alkyl-NH—C(O)—, or $((C_1-C_4)$alkyl)$_2$N—C(O)—, where the moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge; and Z is —$C(R^{4e})(R^{4e'})$—, where $R^{4e}$ and $R^{4e'}$ are each independently hydrogen, $H_2NC(O)$—, or a chemical moiety selected from $(C_1-C_6)$alkyl, $(C_1-C_4)$alkyl-NH—C(O)—, or $((C_1-C_4)$alkyl)$_2$N—C(O)—, where the moiety is optionally substituted with one or more substituents, or either $R^{4e}$ or $R^{4'}$ taken together with $R^{4b}$, $R^{4b'}$, $R^{4c}$, or $R^{4c'}$ forms a bond, a methylene bridge or an ethylene bridge.

Preferred compounds include: 7-(2-chlorophenyl)-8-(4-chlorophenyl)-2-methyl-4-(4-methyl piperazin-1-yl)-pyrazolo[1,5-a][1,3,5]triazine; 7-(2-chlorophenyl)-8-(4-chlorophenyl)-2-methyl-4-(4-pyrimidin-2-ylpiperazin-1-yl) pyrazolo[1,5-a][1,3,5]triazine; 7-(2-chlorophenyl)-8-(4-chlorophenyl)-4-[(1S,4S)-5-methanesulfonyl-2,5-diazabicyclo[2.2.1]hept-2-yl]-2-methylpyrazolo[1,5-a][1,3,5]triazine; 7-(2-chlorophenyl)-8-(4-chlorophenyl)-2-methyl-4-[4-(propane-2-sulfonyl)-piperazin-1-yl]-pyrazolo[1,5-a][1,3,5]triazine; 7-(2-chlorophenyl)-8-(4-chlorophenyl)-2-methyl-4-(4-ethanesulfonyl)-piperazin-1-yl)-pyrazolo[1,5-a][1,3,5]triazine; 7-(2-chlorophenyl)-8-(4-chlorophenyl)-2-methyl-4-piperazin-1-yl-pyrazolo[1,5-a][1,3,5]triazine; 7-(2-chlorophenyl)-8-(4-chlorophenyl)-2-methyl-4-(4-methanesulfonyl)-piperazin-1-yl)-pyrazolo[1,5-a][1,3,5]triazine; (1S,4S)-5-[7-(2-chlorophenyl)-8-(4-chlorophenyl)-2-methylpyrazolo[1,5-a][1,3,5]triazin-4-yl]-2,5-diazabicyclo[2.2.1]heptane-2-carboxylic acid tert-butyl ester; 7-(2-chlorophenyl)-8-(4-chlorophenyl)-4-[(1S,4S)-2,5-diazabicyclo[2.2.1]hept-2-yl]-2-methylpyrazolo[1,5-a][1,3,5]triazine; 1-{(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]hept-2-yl}-ethanone; 1-{(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]hept-2-yl}-2-methylpropan-1-one; 1-{(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]hept-2-yl}-phenylmethanone; 7-(2-chlorophenyl)-8-(4-chlorophenyl)-4-[(1S,4S)-5-ethanesulfonyl-2,5-diazabicyclo[2.2.1]hept-2-yl]-2-methylpyrazolo[1,5-a][1,3,5]triazine; 7-(2-chlorophenyl)-8-(4-chlorophenyl)-2-methyl-4-[(1S,4S)-5-(propane-2-sulfonyl)-2,5-diazabicyclo[2.2.1]hept-2-yl]-pyrazolo[1,5-a][1,3,5] triazine; and (1S,4S)-5-[7-(2-chlorophenyl)-8-(4-chlorophenyl)-2-methylpyrazolo[1,5-a][1,3,5]triazin-4-yl]-2,5-diazabicyclo[2.2.1]heptane-2-sulfonic acid dimethylamide; a pharmaceutically acceptable salt thereof, or a solvate or hydrate of said compound or said salt.

When Y is —$C(R^{4d})(R^{4d'})$—, then $R^{4d}$ is preferably hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where the moiety is optionally substituted with one or more substituents (preferably, $R^{4d}$ is amino, $(C_1-C_6)$alkylamino, di$(C_1-C_4)$alkylamino, $(C_3-C_6)$cycloalkylamino, acylamino, aryl$(C_1-C_4)$alkylamino-, or heteroaryl$(C_1-C_4)$alkylamino, more preferably, $R^{4d}$ is amino, $(C_1-C_6)$alkylamino, di$(C_1-C_4)$alkylamino, $(C_3-C_6)$cycloalkylamino), and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents (preferably, $R^{4d'}$ is $(C_1-C_6)$alkyl, $H_2NC(O)$—, $(C_1-C_4)$alkyl-NH—C(O)—, or $((C_1-C_4)$alkyl)$_2$N—C(O)—, or aryl, more preferably, $R^{4d'}$ is $H_2NC(O)$—, $(C_1-C_4)$alkyl-NH—C(O)—, or $((C_1-C_4)$alkyl)$_2$N—C(O)—), or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where the carbocyclic ring, the heterocyclic ring, the lactone ring and the lactam ring are optionally substituted with one or more substituents and the lactone ring and the lactam ring optionally contain an additional heteroatom selected from oxygen, nitrogen or sulfur;

X is a bond or —$C(R^{4c})(R^{4c'})$—, where $R^{4c}$ and $R^{4c'}$ are each hydrogen; and Z is a bond or —$C(R^{4e})(R^{4e'})$—, where $R^{4e}$ and $R^{4e'}$ are each hydrogen.

Preferred compounds include: 1-[7-(2-chlorophenyl)-8-(2,4-dichlorophenyl)-2-methylpyrazolo[1,5-a][1,3,5]triazin-4-yl]-3-ethylaminoazetidine-3-carboxylic acid amide; 1-[7,8-bis-(2-chlorophenyl)-2-methylpyrazolo[1,5-a][1,3,5]triazin-4-yl]-3-ethylaminoazetidine-3-carboxylic acid amide; 1-[7-(2-chlorophenyl)-8-(4-cyanophenyl)-2-methylpyrazolo[1,5-a][1,3,5]triazin-4-yl]-3-ethylaminoazetidine-3-carboxylic acid amide; 1-[7-(2-chlorophenyl)-8-(4-methylphenyl)-2-methylpyrazolo[1,5-a][1,3,5]triazin-4-yl]-3-ethylaminoazetidine-3-carboxylic acid amide; 1-[7-(2-chlorophenyl)-8-(4-ethylphenyl)-2-methylpyrazolo[1,5-a][1,3,5]triazin-4-yl]-3-ethylaminoazetidine-3-carboxylic acid amide; 1-[7-(2-chlorophenyl)-8-(4-methoxyphenyl)-2-methylpyrazolo[1,5-a][1,3,5]triazin-4-yl]-3-ethylaminoazetidine-3-carboxylic acid amide; 1-[7-(2-chlorophenyl)-8-(3-chlorophenyl)-2-methylpyrazolo[1,5-a][1,3,5]triazin-4-yl]-3-ethylaminoazetidine-3-carboxylic acid amide; 1-[7-(2-chlorophenyl)-8-(4-chlorophenyl)-2-methylpyrazolo[1,5-a][1,3,5]triazin-4-yl]-4-methylaminopiperidine-4-carboxylic acid amide; 1-[7-(2-chlorophenyl)-8-(4-fluorophenyl)-2-methylpyrazolo[1,5-a][1,3,5]triazin-4-yl]-4-ethylaminopiperidine-4-carboxylic acid amide; 1-[7-(2-chlorophenyl)-8-(4-chlorophenyl)-2-methylpyrazolo[1,5-a][1,3,5]triazin-4-yl]-4-ethylaminopiperidine-4-carboxylic acid amide; 1-[7-(2-chlorophenyl)-8-(4-chlorophenyl)-2-methylpyrazolo[1,5-a][1,3,5]triazin-4-yl]-4-isopropylaminopiperidine-4-carboxylic acid amide; 1-[7-(2-chlorophenyl)-8-(4-chlorophenyl)-2-methylpyrazolo[1,5-a][1,3,5]triazin-4-yl]-3-ethylaminoazetidine-3-carboxylic acid amide; 1-[7-(2-chlorophenyl)-8-(4-chlorophenyl)-2-methylpyrazolo[1,5-a][1,3,5]triazin-4-yl]-3-isopropylaminoazetidine-3-carboxylic acid amide; 3-amino-1-[7-(2-chlorophenyl)-8-(4-chlorophenyl)-2-methylpyrazolo[1,5-a][1,3,5]triazin-4-yl]-azetidine-3-carboxylic acid amide; 1-[7-(2-chlorophenyl)-8-(4-chlorophenyl)-2-methylpyrazolo[1,5-a][1,3,5]triazin-4-yl]-3-methylaminoazetidine-3-carboxylic acid amide; 1-[7-(2-chlorophenyl)-8-(4-chlorophenyl)-2-methylpyrazolo[1,5-a][1,3,5]triazin-4-yl]-3-dimethylaminoazetidine-3-carboxylic acid amide; 1-[7-(2-chlorophenyl)-8-(4-chlorophenyl)pyrazolo[1,5-a][1,3,5]triazin-4-yl]-3-isopropylaminoazetidine-3-carboxylic acid amide; 1-[7-(2-chlorophenyl)-8-(4-chlorophenyl)-pyrazolo[1,5-a][1,3,5]triazin-4-yl]-4-ethylaminopiperidine-4-carboxylic acid amide; 1-[7-(2-chlorophenyl)-8-(4-chlorophenyl)-pyrazolo[1,5-a][1,3,5]triazin-4-yl]-3-ethylaminoazetidine-3-carboxylic acid amide; and 1-[7-(2-chlorophenyl)-8-(4-chlorophenyl)pyrazolo[1,5-a][1,3,5]triazin-4-yl]-3-methylaminoazetidine-3-carboxylic acid amide; a pharmaceutically acceptable salt thereof or a solvate or hydrate of said compound or said salt.

More preferred compounds include: 1-[7-(2-chlorophenyl)-8-(4-chlorophenyl)-2-methylpyrazolo[1,5-a][1,3,5]triazin-4-yl]-4-ethylaminopiperidine-4-carboxylic acid amide; 1-[7-(2-chlorophenyl)-8-(4-chlorophenyl)-2-methylpyrazolo[1,5-a][1,3,5]triazin-4-yl]-3-ethylaminoazetidine-3-carboxylic acid amide; 1-[7-(2-chlorophenyl)-8-(4-chlorophenyl)-2-methylpyrazolo[1,5-a][1,3,5]triazin-4-yl]-3-isopropylaminoazetidine-3-carboxylic acid amide; 3-amino-1-[7-(2-chlorophenyl)-8-(4-chlorophenyl)-2-methylpyrazolo[1,5-a][1,3,5]triazin-4-yl]-azetidine-3-carboxylic acid amide; 1-[7-(2-chlorophenyl)-8-(4-chlorophenyl)-2-methylpyrazolo[1,5-a][1,3,5]triazin-4-yl]-3-methylaminoazetidine-3-carboxylic acid amide; 1-[7-(2-chlorophenyl)-8-(4-chlorophenyl)pyrazolo[1,5-a][1,3,5]triazin-4-yl]-3-isopropylaminoazetidine-3-carboxylic acid amide; 1-[7-(2-chlorophenyl)-8-(4-chlorophenyl)-pyrazolo[1,5-a][1,3,5]triazin-4-yl]-4-ethylaminopiperidine-4-carboxylic acid amide; and 1-[7-(2-chlorophenyl)-8-(4-chlorophenyl)-pyrazolo[1,5-a][1,3,5]triazin-4-yl]-3-ethylaminoazetidine-3-carboxylic acid amide; a pharmaceutically acceptable salt thereof or a solvate or hydrate of said compound or said salt.

Even more preferred 1-[7-(2-chlorophenyl)-8-(4-chlorophenyl)-2-methylpyrazolo[1,5-a][1,3,5]triazin-4-yl]-3-ethylaminoazetidine-3-carboxylic acid amide; a pharmaceutically acceptable salt thereof or a solvate or hydrate of said compound or said salt. In particular, the hydrochloride, methanesulfonate or benzenesulfonate salt, or a solvate or hydrate of the salt In another preferred embodiment of a compound where Y is —$C(R^{4d})(R^{4d'})$—, $R^{4b}$, $R^{4b'}$, $R^{4f}$, and $R^{4f'}$ are all hydrogen; $R^{4d}$ is hydrogen, hydroxy, amino, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_6)$alkylamino-, and di$(C_1$-$C_4)$alkylamino-, where the moiety is optionally substituted with one or more substituents (preferably, $R^{4d}$ is hydrogen, hydroxy, amino, or a chemical moiety selected from the group consisting of $(C_1$-$C_6)$alkoxy, acyl, $(C_1$-$C_6)$alkylamino-, and di$(C_1$-$C_4)$alkylamino-); and $R^{4d'}$ is hydrogen, or a chemical moiety selected from the group consisting of $(C_1$-$C_6)$alkyl, aryl and heteroaryl, where the moiety is optionally substituted with one or more substituents (preferably, $R^{4d'}$ is hydrogen, or a chemical moiety selected from the group consisting of $(C_1$-$C_6)$alkyl and aryl, where the moiety is optionally substituted with one or more substituents). In this embodiment, X is preferably —$C(R^{4c})(R^{4c'})$—, where $R^{4c}$ and $R^{4c'}$ are each independently hydrogen or an optionally substituted $(C_1$-$C_6)$alkyl, or either $R^{4c}$ or $R^{4c'}$ taken together with $R^{4e}$ or $R^{4e'}$ forms a bond, a methylene bridge or an ethylene bridge (preferably, $R^{4c}$ and $R^{4c'}$ are each hydrogen or either $R^{4c}$ or $R^{4c'}$ taken together with $R^{4e}$ or $R^{4e'}$ forms a bond); and Z is preferably —$C(R^{4e})(R^{4e'})$—, where $R^{4e}$ and $R^{4e'}$ are each independently hydrogen or an optionally substituted $(C_1$-$C_6)$alkyl, or either $R^{4e}$ or $R^{4e'}$ taken together with $R^{4c}$ or $R^{4c'}$ forms a bond, a methylene bridge or an ethylene bridge (preferably, $R^{4e}$ and $R^{4e'}$ are each hydrogen or either $R^{4e}$ or $R^{4e'}$ taken together with $R^{4c}$ or $R^{4c'}$ forms a bond).

Preferred compounds include: 1-{1-[7-(2-chlorophenyl)-8-(4-chlorophenyl)-2-methylpyrazolo[1,5-a][1,3,5]triazin-4-yl]-4-phenylpiperidin-4-yl}-ethanone; 3-[7-(2-chlorophenyl)-8-(4-chlorophenyl)-2-methylpyrazolo[1,5-a][1,3,5]triazin-4-yl]-3-azabicyclo[3.1.0]hex-6-ylamine; 1-[7-(2-chlorophenyl)-8-(4-chlorophenyl)-2-methylpyrazolo[1,5-a][1,3,5]triazin-4-yl]-4-(4-fluorophenyl)-piperidin-4-ol; and 4-benzyl-1-[7-(2-chlorophenyl)-8-(4-chlorophenyl)-2-methylpyrazolo[1,5-a][1,3,5]triazin-4-yl]-piperidin-4-ol; a pharmaceutically acceptable salt thereof, or a solvate or hydrate of said compound or said salt.

In yet another preferred embodiment of a compound of Formula (I) or (II) where Y is —$C(R^{4d})(R^{4d'})$—, $R^{4b}$, $R^{4b'}$, $R^{4f}$, and $R^{4f'}$ are all hydrogen; and $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where the carbocyclic ring, the heterocyclic ring, the lactone ring and the lactam ring are optionally substituted with one or more substituents and the lactone ring or the lactam ring optionally contains an additional heteroatom selected from oxygen, nitrogen or sulfur (preferably, $R^{4d}$ and $R^{4d'}$ taken together form a 5-6 membered lactam ring, where the lactam ring is optionally substituted with one or more substituents and optionally contains an additional heteroatom selected from nitrogen or oxygen). In this embodiment, X is preferably a bond, —CH$_2$CH$_2$— or —C($R^{4c}$)($R^{4c'}$)—, where $R^{4c}$ and $R^{4c'}$ are each independently hydrogen or an optionally substituted (C$_1$-C$_6$)alkyl, or either $R^{4c}$ or $R^{4c'}$ taken together with $R^{4e}$ or $R^{4e'}$ forms a bond, a methylene bridge or an ethylene bridge (more preferably, X is a bond or —C($R^{4c}$)($R^{4c'}$)—, where $R^{4c}$ and $R^{4c'}$ are each hydrogen); and Z is preferably a bond, —CH$_2$CH$_2$— or —C($R^{4e}$)($R^{4e'}$)—, where $R^{4e}$ and $R^{4e'}$ are each independently hydrogen or an optionally substituted (C$_1$-C$_6$)alkyl, or either $R^{4e}$ or $R^{4e'}$ taken together with $R^{4c}$ or $R^{4c'}$ forms a bond, a methylene bridge or an ethylene bridge (more preferably, Z is a bond or —C($R^{4e}$)($R^{4e'}$)—, where $R^{4e}$ and $R^{4e'}$ are each hydrogen).

Preferred compounds include: 2-[7-(2-chlorophenyl)-8-(4-chlorophenyl)-2-methylpyrazolo[1,5-a][1,3,5]triazin-4-yl]-5-methyl-2,5,7-triazaspiro[3.4]octan-8-one; 2-[7-(2-chlorophenyl)-8-(4-chlorophenyl)-2-methylpyrazolo[1,5-a][1,3,5]triazin-4-yl]-2,5,7-triazaspiro[3.4]octan-8-one; 8-[7-(2-chlorophenyl)-8-(4-chlorophenyl)-2-methylpyrazolo[1,5-a][1,3,5]triazin-4-yl]-1-isopropyl-1,3,8-triazaspiro[4.5]decan-4-one; and 2-[7-(2-chlorophenyl)-8-(4-chlorophenyl)-2-methylpyrazolo[1,5-a][1,3,5]triazin-4-yl]-6,6-dimethyl-2,5,7-triazaspiro[3.4]octan-8-one; a pharmaceutically acceptable salt thereof or a solvate or hydrate of said compound or said salt.

More preferred is 8-[7-(2-chlorophenyl)-8-(4-chlorophenyl)-2-methylpyrazolo[1,5-a][1,3,5]triazin-4-yl]-1-isopropyl-1,3,8-triazaspiro[4.5]decan-4-one; a pharmaceutically acceptable salt thereof or a solvate or hydrate of said compound or said salt.

Another preferred compound of the present invention is a compound of Formula (I) or (II) where $R^4$ is a group of Formula (IB) where where $R^{4a}$ is as defined above, $R^{4b}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a 3-6 membered partially or fully saturated carbocyclic ring, where the moiety is optionally substituted with one or more substituents, $R^{4b'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C($R^{4c}$)($R^{4c'}$)—, where $R^{4c}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a 3-6 membered partially or fully saturated carbocyclic ring, where the moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge (preferably, X is a bond, —CH$_2$CH$_2$— or —C($R^{4c}$)($R^{4c'}$)—, where $R^{4c}$ and $R^{4c'}$ are each independently hydrogen or (C$_1$-C$_6$)alkyl);

Y is oxygen, sulfur, —C(O)—, or —C($R^{4d}$)($R^{4d'}$)—, where $R^{4d}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, (C$_3$-C$_6$)cycloalkylamino-, acylamino-, aryl(C$_1$-C$_4$)alkylamino-, heteroaryl(C$_1$-C$_4$)alkylamino-, aryl, heteroaryl, a 3-6 membered partially or fully saturated heterocycle, and a 3-6 membered partially or fully saturated carbocyclic ring, where the moiety is optionally substituted with one or more substituents, and $R^{4d'}$ is hydrogen, H$_2$NC(O)—, or a chemical moiety selected from the group consisting of (C$_1$-C$_6$)alkyl, acyl, (C$_1$-C$_3$)alkyl-O—C(O)—, (C$_1$-C$_4$)alkyl-NH—C(O)—, (C$_1$-C$_4$)alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where the carbocyclic ring, the heterocyclic ring, the lactone ring and the lactam ring are optionally substituted with one or more substituents and the lactone ring and the lactam ring optionally contain an additional heteroatom selected from oxygen, nitrogen or sulfur, or Y is —NR$^{4d''}$—, where R$^{4d''}$ is a hydrogen or a chemical moiety selected from the group consisting of (C$_1$-C$_6$)alkyl, (C$_3$-C$_6$)cycloalkyl, (C$_1$-C$_3$)alkylsulfonyl-, (C$_1$-C$_3$)alkylaminosulfonyl-, di(C$_1$-C$_3$)alkylaminosulfonyl-, acyl, (C$_1$-C$_6$)alkyl-O—C(O)—, aryl, and heteroaryl, where the moiety is optionally substituted with one or more substituents (preferably, Y is —NR$^{4d''}$—, where R$^{4d''}$ is a hydrogen or a chemical moiety selected from the group consisting of (C$_1$-C$_6$)alkyl, (C$_3$-C$_6$)cycloalkyl, (C$_1$-C$_3$)alkylsulfonyl-, (C$_1$-C$_3$)alkylaminosulfonyl-, di(C$_1$-C$_3$)alkylaminosulfonyl-, acyl, (C$_1$-C$_6$)alkyl-O—C(O)—, aryl, and heteroaryl, where the moiety is optionally substituted with one or more substituents);

Z is a bond, —CH$_2$CH$_2$—, or —C($R^{4e}$)($R^{4e'}$)—, where $R^{4e}$ is hydrogen, cyano, hydroxy, amino, H$_2$NC(O)—, or a chemical moiety selected from the group consisting of (C$_1$-C$_6$)alkyl, (C$_1$-C$_6$)alkoxy, acyloxy, acyl, (C$_1$-C$_3$)alkyl-O—C(O)—, (C$_1$-C$_4$)alkyl-NH—C(O)—, (C$_1$-C$_4$)alkyl)$_2$N—C(O)—, (C$_1$-C$_6$)alkylamino-, ((C$_1$-C$_4$)alkyl)$_2$amino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where the moiety is optionally substituted with one or more substituents, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of ($C_1$-$C_6$)alkyl, acyl, ($C_1$-$C_3$)alkyl-O—C(O)—, ($C_1$-$C_4$)alkyl-NH—C(O)—, ($C_1$-$C_4$)alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4e'}$ taken together with $R^{4b}$, $R^{4b'}$, $R^{4c}$, or $R^{4c'}$ forms a bond, a methylene bridge, or an ethylene bridge (preferably, Z is a bond, —$CH_2CH_2$— or —$C(R^{4c})(R^{4c'})$—, where $R^{4c}$ and $R^{4c'}$ are each independently hydrogen or ($C_1$-$C_6$)alkyl);

$R^{4f}$ is hydrogen, cyano, hydroxy, amino, $H_2NC(O)$—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, ($C_1$-$C_4$)alkyl)$_2$N—C(O)—, ($C_1$-$C_6$)alkylamino-, (($C_1$-$C_4$)alkyl)$_2$amino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where the moiety is optionally substituted with one or more substituents; and $R^{4f'}$ is hydrogen, $H_2NC(O)$—, or a chemical moiety selected from the group consisting of ($C_1$-$C_6$)alkyl, acyl, ($C_1$-$C_3$)alkyl-O—C(O)—, ($C_1$-$C_4$)alkyl-NH—C(O)—, ($C_1$-$C_4$)alkyl)$_2$N—C(O)—, aryl, heteroaryl, a 3-6 membered partially or fully saturated heterocycle, and a 3-6 membered partially or fully saturated carbocyclic ring, where the moiety is optionally substituted with one or more substituents, or $R^{4f'}$ or $R^{4'}$ taken together with $R^{4b}$, $R^{4b'}$, $R^{4c}$, or $R^{4c'}$ forms a bond, a methylene bridge, or an ethylene bridge; a pharmaceutically acceptable salt thereof, a prodrug of the compound or the salt, or a solvate or hydrate of the compound, the salt or the prodrug.

Preferred compounds include: 4-(1-benzylpyrrolidin-3-yloxy)-7-(2-chlorophenyl)-8-(4-chlorophenyl)-2-methylpyrazolo[1,5-a][1,3,5]triazine; 7-(2-chlorophenyl)-8-(4-chlorophenyl)-4-(1-cyclohexylazetidin-3-yloxy)-2-methylpyrazolo[1,5-a][1,3,5]triazine; 4-(1-tert-butylazetidin-3-yloxy)-7-(2-chlorophenyl)-8-(4-chlorophenyl)-2-methylpyrazolo[1,5-a][1,3,5]triazine; and 7-(2-chlorophenyl)-8-(4-chlorophenyl)-4-(1-isopropylazetidin-3-yloxy)-2-methylpyrazolo[1,5-a][1,3,5]triazine; a pharmaceutically acceptable salt thereof or a solvate or hydrate of said compound or said salt.

Yet another preferred compound of the present invention is a compound of Formula (I) or (II) where $R^4$ is a group of Formula (IC), where where $R^5$ and $R^6$ are each independently hydrogen or ($C_1$-$C_4$)alkyl, and $R^7$ is ($C_1$-$C_4$)alkyl-, halo-substituted ($C_1$-$C_4$)alkyl-, ($C_1$-$C_4$)alkoxy($C_1$-$C_4$)alkyl-, ($C_1$-$C_4$)alkylamino($C_1$-$C_4$)alkyl-, di($C_1$-$C_4$)alkylamino($C_1$-$C_4$)alkyl-, or a 4-6 membered partially or fully saturated heterocylic ring containing 1 to 2 heteroatoms independently selected from oxygen, sulfur or nitrogen, or $R^5$ and $R^6$ or $R^5$ and $R^7$ taken together form a 5-6 membered lactone, 4-6 membered lactam, or a 4-6 membered partially or fully saturated heterocycle containing 1 to 2 heteroatoms independently selected from oxygen, sulfur or nitrogen, where the lactone, the lactam and the heterocycle are optionally substituted with one or more substituents; a pharmaceutically acceptable salt thereof, a prodrug of the compound or the salt, or a solvate or hydrate of the compound, the salt or the prodrug. Preferably, $R^5$ and $R^6$ are each independently hydrogen or ($C_1$-$C_4$)alkyl, and $R^7$ is ($C_1$-$C_4$)alkyl.

Preferred compounds include: 7-(2-chlorophenyl)-8-(4-chlorophenyl)-4-isopropoxy-2-methylpyrazolo[1,5-a][1,3,5]triazine; 7-(2-chlorophenyl)-8-(4-chlorophenyl)-4-ethoxy-2-methylpyrazolo[1,5-a][1,3,5]triazine; 7-(2-chlorophenyl)-8-(4-chlorophenyl)-2-methyl-4-propoxypyrazolo[1,5-a][1,3,5]triazine; and 4-butoxy-7-(2-chlorophenyl)-8-(4-chlorophenyl)-2-methylpyrazolo[1,5-a][1,3,5]triazine; a pharmaceutically acceptable salt thereof or a solvate or hydrate of said compound or said salt.

Preferred compounds where $R^4$ is (iii) an amino group include: butyl-[7-(2-chlorophenyl)-8-(4-chlorophenyl)-2-methylpyrazolo[1,5-a][1,3,5]triazin-4-yl]-amine; [7-(2-chlorophenyl)-8-(4-chlorophenyl)-2-methylpyrazolo[1,5-a][1,3,5]triazin-4-yl]-[2-(4-fluorophenyl)-ethyl]-amine; [7-(2-chlorophenyl)-8-(4-chlorophenyl)-2-methylpyrazolo[1,5-a][1,3,5]triazin-4-yl]-(2-morpholin-4-yl-ethyl)-amine; [7-(2-chlorophenyl)-8-(4-chlorophenyl)-2-methylpyrazolo[1,5-a][1,3,5]triazin-4-yl]-(6-methoxypyridin-3-yl)-amine; [7-(2-chlorophenyl)-8-(4-chlorophenyl)-2-methylpyrazolo[1,5-a][1,3,5]triazin-4-yl]-(2,2,2-trifluoroethyl)-amine; [7-(2-chlorophenyl)-8-(4-chlorophenyl)-2-methylpyrazolo[1,5-a][1,3,5]triazin-4-yl]-methyl-(2,2,2-trifluoroethyl)-amine; [7-(2-chlorophenyl)-8-(4-chlorophenyl)-2-methylpyrazolo[1,5-a][1,3,5]triazin-4-yl]-isopropylamine; and [7-(2-chlorophenyl)-8-(4-chlorophenyl)-2-methylpyrazolo[1,5-a][1,3,5]triazin-4-yl]-(2,2-difluoropropyl)-amine; a pharmaceutically acceptable salt thereof or a solvate or hydrate of said compound or said salt.

A preferred compound where $R^4$ is (iv) an ($C_1$-$C_6$)alkyl or ($C_1$-$C_6$)alkenyl group is 7-(2-chlorophenyl)-8-(4-chlorophenyl)-4-(1-ethoxyvinyl)-2-methylpyrazolo[1,5-a][1,3,5]triazine; a pharmaceutically acceptable salt thereof, or a solvate or hydrate of said compound or said salt.

Another aspect of the present invention includes the following compounds of Formula (Id), (Ie), (If), (2a) and (2b) which are useful intermediates in the synthesis of compounds of Formula (I).

(1d)

(1e)

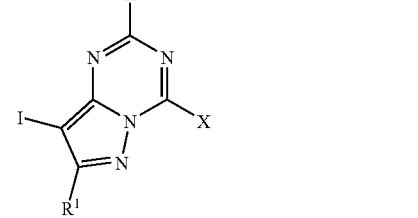

-continued

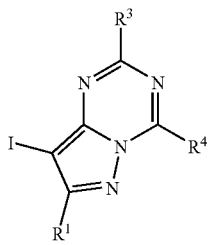
(1f)

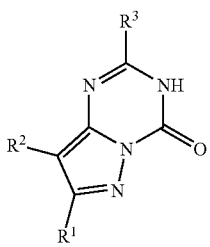
(2a)

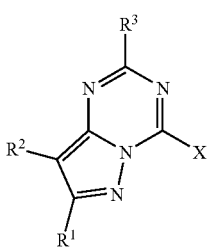
(2b)

wherein X is a leaving group (preferably, Cl) and $R^1$, $R^3$ and $R^4$ are as defined above for the compound of Formula (I).

Yet another aspect of the present invention includes the following compounds of Formula (II-a) and (II-b) which are useful intermediates in the synthesis of compounds of Formula (II).

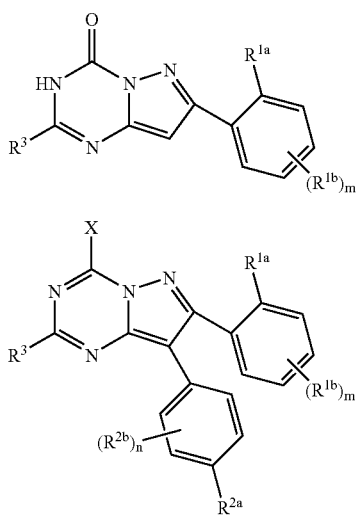
(II-a)

(II-b)

wherein X is a leaving group (preferably, Cl) and $R^{1a}$, $R^{1b}$, m, $R^{2a}$, $R^{2b}$, n and $R^3$ are as defined above for the compound of Formula (II).

Some of the compounds described herein contain at least one chiral center; consequently, those skilled in the art will appreciate that all stereoisomers (e.g., enantiomers and diasteroisomers) of the compounds illustrated and discussed herein are within the scope of the present invention. In addition, tautomeric forms of the compounds are also within the scope of the present invention. Those skilled in the art will recognize that chemical moieties such as an alpha-amino ether or an alpha-chloro amine may be too unstable to isolate; therefore, such moieties do not form a part of this invention.

Compounds of the present invention have been shown to be useful cannabinoid receptor ligands (in particular, CB1 receptor antagonists). Accordingly, another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include nicotine receptor partial agonists, opioid antagonists (e.g., naltrexone and nalmefene), dopaminergic agents (e.g., apomorphine), attention deficit disorder (ADD including attention deficit hyperactivity disorder (ADHD)) agents (e.g., Ritalin™, Strattera™, Concerta™ and Adderall™), and anti-obesity agents (described herein below).

In yet another embodiment of the present invention, a method for treating a disease, condition or disorder modulated by a cannabinoid receptor (in particular, a CB1 receptor) antagonist in animals that includes the step of administering to an animal in need of such treatment a therapeutically effective amount of a compound of the Formula (III) (or a pharmaceutical composition thereof).

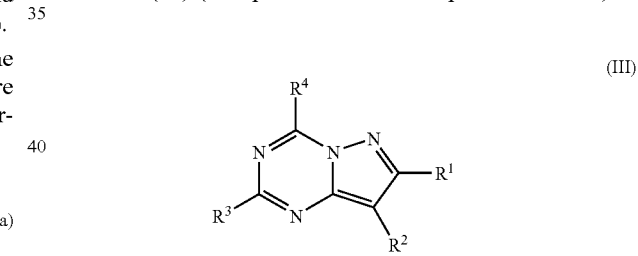
(III)

wherein $R^1$ is an optionally substituted aryl or an optionally substituted heteroaryl; $R^2$ is an optionally substituted aryl or an optionally substituted heteroaryl; $R^3$ is hydrogen, ($C_1$-$C_4$)alkyl, halo-substituted ($C_1$-$C_4$)alkyl, or ($C_1$-$C_4$)alkoxy; and $R^4$ is as defined above for the compound of Formula (II);

a pharmaceutically acceptable salt thereof, a prodrug of the compound or the salt, or a solvate or hydrate of the compound, the salt or the prodrug.

Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, a typical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD/ADHD), Parkinson's disease, and type II diabetes. In a preferred embodiment, the method is used in the treatment of weight loss, obesity, bulimia, ADD/ADHD, Parkinson's disease, dementia, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ or analogs thereof, MCR-4 agonists, CCK-A agonists, monoamine reuptake inhibitors, sympathomimetic agents, $β_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists such as those described hereinbelow), thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described above and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described above and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions or disorders modulated by cannabinoid receptor antagonists in an animal. The kit comprises a) a suitable dosage form comprising a compound of the present invention; and b) instructions describing a method of using the dosage form to treat diseases, conditions or disorders that are modulated by cannabinoid receptor (in particular, the CB1 receptor) antagonists.

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described herein, and (ii) a pharmaceutically acceptable carrier, excipient or diluent; and c) a container.

DEFINITIONS

As used herein, the term "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like). When substituted, the alkane radicals or alkyl moieties are preferably substituted with 1 to 3 fluoro substituents, or 1 or 2 substituents independently selected from ($C_1$-$C_3$)alkyl, ($C_3$-$C_6$)cycloalkyl, ($C_2$-$C_3$)alkenyl, aryl, heteroaryl, 3- to 6-membered heterocycle, chloro, cyano, hydroxy, ($C_1$-$C_3$) alkoxy, aryloxy, amino, ($C_1$-$C_6$)alkyl amino, di-($C_1$-$C_4$)alkyl amino, aminocarboxylate (i.e., ($C_1$-$C_3$)alkyl-O—C(O)— NH—), hydroxy($C_2$-$C_3$)alkylamino, or keto (oxo), and more preferably, 1 to 3 fluoro groups, or 1 substituent selected from ($C_1$-$C_3$)alkyl, ($C_3$-$C_6$)cycloalkyl, ($C_6$)aryl, 6-membered-heteroaryl, 3- to 6-membered heterocycle, ($C_1$-$C_3$) alkoxy, ($C_1$-$C_4$)alkyl amino or di-($C_1$-$C_2$)alkyl amino.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. When substituted, the carbocyclic group is preferably substituted with 1 or 2 substituents independently selected from ($C_1$-$C_3$)alkyl, ($C_2$-$C_3$)alkenyl, ($C_1$-$C_6$)alkylidenyl, aryl, heteroaryl, 3- to 6-membered heterocycle, chloro, fluoro, cyano, hydroxy, ($C_1$-$C_3$)alkoxy, aryloxy, amino, ($C_1$-$C_6$) alkyl amino, di-($C_1$-$C_4$)alkyl amino, aminocarboxylate (i.e., ($C_1$-$C_3$)alkyl-O—C(O)—NH—), hydroxy($C_2$-$C_3$)alkylamino, or keto (oxo), and more preferably 1 or 2 from substituents independently selected from $(C_1-C_2)$alkyl, 3- to 6-membered heterocycle, fluoro, $(C_1-C_3)$alkoxy, $(C_1-C_4)$ alkyl amino or di-$(C_1-C_2)$alkyl amino. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubstiuted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents independently selected from $(C_1-C_3)$alkyl, $(C_3-C_6)$cycloalkyl, $(C_2-C_4)$alkenyl, aryl, heteroaryl, 3- to 6-membered heterocycle, chloro, fluoro, cyano, hydroxy, $(C_1-C_3)$alkoxy, aryloxy, amino, $(C_1-C_6)$alkyl amino, di-$(C_1-C_3)$alkyl amino, aminocarboxylate (i.e., $(C_1-C_3)$alkyl-O—C(O)—NH—), or keto (oxo), and more preferably with 1 or 2 substituents independently selected from $(C_1-C_3)$alkyl, $(C_3-C_6)$cycloalkyl, $(C_6)$aryl, 6-membered-heteroaryl, 3- to 6-membered heterocycle, or fluoro. The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted." Substituted aryl groups include a chain of aromatic moieties (e.g., biphenyl, terphenyl, phenylnaphthalyl, etc.). When substituted, the aromatic moieties are preferably substituted with 1 or 2 substituents independently selected from $(C_1-C_4)$alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$ alkyl amino, di-$(C_1-C_3)$alkyl amino, or aminocarboxylate (i.e., $(C_1-C_3)$alkyl-O—C(O)—NH—), and more preferably, 1 or 2 substituents selected independently from $(C_1-C_4)$ alkyl, chloro, fluoro, cyano, hydroxy, or $(C_1-C_4)$alkoxy. The aryl group may be attached to the chemical entity or moiety by any one of the carbon atoms within the aromatic ring system. Similarly, the aryl portion (i.e., aromatic moiety) of an aroyl, aroyloxy (i.e., (aryl)-C(O)—O—), aryl substituted alkyl, and so on has the same definition as above.

The term "heteroaryl" or "heteroaromatic ring" refers to aromatic moieties containing at least one heteratom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted." When substituted, the heteroaromatic moieties are preferably substituted with 1 or 2 substituents independently selected from $(C_1-C_4)$ alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$alkyl-O—C(O)—NH—), and more preferably, 1 or 2 substituents independently selected from $(C_1-C_4)$alkyl, chloro, fluoro, cyano, hydroxy, $(C_1-C_4)$alkoxy, $(C_1-C_4)$alkyl amino or di-$(C_1-C_2)$alkyl amino. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl, heteroaroyloxy (i.e., (heteroaryl)-C(O)—O—) or heteroaryl substituted alkyl, and so on has the same definition as above.

The term "acyl" refers to alkyl, partially saturated or fully saturated cycloalkyl, partially saturated or fully saturated heterocycle, aryl, and heteroaryl substituted carbonyl groups. For example, acyl includes groups such as $(C_1-C_6)$ alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include $(C_1-C_6)$alkyl, $(C_3-C_7)$cycloalkyl, $(C_2-C_6)$alkenyl, $(C_1-C_6)$alkylidenyl, aryl, heteroaryl, 3- to 6-membered heterocycle, halo (e.g., chloro, bromo, iodo and fluoro), cyano, hydroxy, $(C_1-C_6)$alkoxy, aryloxy, sulfhydryl (mercapto), $(C_1-C_6)$alkylthio, arylthio, amino, mono- or di-$(C_1-C_6)$alkyl amino, quaternary ammonium salts, amino$(C_1-C_6)$alkoxy, aminocarboxylate (i.e., $(C_1-C_6)$alkyl-O—C(O)—NH—), hydroxy$(C_2-C_6)$alkylamino, amino$(C_1-C_6)$alkylthio, cyanoamino, nitro, $(C_1-C_6)$carbamyl, keto (oxo), acyl, $(C_1-C_6)$alkyl-$CO_2$—, glycolyl, glycyl, hydrazino, guanyl, sulfamyl, sulfonyl, sulfinyl, thio$(C_1-C_6)$alkyl-C(O)—, thio$(C_1-C_6)$alkyl-$CO_2$—, and combinations thereof. In the case of substituted combinations, such as "substituted aryl $(C_1-C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "solvate" refers to a molecular complex of a compound represented by Formula (I), (II), or (III) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated by a cannabinoid receptor" or "modulation of a cannabinoid receptor" refers to the activation or deactivation of a cannabinoid receptor. For example, a ligand may act as an agonist, partial agonist, inverse agonist, antagonist, or partial antagonist.

The term "antagonist" includes both full antagonists and partial antagonists, as well as inverse agonists.

The term "CB-1 receptor" refers to the G-protein coupled type 1 cannabinoid receptor.

The term "compounds of the present invention" (unless specifically identified otherwise) refer to compounds of Formula (I), Formula (II) and Formula (III), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by cannabinoid receptor antagonists.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Compounds of Formula (I) can be prepared using procedures analogous to those described in He, L., et al., "4-(1,3-Dimethoxyprop-2-ylamino)-2,7-dimethyl-8-(2,4-dichlorophenyl)pyrazolo[1,5-a]-1,3,5-triazine: A Potent, Orally Bioavailable $CRF_1$ Receptor Antagonist," *J. Med. Chem.*, 43, 449-456 (2000) and U.S. Pat. No. 3,910,907, incorporated herein by reference. Other useful routes to compounds of Formula (I) are described in H. Beyer et al. *Chem. Ber.*, 93, 2209-2216 (1960), J. Kobe et al. *J. Heterocycl. Chem.*, 11, 991-996 (1974), and K. Senga et al. *J. Med. Chem.*, 25, 243-249 (1982). Scheme I outlines the procedures one could use to provide compounds of the present invention via pyrazolo-triazinone intermediates (1c) and (1d).

The 3-aminopyrazole (1a) may be purchased or prepared using procedures analogous to those described in Pakamigawa, A., *Yakugaku Zasski*, 84, 1113 (1964).

Amidine (1b) may be formed in a reaction inert solvent (e.g., acetonitrile, methylene chloride, chloroform) from the condensation of 3-aminopyrazole (1a) with an alkyl imidate ($R^3C(=NH)OAlkyl$) in the presence or absence of an acid. Preferred alkylimidates include ethyl acetimidate, methyl acetimidate, and ethyl formimidate. Acids include alkanoic acids (e.g., acetic acid, trifluoroacetic acid), sulfonic acids (e.g., benzenesulfonic acid, p-toluenesulfonic acid, methanesulfonic acid, sulfuric acid) and hydrochloric acid. Isolation of amidine (1b) as its acetic acid salt is particularly preferred.

Pyrazolotriazinone (1c) may be formed by treating amidine (1b) with dialkyl carbonates (e.g., diethyl carbonate, dimethylcarbonate) or dialkyl dithiocarbonates in the presence of base (e.g., sodium methoxide, sodium ethoxide) in

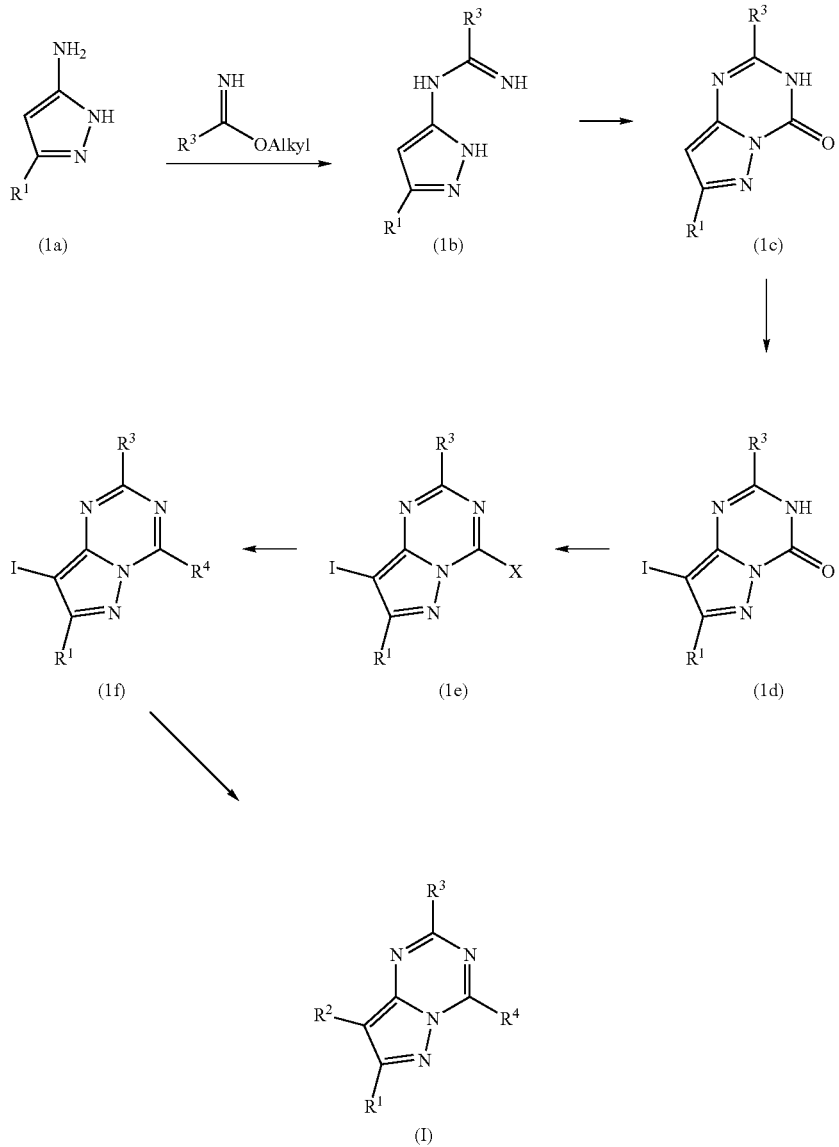

Scheme I a suitable solvent (e.g., methanol, ethanol) at reaction temperatures from about 30° C. to 150° C. Alternatively, pyrazolotriazinone (1c) may be formed by treating amidine (1b) with reagents such as phosgene, triphosgene, or carbonyl diimidazole in the presence or absensce of base (e.g., triethylamine, diisopropylethyl amine, pyridine, imidazole) in a reaction inert solvent (e.g., methylene chloride, tetrahydrofuran, diethyl ether, diisopropyl ether, methyl tert-butyl ether and acetonitrile) at reaction temperatures from about −40° C. to 100° C.

Alternatively, pyrazolotriazinone (1c, $R^3$=H) may be formed by treating 3-aminopyrazole (1a) with 1,3-dimethyl-5-azauracil in the presence of a strong base (e.g., sodium ethoxide) according to procedures described by C. K. Chu et al. in *Nucleic Acid Chem.*, 4, 19-23 (1991).

A bromine or iodine may be installed at the 3-position of pyrazolotriazinone (1c) using procedures analogous to those described in Senga, K., et al., *J. Med. Chem.*, 25, 243-249 (1982). For instance, position 3 may be iodinated by treating the pyrazolotriazinone (1c) with a reagent such as N-iodosuccinimide (NIS), iodine, or iodonium bis-symcollidine perchlorate (preferably NIS) in an aprotic solvent (e.g., carbon tetrachloride, methylene chloride, or chloroform). Suitable reaction temperatures range from about −78° C. to 30° C., and is preferably conducted at around 0° C.

Conversion of the iodo-substituted pyrazolotriazinone (1d) to the 7-halopyrazolotriazine ((1e), X=Cl, Br) may be accomplished by treatment with a halogenating agent (e.g., $SOCl_2$, $POCl_3$, $PCl_3$, $PCl_5$, $POBr_3$, $PBr_3$, $PBr_5$, or $PPh_3$/NBS) in the presence of absence of base (e.g., triethylamine, diisopropylethylamine, pyridine, N,N-diethylaniline) in the presence or absence of a reaction inert solvent (e.g., toluene, xylenes, dioxane) at temperatures ranging from about −40° C. to 200° C. (For analogous transformations, see: WO 02/072202 and O. Sugimoto et al., *Tetrahedron Lett.*, 40, 7477-7478 (1999)). In a preferred example, pyrazolotriazinone (1d) is treated with phosphorus oxychloride in the presence of a trialkylamine base (e.g., triethylamine, diisopropylethylamine) in refluxing toluene to give the corresponding 7-chloropyrazolotriazine (1e). Alternatively, pyrazolotriazinone (1d) may be activated ((1e), X=leaving group) by treatment with reagents like methanesulfonic anhydride, methanesulfonyl chloride, trifluormethanesulfonic anhydride, or p-toluenesulfonyl chloride in a reaction inert solvent (e.g., methylene chloride) in the presence of a suitable base (e.g., triethylamine, diisopropylethylamine, pyridine, collidine).

Substituent $R^4$, where $R^4$ is an amino group of Formula (IA) or an amino group substituted with one or more substituents described above, may be introduced via a coupling reaction between intermediate (1e) and the corresponding amino compound ($R^4$—H) to produce intermediate (1f). For example, intermediate (1e) is generally stirred with the desired amine ($R^4$—H). The amine may act as the solvent (e.g., butylamine, morpholine, pyrollidine) or a solvent (e.g., methylene chloride, N,N-dimethylformamide, water, dimethoxyethane) may be added to assist in solubilization of the reactants and/or provide a media having the appropriate refluxing temperature to complete the substitution. The reaction may be heated to accelerate the process. Suitable reaction temperatures range from about −40° C. to 100° C., and are preferably conducted at around 30° C. In addition, a suitable base (e.g., triethylamine, diisopropylethylamine) may be employed to quench the acid produced in the process. Suitable amino compounds can be either purchased commercially or easily prepared using standard procedures well-known to those skilled in the art. Preferred amino compounds ($R^4$—H) include 4-alkylaminopiperidine-4-carboxamides (Scheme III) and 3-alkylaminoazetidine-3-carboxamides that are described below.

Compounds of formula (I) may be prepared using procedures analogous to those described for Scheme 17 of U.S. Pat. No. 6,372,743, incorporated herein by reference. For example, the second aryl or heteroaryl group ($R^2$) is introduced via metal-mediated cross-coupling reactions such as the Suzuki reaction (See: A. Suzuki in *Metal-Catalyzed Cross-Coupling Reactions*; F. Diederich and P. J. Stang, Eds.; Wiley-VCH Verlag, Weinheim, Germany, Chapter 2 (1998) and N. Miyaura and A. Suzuki *Chem. Rev.*, 95, 2457-2483 (1995)) and the Stille reaction (T. N. Mitchell in *Metal-Catalyzed Cross-Coupling Reactions*; F. Diederich and P. J. Stang, Eds.; Wiley-VCH Verlag, Weinheim, Germany, Chapter 4 (1998)). In a preferred method, the compound of the Formula (I) may be produced by Suzuki reaction of intermediate (1f) with a compound of Formula $R^2$—$B(OH)_2$ in the presence of a complex or salt of palladium (e.g., $Pd(PPh_3)_4$, $PdCl_2dppf$, $Pd(OAc)_2$), a base (e.g., cesium carbonate, sodium carbonate, cesium fluoride, potassium phosphate), and a suitable solvent (e.g., toluene, water, dioxane, N,N-dimethylformamide, dimethoxyethane) in the presence or absence of added ligand (e.g., dppf, dppb). Preferred reaction temperatures range from about 0° C. to about 120° C. For a detailed description of a representative compound prepared using the procedures generally described in Scheme I above, see Examples 1A-1 and 6A-1 in the Examples section below.

Alternatively, the second aromatic group ($R^2$) may be introduced prior to the coupling of the desired amino compound ($R^4$—H). Scheme II below outlines the procedures that may be used in this alternative route.

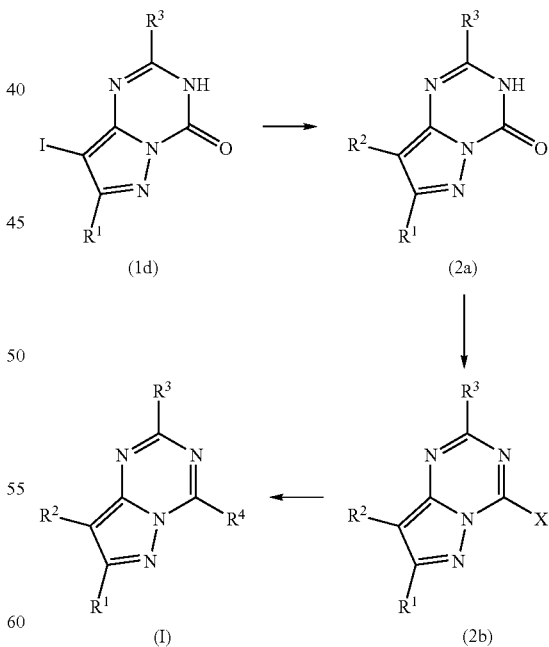

Scheme II

As described above in Scheme I, the second aryl or heteroaryl group ($R^2$) may be introduced via metal-mediated coupling (e.g., Suzuki reaction). For example, intermediate (1d) is reacted with a compound of Formula $R^2$—$B(OH)_2$ in the presence of a complex or salt of palladium, a base and a suitable solvent to produce intermediate (2a). The triazinone (2a) can then be activated as described above, such as by convertion to the corresponding 7-chloropyrazolotriazine ((2b), X=Cl) using the same general procedures described above in Scheme I for chlorinating intermediate (1d) to produce intermediate (1e). For example, triazinone (2a) may be treated with phosphorus oxychloride in the presence of a base (e.g., triethylamine or N,N-dimethylaniline) to give the corresponding chloro derivative (2b). Substituent $R^4$ (e.g., $R^4$=an amino group of Formula (IA) or an amino group substituted with one or more substituents described above) may be introduced via a coupling reaction between intermediate (2b) and the corresponding amino compound ($R^4$—H) to produce a compound of Formula (I) where $R^4$ is an amino group. For a more detailed description of representative compounds prepared using the procedures generally described in Scheme II, see Examples 2A-1, 3A-1, 7A-1, and 8A-1 in the Examples section below.

Compounds of Formula (I) above where $R^4$ is a primary or secondary amine can be alkylated, sulfonated and/or acylated to provide additional derivatives (e.g., alkylamines, dialkylamines, sulfonamides, amides, carbamates, ureas, etc.) using standard procedures well-known to those skilled in the art. In some cases, the Compounds of Formula (I) above where $R^4$ is a protected primary or secondary amine needs to be deprotected by methods well-known to those skilled in the art to unmask the primary or secondary amine prior to further functionalization. For a more detailed description of representative compounds prepared using the procedures generally described in Scheme II, see Examples 9A-1 and 10A-1 in the Examples section below.

Compounds of Formula (I) above where $R^4$ is an amino acid may be prepared as described by A. M. Shalaby et al. in *J. Chem. Res.*, 134-135 (1998). These materials may be further elaborated to amides and esters using standard procedures well-known to those skilled in the art.

Numerous amine compounds of Formula (IA) are available from commercial sources or prepared by known methods readily available to those skilled in the art. Representative preparations of amine compounds of Formula (IA) are illustrated in the Examples below. The preparation of 4-aminopiperidine-4-carboxamide groups of Formula (IA) and 4-amino-4-cyano piperidine groups of Formula (IA) and their benzyl protected precursors are described by P. A. J. Janssen in U.S. Pat. No. 3,161,644, C. van de Westeringh et al. in *J. Med. Chem.*, 7, 619-623 (1964), and K. A. Metwally et al. in *J. Med. Chem.*, 41, 5084-5093 (1998) where the above 4-amino groups are unsubstituted, monosubstituted, disubstituted, or part of a heterocyclic ring. Related bicyclic derivatives are described by K. Frohlich et al. in *Tetrahedron*, 54, 13115-13128 (1998) and references contained therein. Spiro-substituted piperidines of formula (IA) are described by P. A. J. Janssen in U.S. Pat. No. 3,155,670, K. A. Metwally et al. in *J. Med Chem.*, 41, 5084-5093 (1998), T. Toda et al. in *Bull. Chem. Soc. Japan*, 44, 3445-3450 (1971), and W. Brandau and S. Samnick in WO 9522544. The preparation of 3-aminoazetidine-3-carboxamide is described by A. P. Kozikowski and A. H. Fauq in *Synlett*, 783-784 (1991). The preparation of preferred 4-alkylaminopiperidine-4-carboxamide groups of Formula (IA) are depicted in Scheme III below. The corresponding 3-alkylaminoazetidine-3-carboxamides and 3-alkylaminopyrolidine-3-carboxamides may be prepared in an analogous fashion. Spiro-substituted derivates are available by procedures analgous to those contained in the above references. A detailed description of some representative spiro-substituted amines may be found in the "Preparation of Key Intermediates" section of the Examples below (see, e.g., I-3A-4b and I-3A5b). Spirocyclization may also be accomplished as the final step in the synthesis of compounds of formula (I). For a more detailed description of a representative compound prepared using this procedure, see Example 4A-1 in the Examples section below.

Scheme III

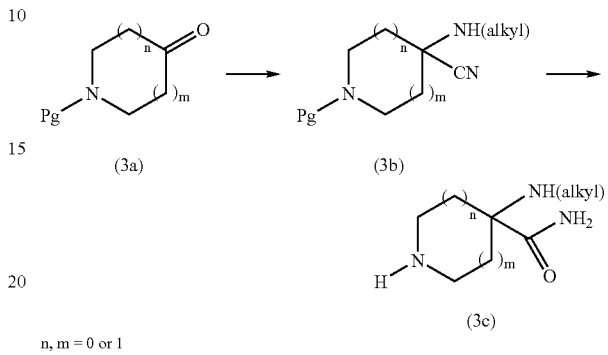

n, m = 0 or 1

The amino group of 4-piperidinone is first protected to provide intermediate (3a). A useful protecting group is benzyl. 4-Piperidinone and derivatives thereof may be purchased commercially from a variety of sources (e.g., Interchem Corporation, Paramus, N.J. and Sigma-Aldrich Co., St. Louis, Mo.). Piperidinone (3a) is then reacted with the desired alkylamine and potassium cyanide in an aqueous HCl/ethanol solvent mixture at about 0° C. to about 30° C. The cyano group is converted to the corresponding amide with acid and water, or with alkaline hydrogen peroxide in the presence of DMSO (see Y. Sawaki and Y. Ogata in *Bull. Chem. Soc. Jpn.* 54, 793-799 (1981)). The protecting group is then removed using conventional methods for the particular protecting group employed. For example, a benzyl-protecting group may be removed by hydrogenation in the presence of Pd/C. A detailed description of some representative amines having Formula (3c) above may be found in the "Preparation of Key Intermediates" section of the Examples below (see, e.g., I-1A-1h, I-2A-1g, I-3A-1c, I-3A-2c, I-3A-3c, and I-3A-6a).

For those compounds of Formula (I) where $R^4$ is an unsubstituted or substituted alkoxy group, intermediate (1e) or (2b) may be treated with the desired alcohol in the presence of a base (e.g., potassium t-butoxide, NaH, 1,4-diazabicyclo[2.2.2]octane, diisopropylethylamine, $NaHCO_3$). The alcohol may act as solvent, or an aprotic solvent may be added to assist in solubilization of the reactants and/or provide a media having the appropriate refluxing temperature to complete the substitution (e.g., THF, methylene chloride, DMF). Suitable alcohols can be either purchased commercially or easily prepared using standard procedures well known to those skilled in the art. For a detailed description of a representative compounds prepared where $R^4$ is an unsubstituted or substituted alkoxy group, see Examples 11A-1, 12A-1, and 13A-1 in the Examples section below.

For those compounds of Formula (I) where $R^4$ is an unsubstituted or substituted alkyl or alkenyl group, intermediate (2b) may be functionalized using metal-mediated cross-coupling reactions as described above. For a detailed description of a representative compound prepared where $R^4$ is a substituted alkenyl group, see Example 14A-1 in the Examples section below. Compounds of Formula (I) where $R^4$ is an unsubstituted or substituted alkyl or alkenyl group may also be prepared using procedures analogous to those described in U.S. Pat. No. 6,313,124 (see Schemes 7, 11, and 12, and Examples 3 and 431), incorporated herein by reference.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, N-oxide, or prodrug with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulfonate salts, and the like. A preferred salt of the compounds of the present invention is the hydrochloride salt. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the present invention contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is selected from the naturally occurring L-amino acids, $P(O)(OH)_2$, $P(O)(O(C_1-C_6)alkyl)_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY' wherein Y' is H, $(C_1-C_6)$alkyl or benzyl, —C(OY$_0$)Y$_1$ wherein Y$_0$ is $(C_1-C_4)$alkyl and Y$_1$ is $(C_1-C_6)$ alkyl, carboxy$(C_1-C_6)$alkyl, amino$(C_1-C_4)$alkyl or mono-N— or di-N,N-$(C_1-C_6)$alkylaminoalkyl, —C(Y$_2$)Y$_3$ wherein Y$_2$ is H or methyl and Y$_3$ is mono-N— or di-N,N-$(C_1-C_6)$alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers)

include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, a typical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD including attention deficit hyperactivity disorder (ADHD)), Parkinson's disease, and type II diabetes.

Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, posttraumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $\beta_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345; and 6,326,375; US Publication Nos. 2002/0151456 and 2003/036652; and PCT Publication Nos. WO 03/010175. WO 03/082190 and WO 02/048152), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, pseudoephedrine, $PYY_{3-36}$ or an analog thereof, and 2-oxo-N-(5-phenylpyrazinyl)spiro-[isobenzofuran-1 (3H),4'-piperidine]-1'-carboxamide. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540, 917; and 5,643,874; $PYY_{3-36}$ (including analogs) can be prepared as described in US Publication No. 2002/0141985 and WO 03/027637; and the NPY Y5 receptor antagonist 2-oxo-N-(5-phenylpyrazinyl)spiro[isobenzofuran-1 (3H),4'-piperidine]-1'-carboxamide can be prepared as described in US Publication No. 2002/0151456. Other useful NPY Y5 receptor antagonists include those described in PCT Publication No. 03/082190, such as 3-oxo-N-(5-phenyl-2-pyrazinyl)-spiro[isobenzofuran-1(3H), 4'-piperidine]-1'-carboxamide; 3-oxo-N-(7-trifluoromethylpyrido[3,2-b]pyridin-2-yl)-spiro-[isobenzofuran-1 (3H), 4'-piperidine]-1'-carboxamide; N-[5-(3-fluorophenyl)-2-pyrimidinyl]-3-oxospiro-[isobenzofuran-1 (3H), [4'-piperidine]-1'-carboxamide; trans-3'-oxo-N-(5-phenyl-2-pyrimidinyl)] spiro[cyclohexane-1,1'(3'H)-isobenzofuran]-4-carboxamide; trans-3'-oxo-N-[1-(3-quinolyl)-4-imidazolyl] spiro[cyclohexane-1,1'(3'H)-isobenzofuran]-4-carboxamide; trans-3-oxo-N-(5-phenyl-2-pyrazinyl)spiro[4-azaiso-benzofuran-1 (3H),1'-cyclohexane]-4'-carboxamide; trans-N-[5-(3-fluorophenyl)-2-pyrimidinyl]-3-oxospiro[5-azaisobenzofuran-1(3H), 1'-cyclohexane]-4'-carboxamide; trans-N-[5-(2-fluorophenyl)-2-pyrimidinyl]-3-oxospiro[5-azaisobenzofuran-1 (3H),1'-cyclohexane]-4'-carboxamide; trans-N-[1-(3,5-difluorophenyl)-4-imidazolyl]-3-oxospiro [7-azaisobenzofuran-1 (3H),1'-cyclohexane]4'-carboxamide; trans-3-oxo-N-(1-phenyl-4-pyrazolyl)spiro[4-azaisobenzofuran-1 (3H),1'-cyclohexane]-41-carboxamide; trans-N-[1-(2-fluorophenyl)-3-pyrazolyl]-3-oxospiro[6-azaisobenzofuran-1 (3H), 1'-cyclohexane]-4'-carboxamide; trans-3-oxo-N-(1-phenyl-3-pyrazolyl)spiro[6-azaisobenzofuran-1 (3H),1'-cyclohexane]4'-carboxamide; trans-3-oxo-N-(2-phenyl-1,2,3-triazol-4-yl)spiro[6-azaisobenzofuran-1 (3H),1'-cyclohexane]-4'-carboxamide; and pharmaceutically acceptable salts and esters thereof. All of the above recited U.S. patents and publications are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; $\alpha$2-antagonists and imidazolines: midaglizole, isaglidole, deriglidole, idazoxan, efaroxan, fluparoxan; other insulin secretagogues: linogliride, A4166; glitazones: ciglitazone, Actos® (pioglitazone), englitazone, troglitazone, darglitazone, Avandia® (BRL49653); fatty acid oxidation inhibitors: clomoxir, etomoxir; $\alpha$-glucosidase inhibitors: acarbose, miglitol, emiglitate, voglibose, MDL-25,637, camiglibose, MDL-73,945; $\beta$-agonists: BRL 35135, BRL 37344, RO 16-8714, ICI D7114, CL 316,243; phosphodiesterase inhibitors: L-386, 398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor (e.g., atorvastatin or the hemicalcium salt thereof), or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent will also be generally dependent upon a number of factors including the health of the subject being treated, the extent of treatment desired, the nature and kind of concurrent therapy, if any, and the frequency of treatment and the nature of the effect desired. In general, the dosage range of an anti-obesity agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert customary pharmaceutical excipient (or carrier) such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound of the present invention or the combination, may further comprise suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile conditions with a pharmaceutically acceptable carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of a compound of the present invention or combination (i.e., a compound of the present invention with at least one additional pharmaceutical agent) can be effected orally or non-orally (e.g., by injection).

An amount of a compound of the present invention (or combination) is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound with an excipient, diluent or carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 or 500 (available from Varian Inc., Palo Alto, Calif.) at room temperature at 400 and 500 MHz $^1$H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and only the lower mass ion is given. MS peaks are reported for all examples.

Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

Preparation of Key Intermediates

Preparation of Intermediate N-[5-(2-Chlorophenyl)-2H-pyrazol-3-yl]-acetamidine, Acetate Salt (I-1A-1a)

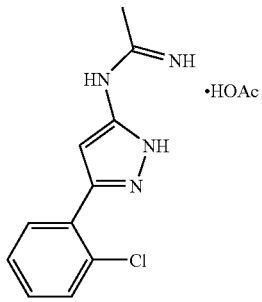

I-1A-1a

To a solution of 2-chlorobenzoylacetonitrile (400 g, 2.23 mol) in ethanol (9 L) was added hydrazine hydrate (221 g, 4.42 mol) over 15 minutes while maintaining internal reaction temperature at 15 to 25° C. The mixture was then heated at 75° C. for 20 hr. After cooling, the reaction was concentrated, in vacuo, to give a brown oil. The residue was dissolved in ethyl acetate (4 L), washed with half saturated brine (4 L), and then dried (Na$_2$SO$_4$) to a give a crude, dark orange solution of 5-(2-chlorophenyl)-2H-pyrazol-3-ylamine that was carried directly into the next reaciton: +ESI MS (M+1) 194.0.

To a stirred solution of potassium carbonate (2 Kg) in water (5 L) was added solid ethyl acetimidate hydrochloride salt (731 g, 5.83 mol), portionwise, over 10 minutes. The ethyl acetimidate free base was extracted into ethyl acetate (4 L), separated and the organic layer then dried (Na$_2$SO$_4$).

To the stirred ethyl acetate solution of 5-(2-chlorophenyl)-2H-pyrazol-3-ylamine was added the ethyl acetimidate free base solution over 10 minutes. Glacial acetic acid (140 ml, 2.42 mol) was then added over a 20-minute period while maintaining the reaction between 10 and 30° C. A precipitate began to form after approximately 15 ml of acetic acid had been added. After stirring for 5 hours, the product was collected on a course sintered glass funnel. The product on the filter was washed with ethyl aceate until the eluent was colorless. After drying overnight on the frit under a stream of air using low vacuum, intermediate I-1A-1a was obtained as an off-white, crystalline solid (543 g, 82.6%): +ESI MS (M+1) 235.1; $^1$H NMR (400 MHz, CD$_3$OD) δ 7.58-7.52 (m, 2H), 7.42-7.39 (m, 2H), 6.43 (s, 1H), 2.38 (s, 3H), 1.86 (s, 3H).

Preparation of Intermediate N-[5-(2-Chlorophenyl)-2H-pyrazol-3-yl]-acetamidine (I-1A-1b)

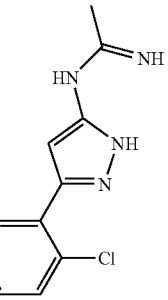

I-1A-1b

To a stirred mixture of 2 M aqueous NaOH (75 mL, 152 mol) and 2-methyltetrahydrofuran (155 ml) was added N-[5-(2-chlorophenyl)-2H-pyrazol-3-yl]-acetamidine, acetate salt (I-1A-1a; 11.5 g, 39.0 mmol), portionwise, over 15 minutes at room temperature. The organic layer was separated, washed with brine (75 ml), and then concentrated to one half volume, at which time a precipitate begins to form. The stirred mixture was diluted with MTBE (70 mL), cooled to −5° C. in an ice/brine bath for 1 hour, and the resulting precipitate collected on a course sintered glass funnel. The solid was washed with ice cold MTBE (50 mL) and then dried, in vacuo, to afford intermediate I-1A-1b as a solid (5.74 g, 63%): +ESI MS (M+1) 235.3; $^1$H NMR (400 MHz, CD$_3$OD) δ 7.56-7.53 (m, 1H), 7.48-7.44 (m, 1H), 7.36-7.28 (m, 2H), 6.27 (s, 1H), 2.04 (s, 3H).

Preparation of Intermediate 7-(2-Chlorophenyl)-2-methyl-3H-pyrazolo[1,5-a][1,3,5]triazin-4-one (I-1A-1c)

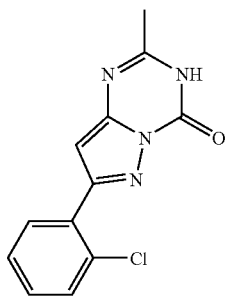

I-1A-1c

To an ethanolic solution of sodium ethoxide, generated by portionwise addition of sodium metal (10.5 g, 455 mmol) to stirred ethanol (450 ml), was added N-[5-(2-chlorophenyl)-2H-pyrazol-3-yl]-acetamidine, acetate salt (I-1A-1b; 13.4 g, 45.5 mmol) in one portion. Diethylcarbonate (44.1 ml, 364 mmol) was added, dropwise, and the mixture was heated to reflux, overnight. After cooling to room temperature, the reaction was concentrated, in vacuo, and then extracted with ethyl acetate from water, adjusted to pH 6 with 3 M aqueous HCL. The combined organic layers were washed with brine, dried (MgSO$_4$), filtered, and then concentrated, in vacuo, to afford the crude product as an off-white solid (11.0 g). The solids were triturated from ethyl acetate (100 ml), the supernate was decanted away, the solids were washed with additional ethyl acetate (100 ml) and then dried, in vacuo, to afford I-1A-1c as a colorless solid (10.0 g, 84%): +APcI MS (M+1) 261.2; ¹H NMR (400 MHz, CD₃OD) δ 7.84-7.81 (m, 1H), 7.54-7.51 (m, 1H), 7.44-7.38 (m, 2H), 6.77 (s, 1H), 2.42 (s, 3H).

Alternative Preparation of Intermediate 7-(2-Chlorophenyl)-2-methyl-3H-pyrazolo[1,5-a][1,3,5]triazin-4-one (I-1A-1c)

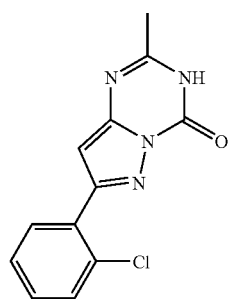

I-1A-1c

To a pale yellow solution of N-[5-(2-chlorophenyl)-2H-pyrazol-3-yl]-acetamidine (I-1A-1b; 2.04 g, 8.69 mmol) in DMSO (17 mL) was added 1,1'-carbonyldiimidazole (1.53 g, 9.44 mmol), portionwise over 1 minute at room temperature. After stirring for one hour, the reaction was added to stirred 1 M aqueous HCl (17 ml) over 5 minutes. The colorless precipitate that formed was stirred for 2.5 hours and then collected on a course sintered funnel. The solids were washed with water (50 ml) and then dried on the frit under a stream of air using low vacuum to afford I-1A-1c as a colorless solid (2.29 g, quantitative): +APcI MS (M+1) 261.3.

Preparation of Intermediate 7-(2-Chlorophenyl)-8-iodo-2-methyl-3H-pyrazolo[1,5-a][1,3,5]triazin-4-one (I-1A-1d)

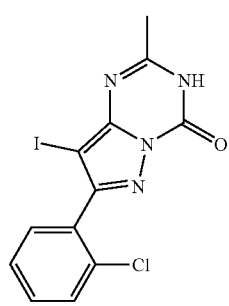

I-1A-1d

To a suspension of 7-(2-chlorophenyl)-2-methyl-3H-pyrazolo[1,5-a]-[1,3,5]triazin-4-one (I-1A-1c; 18.9 g, 72.6 mmol) in methylene chloride (290 ml) cooled in an ice bath was added N-iodosuccinimide (18.0 g, 79.9 mmol). The mixture became homogeneous orange solution within 5 minutes. After stirring for 5 hours, the mixture was washed with 50% saturated aqueous NH₄OH (160 ml), 1 M aqueous Na₂S₂O₃ (120 ml), and brine (120 ml). The solution was concentrated, in vacuo, and then concentrated again from MTBE (150 ml). Additional MTBE (75 ml) was added and stirred for 1 hour. The resulting solid precipitate was collected by vacuum filtration in a course sintered glass funnel, washed with MTBE (50 ml) and then dried, in vacuo, to afford product I-1A-1d as a solid (25.5 g, 91%): +APcI MS (M+1) 387.3; ¹H NMR (400 MHz, CD₃OD) δ 7.54 (d, J=7.1 Hz, 1H), 7.51-7.39 (m, 3H), 2.45 (S, 3H).

Preparation of Intermediate 4-Chloro-7-(2-chlorophenyl)-8-iodo-2-methylpyrazolo[1,5-a][1,3,5]triazine (I-1A-1e)

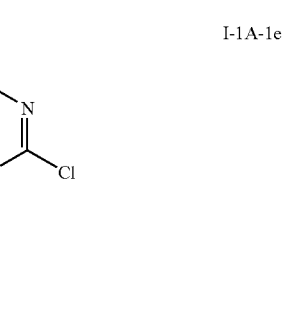

I-1A-1e

To a solution of 7-(2-chlorophenyl)-8-iodo-2-methyl-1H-pyrazolo[1,5-a][1,3,5]triazin-4-one (I-1A-1d; 1.00 g, 2.6 mmol) and diisopropylethylamine (0.68 ml, 3.8 mmol) in toluene (30 ml) at room temperature was added POCl₃ (1.28 ml, 14 mmol), dropwise. The mixture was heated at reflux for 5 hours, cooled to room temperature, and then concentrated, in vacuo, to a viscous oil. The residue was then purified by passing through a plug of silica gel on a sintered glass funnel using 20% ethyl acetate in hexanes as eluant to provide I-1A-1e as a yellow solid (0.93 g, 89%): +APcI MS (M+1) 316.3; ¹H NMR (400 MHz, CD₂Cl₂) δ 7.57 (d, J=7.9 Hz, 1H), 7.53-7.43 (m, 3H), 2.74 (s, 3H).

Preparation of Intermediate 1-Benzyl-4-ethylaminopiperidine-4-carbonitrile (I-1A-1f)

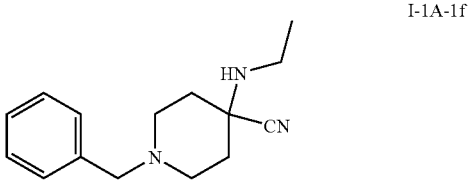

I-1A-1f

To a solution of 4-N-benzylpiperidone (5.69 g, 29.5 mmol) in ethanol (4.2 ml) cooled in an ice bath was added ethylamine hydrochloride (2.69 g, 32.3 mmol) in water (3 ml), keeping the internal temperature of the reaction below 10° C. A solution of KCN (2.04 g, 31.3 mmol) in water (7 ml) was added to the reaction solution over 10 minutes while keeping the internal temperature below 10° C. The reaction was then warmed to room temperature and stirred 18 hours. Isopropanol (10 ml) was added to the reaction mixture to give two distinct layers: lower colorless aqueous layer and an orange organic upper layer. The organic layer was separated and stirred with water (30 ml) for 30 minutes. The organic layer was separated (orange organic layer now the bottom layer), the solvent was removed in vacuo, and the resultant oil diluted in methylene chloride (30 ml). The organic layer was washed with brine, dried (Na₂SO₄), filtered and concentrated, in vacuo, to give I-1A-1f as an orange oil (6.05 g, 84%): +APcI MS (M+1) 244.2; 1H NMR (400 MHz, CD₂Cl₂) δ 7.32 (d, J=4.1 Hz, 4H), 7.29-7.23 (m, 1H), 3.54 (s, 2H), 2.81-2.76 (m, 2H), 2.75 (q, J=7.1 Hz, 2H), 2.35-2.29 (m, 2H), 2.01-1.98 (m, 2H), 1.74-1.68 (m, 2H), 1.14 (t, J=7.1 Hz, 3H).

Preparation of Intermediate
1-Benzyl-4-ethylaminopiperidine-4-carboxylic Acid
Amide (I-1A-1g)

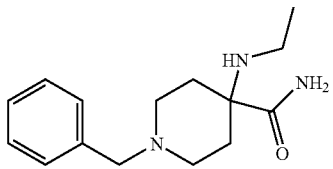

I-1A-1g

A solution of 1-benzyl-4-ethylaminopiperidine-4-carbonitrile I-1A-1f (0.58 g, 2.38 mmol) in methylene chloride (2 ml) cooled in an ice bath was treated with H₂SO₄ (1.8 ml, 33 mmol), dropwise, while keeping the internal temperature below 20° C. The reaction was then warmed to room temperature and stirred for 19 hours. After stirring was discontinued, the thick pale orange H₂SO₄ bottom layer was separated, cooled in an ice bath and then carefully quenched with concentrated NH₄OH keeping the internal temperature below 55° C. The aqueous layer was extracted with methylene chloride (2×10 ml), the combined organic layers were washed with brine (20 ml), dried (Na₂SO₄), and then concentrated, in vacuo, to afford I-1A-1q as a pale orange oil that solidified to a peach colored solid upon standing (0.54 g, 87%): +APcI MS (M+1) 262.2; ¹H NMR (400 MHz, CD₂Cl₂) δ 7.34-7.30 (m, 4H), 7.29-7.21 (m, 1H), 7.16 (br s, 1H), 3.48 (s, 2H), 2.71-2.68 (m, 2H), 2.47 (q, J=7.0 Hz, 2H), 2.17-2.02 (m, 4H), 1.62-1.58 (m, 2H), 1.41 (br s, 1H), 1.09 (t, J=7.0 Hz, 3H).

Preparation of Intermediate
4-Ethylaminopiperidine-4-carboxylic Acid Amide
(I-1A-1h)

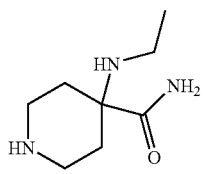

I-1A-1h

To a solution of 1-benzyl-4-ethylaminopiperidine-4-carboxylic acid amide (I-1A-1g; 7.39 g, 28.3 mmol) in methanol (100 ml) was added 20% Pd(OH)₂ on carbon (50% water; 1.48 g). The mixture was placed on a Parr® shaker and then reduced (50 psi H₂) at room temperature overnight. The mixture was filtered through a pad of Celite®, and then concentrated to give a colorless solid I-1A-1 h (4.84 g, quantitative): +APcI MS (M+1) 172.2; ¹H NMR (400 MHz, CD₂Cl₂) δ 2.89 (ddd, J=12.9, 8.7, 3.3 Hz, 2H), 2.75 (ddd, J=12.9, 6.6, 3.7 Hz, 2H), 2.45 (q, J=7.2 Hz, 2H), 1.95 (ddd, J=13.7, 8.3, 3.7 Hz, 2H), 1.55 (ddd, J=13.7, 6.6, 3.3 Hz, 2 h), 1.08 (t, J=7.1 Hz, 3H).

Preparation of Intermediate 1-[7-(2-Chlorophenyl)-
8-iodo-2-methylpyrazolo[1,5-a][1,3,5]triazin-4-yl]-
4-ethylaminopiperidine-4-carboxylic Acid Amide
(I-1A-1i)

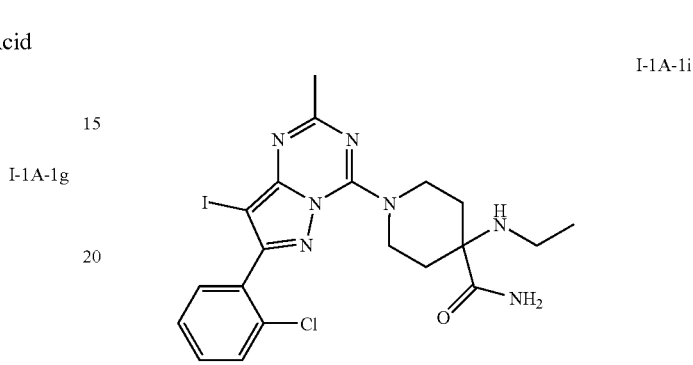

I-1A-1i

To a solution of 4-chloro-7-(2-chlorophenyl)-8-iodo-2-methylpyrazolo[1,5-a][1,3,5]triazine (I-1A-1e; 28 mg, 0.069 mmol) and triethylamine (14 µl, 0.10 mmol) in tetrahydrofuran (1 ml) was added 4-ethylaminopiperidine-4-carboxylic acid amide (I-1A-1h; 13 mg, 0.076 mmol) and the mixture was stirred overnight. The mixture was extracted from water with ethyl acetate, the combined organic layers were washed with brine, dried (MgSO₄), filtered through a 0.45 µm filter disk, and then concentrated, in vacuo, to afford the crude product (50 mg). Purification on a Chromatotron using 0-20-30% acetonitrile in methylene chloride as eluant afforded product I-1A-1i (20 mg, 54%): +APcI MS (M+1) 540.8; ¹H NMR (400 MHz, CD₂Cl₂) δ 7.54 (d, J=7.9 Hz, 1H), 7.47-7.38 (m, 3H), 4.83-4.65 (br m, 2H), 4.20-4.05 (br m, 2H), 2.55 (q, J=7.1 Hz, 2H), 2.50 (s, 3H), 2.26-1.98 (m, 2H), 1.78-1.75 (m, 2H), 1.10 (t, J=7.1 Hz, 3H).

Preparation of Intermediate 7-(2-Chlorophenyl)-8-
(4-chlorophenyl)-2-methyl-3H-pyrazolo[1,5-a][1,3,
5]triazin-4-one (I-2A-1a)

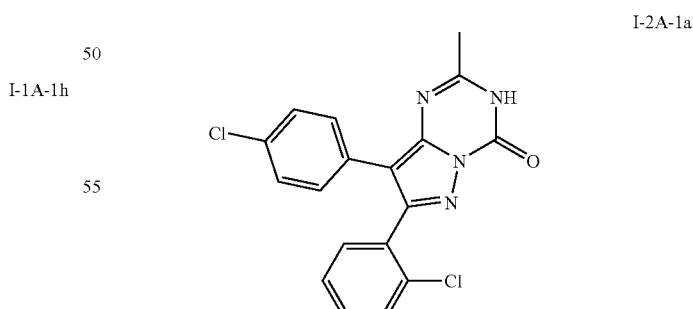

I-2A-1a

To a mixture of 7-(2-chlorophenyl)-8-iodo-2-methyl-3H-pyrazolo-[1,5-a][1,3,5]triazin-4-one (I-1A-1d; 141 g, 364 mmol) and 4-chlorophenylboronic acid (85.1 g, 544 mmol) in dimethoxyethane (1.4 L) was added 2 M aqueous Na₂CO₃ (365 ml) and then (1,1'-bis(diphenylphosphino)ferrocene)-dichloropalladium(II), dichloromethane complex (5.80 g, 7.17 mmol). The reaction was heated at reflux for 16 hours, cooled, and the organic layer separated and then concentrated under reduced pressure. The residue was dissolved in methyltetrahydrofuran (1.4 L) and washed with 1 M aqueous NaOH (2×700 ml) and 1 M aqueous HCl (700 ml). The solvent was removed, in vacuo, to give a brown solid which was suspendend in methanol (1.2 L). The mixture was concentrated to one-third volume, the solids were collected by vacuum filtration in a course sintered glass funnel, washed with methanol (1 L) and then dried, in vacuo, to afford product I-2A-1a as a light-brown solid (103 g, 76%): +APcI MS (M+1) 371.3; $^1$H NMR (400 MHz, DMSO-d$_6$) δ 12.73 (s, 1H), 7.54-7.43 (m, 4H), 7.35-7.26 (m, 4H), 2.35 (s, 3H).

Preparation of Intermediate 4-Chloro-7-(2-chlorophenyl)-8-(4-chlorophenyl)-2-methylpyrazolo[1,5-a][1,3,5]triazine (I-2A-1b)

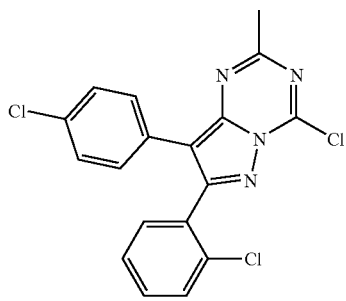

I-2A-1b

To a stirred slurry of 7-(2-chlorophenyl)-8-(4-chlorophenyl)-2-methyl-3H-pyrazolo[1,5-a][1,3,5]triazin-4-one (I-2A-1a; 30.0 g, 80.8 mmol) in toluene (400 ml) at room temperature was added diisopropylethylamine (30.3 ml, 173 mmol) and then POCl$_3$ (15.9 ml, 168 mmol) over 10 minutes. The mixture was heated at 80° C. for 5 hours, cooled to room temperature, and then slowly quenched by slow addition to half saturated brine (300 ml). The biphasic mixture was flitered through Celite® to remove the brown solids that formed on quench. The organic layer was separated and washed with saturated aqueous NaHCO$_3$ (200 ml) and then brine (200 ml). The organic solution was concentrated, in vacuo, to ½ volume and then filtered through a cotton plug. The solution was further concentrated to ¼ volume, at which point, a yellow solid began to precipitate. Hexane (300 ml) was then added and stirred for 1 hour. The solids were collected on a sintered glass funnel and dried, in vacuo, to afford the desired product I-2A-1b (22.3 g, 71%) as a dark-yellow solid: +APcI MS (M+1) 389.1; $^1$H NMR (400 MHz, CD$_2$Cl$_2$) δ 7.50-7.39 (m, 6H), 7.28 (d, J=8.7 Hz, 2H), 2.73 (s, 3H).

Preparation of Intermediate 1-Benzhydryl-3-benzylaminoazetidine-3-carbonitrile (I-2A-1c)

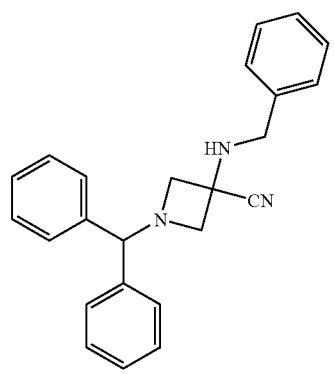

I-2A-1c

To a solution of 1-benzhydrylazetidin-3-one (3.3 g, 14 mmol) in methanol (35 ml) was added benzylamine (1.6 ml, 15 mmol) and then acetic acid (0.88 ml, 15 mmol) at room temperature. After stirring for 45 minutes, solid NaCN (0.76 g, 15 mmol) was added in portions over 2 minutes and the mixture was heated to reflux overnight. The reaction, which now contained a precipitate, was cooled and then stirred at room temperature. The solids were collected by vacuum filtration, rinsed with a small volume of cold methanol, and then dried, in vacuo, to give I-2A-1c as a solid (3.56 g, 72%): +APcI MS (M+1) 354.4; $^1$H NMR (400 MHz, CD$_3$OD) δ 7.40 (d, J=7.5 Hz, 4H), 7.35 (d, J=7.5 Hz, 2H), 7.31-7.20 (m, 7H), 7.16 (t, J=7.3 Hz, 2H), 4.44 (s, 1H), 3.76 (s, 2H), 3.48 (d, J=8.3 Hz, 2H), 3.05 (d, J=8.3 Hz, 2H).

Preparation of Intermediate 1-Benzhydryl-3-benzylaminoazetidine-3-carboxylic Acid Amide (I-2A-1d)

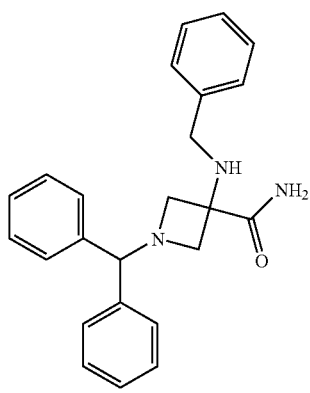

I-2A-1d

A solution of 1-benzhydryl-3-benzylaminoazetidine-3-carbonitrile I-2A-1c (3.45 g, 9.76 mmol) in methylene chloride (55 ml) cooled in an ice bath was treated with H$_2$SO$_4$ (8.1 ml, 0.15 mol), dropwise. After the reaction mixture was allowed to warm to room temperature and stir overnight, it was cooled in an ice bath and then carefully quenched with concentrated NH$_4$OH to pH 10. The mixture was extracted with methylene chloride; the combined organic layers were washed with brine, dried (Na$_2$SO$_4$) and then concentrated, in vacuo, to afford a brown solid. Trituration of this material from hexanes/diethyl ether afforded a light tan solid which was collected by vacuum filtration, washed with additional hexanes and dried, in vacuo, to give I-2A-1d (3.34 g, 92%): +ESI MS (M+1) 372.4; $^1$H NMR (400 MHz, CD$_3$OD) δ 7.41 (d, J=7.5 Hz, 4H), 7.35 (d, J=7.5 Hz, 2H), 7.31-7.22 (m, 7H), 7.16 (t, J=7.7 Hz, 2H), 4.50 (s, 1H), 3.60 (s, 2H), 3.48 (d, J=8.3 Hz, 2H), 3.16 (d, J=8.3 Hz, 2H).

Preparation of Intermediate 1-Benzhydryl-3-(benzylethylamino)-azetidine-3-carboxylic Acid Amide, Hydrochloride Salt (I-2A-1e)

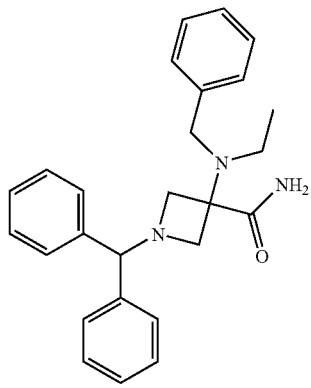

I-2A-1e

A suspension of 1-benzhydryl-3-benzylaminoazetidine-3-carboxylic acid amide I-2A-1d (3.06 g, 8.24 mmol) in methanol (80 ml) cooled in an ice bath was treated with acetic acid (2.4 ml, 41 mmol), sodium acetate (6.8 g, 82 mmol) and acetaldehyde (1.8 ml, 41 mmol). After stirring for 10 minutes, NaCNBH$_3$ (6.24 mg, 9.9 mmol) was added, portionwise. After stirring for 45 minutes, the mixture was allowed to warm to room temperature and stir overnight. The reaction was concentrated, in vacuo, and the residue then extracted from saturated aqueous sodium bicarbonate with ethyl acetate, the combined organic layers were washed with brine, dried (MgSO$_4$), and then concentrated, in vacuo, to afford the crude free-base of the product (3.8 g): +APcI MS (M+1) 400.5; $^1$H NMR (400 MHz, CD$_2$Cl$_2$) δ 7.41-7.37 (m, 6H), 7.29-7.22 (m, 6H), 7.20-7.12 (m, 3H), 4.44 (s, 1H), 3.74 (s, 2H), 3.47 (d, J=8.3 Hz, 2H), 3.12 (d, J=8.3 Hz, 2H), 2.56 (q, J=7.2 Hz, 2H), 0.85 (t, J=7.1 Hz, 3H).

For purification, a solution of the free base in methanol (75 ml) was treated with 1M HCl in diethyl ether (21 ml), dropwise over 5 minutes. After stirring for 20 minutes, the mixture was concentrated under reduced pressure followed by concentration from additional methanol (2x) and then ethanol. The residue was then suspended and stirred in isopropanol (3 ml) while diethyl ether (50 ml) was slowly added. After stirring for 45 minutes, the solids were isolated by vacuum filtration, washed with ether and then dried, in vacuo, to provide I-2A-1 e (4.4 g, quantitative): +APcI MS (M+1) 400.5; $^1$H NMR (400 MHz, CD$_3$OD) δ 7.55-7.25 (br m, 15H), 5.76 (br s, 1H), 4.21 (br s, 4H), 3.93 (v br s, 2H), 1.02 (br s, 3H).

Preparation of Intermediate 1-Benzhydryl-3-ethylaminoazetidine-3-carboxylic Acid Amide (I-2A-1f)

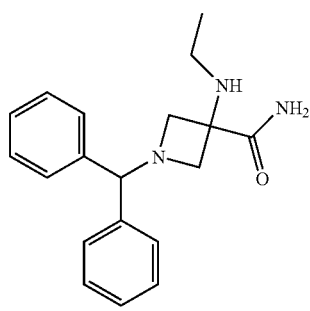

I-2A-1f

Oxalyl chloride (145.2 g, 1.121 mol) was added to dichloromethane (3.75 liters) and the resulting solution was cooled to −78° C. Dimethyl sulfoxide (179.1 g, 2.269 mol) was then added over a duration of 20 minutes (maintained internal temperature below −70° C. during addition). 1-Benzhydryl-azetidin-3-ol (250.0 g, 1.045 mol) was then added as a solution in dichloromethane (1.25 liter) to −78° C. solution over a duration of 40 minutes (maintained internal temperature below −70° C. during addition). The solution was stirred for 1 hour at −78° C. followed by the addition of triethylamine (427.1 g, 4.179 mol) over 30 minutes (maintained internal temperature below −70° C. during addition). The reaction was then allowed to come to room temperature slowly and stir for 20 hours. Aqueous 1.0 M hydrochloric acid (3.2 liters, 3.2 mol) was added to the crude reaction solution over 30 minutes, followed by stirring for 10 minutes at room temperature. The heavy dichloromethane layer (clear yellow in color) was then separated and discarded. The remaining acidic aqueous phase (clear, colorless) was treated with 50% sodium hydroxide (150 ml, 2.1 mol) with stirring over a 30 minute period. The final aqueous solution had a pH=9. At this pH the desired product precipitates from solution as a colorless solid. The pH=9 solution was stirred for 30 minutes and then the precipitated product was collected by filtration. The collected solid was washed with 1.0 liter of water and then air dried for 36 hours to give 1-benzhydrylazetidin-3-one (184.1 g, 74%) as an off-white solid: +ESI MS (M+1 of hydrated ketone) 256.3; $^1$H NMR (400 MHz, CD$_2$Cl$_2$) δ 7.47-7.49 (m, 4H), 7.27-7.30 (m, 4H), 7.18-7.22 (m, 2H), 4.60 (s, 1H), 3.97 (s, 4H).

To a solution of 1-benzhydrylazetidin-3-one (53.4 g, 225 mmol) in methanol (750 ml) was added ethylamine hydrochloride (20.2 g, 243 mmol), KCN (15.4 g, 229 mmol) and then acetic acid (14.3 ml, 247 mmol) at room temperature. After stirring for 2.5 hours at room temperature, at which point the starting ketone had been consumed, the mixture was heated at 55° C. for 15 hours. After cooling the reaction to 50° C., the reaction was treated with dimethyl sulfoxide (19.2 ml, 270 mmol) and then 2N aqueous NaOH (251 ml) over a 10-minute period. A solution of 11% aqueous peroxide (80 ml, 247 mmol) was added over 5 minutes (exothermic reaction), during which time a precipitate formed. Additional water (270 ml) was added to aid stirring. After cooling to room temperature and stirring for an additional hour, the solids were collected on a sintered funnel, washed with water, and then dried, in vacuo, to give crude I-2A-1f (55.3 g, 79%) as a solid.

For purification purposes, crude 1-benzhydryl-3-ethylaminoazetidine-3-carboxylic acid amide (I-2A-1f; 83.0 g, 268 mmol) was added to 1 M HCl (1.3 l), portionwise. After washing the solution with methylene chloride (1 l, then 0.8 l), the mixture was treated with 50% aqueous NaOH (130 ml) to bring the pH=10. The precipitate that formed on basification were collected on a sintered funnel, washed with water, and then dried, in vacuo, to give I-2A-1f (72.9 g, 88%) as a colorless solid: +ESI MS (M+1) 310.5; ¹H NMR (400 MHz, CD₃OD) δ 7.41 (d, J=7.1 Hz, 4H), 7.25 (t, J=7.5 Hz, 4H), 7.16 (t, J=7.5 Hz, 2H), 4.49 (s, 1H), 3.44 (d, J=8.3 Hz, 2H), 3.11 (d, J=8.3 Hz, 2H), 2.47 (q, J=7.1 Hz, 2H), 1.10 (t, J=7.3 Hz, 3H).

Preparation of Intermediate 3-Ethylaminoazetidine-3-carboxylic Acid Amide, Hydrochloride Salt (I-2A-1g)

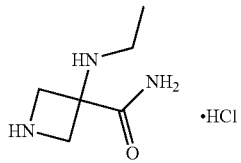

I-2A-1g

To a solution of 1-benzhydryl-3-(benzylethylamino)-azetidine-3-carboxylic acid amide hydrochloride salt (I-2A-1e; 0.66 g, 1.4 mmol) in methanol (25 ml) was added 20% Pd(OH)₂ on carbon (30% water; 0.13 g). The mixture was placed on a Parr® shaker and then reduced (45 psi H₂) at room temperature overnight. The mixture was diluted with methanol (200 ml) filtered through a 0.45 µm filter disk, and then concentrated to a solid. The residue was triturated from diethyl ether, collected by vacuum filtration, washed with diethyl ether and then dried, in vacuo, to afford I-2A-1g (298 mg, 98%): +APcI MS (M+1) 144.1; ¹H NMR (400 MHz, CD₂Cl₂) δ 4.56 (br s, 4H), 3.00 (q, J=7.2 Hz, 2H), 1.36 (t, J=7.1 Hz, 3H).

Alternate Preparation of Intermediate 3-Ethylaminoazetidine-3-carboxylic Acid Amide, Hydrochloride Salt (I-2A-1g)

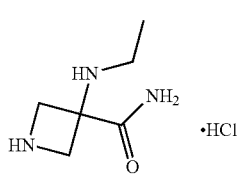

I-2A-1g

To a suspention of 1-benzhydryl-3-ethylaminoazetidine-3-carboxylic acid amide (I-2A-1f; 36.1 g, 117 mmol) in methanol (560 ml) at room temperature was added concentrated aqueous HCl (19.5 ml, 234 mmol), resulting in a clear solution. To 20% Pd(OH)₂ on carbon (3.75 g) was added methanol (85 ml), followed by the methanolic solution of I-2A-1f. The mixture was placed on a Parr® shaker and then reduced (50 psi H₂) at room temperature for 20 hours. The reaction was then filtered through Celite® and then concentrated to low volume under reduced pressure, at which point a precipitate formed. The suspension was diluted with MTBE (500 ml), stirred for an additional hour, and the precipitate collected by vacuum filtration. The solid was washed washed with MTBE and then dried, in vacuo, to afford I-2A-1g (24.8 g, 98%) as a colorless solid.

Preparation of Intermediate 1-Benzhydryl-3-isopropylaminoazetidine-3-carbonitrile (I-3A-1a)

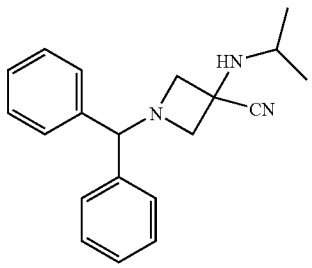

I-3A-1a

To a solution of 1-benzhydrylazetidin-3-one (3.20 g, 13.5 mmol) in ethanol (100 ml) cooled in an ice bath was added isopropylamine (1.26 ml, 14.8 mmol), followed by dropwise addition of concentrated aqueous HCl (1.23 ml, 14.8 mmol). After stirring for 15 minutes, a solution of NaCN (0.727 g, 14.8 mmol) in water (30 ml) was added to the reaction mixture over 7 minutes. The reaction was then warmed to room temperature and stirred overnight. After concentrating the reaction to half volume, in vacuo, it was extracted from saturated aqueous sodium bicarbonate with ethyl acetate. The combined organic layers were washed with brine, dried (Na₂SO₄), filtered and concentrated, in vacuo, to give an oil (3.17 g) that was 2:1 cyanohydrin to ketone as judged by ¹H NMR and LCMS. A solution of the residue in methanol (17 ml) was treated with isopropylamine (2.3 mmol, 27 mmol) and then acetic acid (1.6 ml, 27 mmol) at room temperature. After stirring for 30 minutes, solid NaCN (330 mg, 6.7 mmol) was added and the mixture was heated to reflux overnight. The reaction was concentrated, in vacuo, and then extracted from saturated aqueous sodium bicarbonate with ethyl acetate. The combined organic layers were washed with brine, dried (Na₂SO₄), filtered and concentrated, in vacuo, to give I-3A-1a as a dark foam (3.41 g, 83%): +APcI MS (M+1) 306.4; ¹H NMR (400 MHz, CD₂Cl₂) δ 7.45-7.42 (m, 4H), 7.31-7.18 (m, 6H), 4.42 (s, 1H), 3.68 (d, J=8.3 Hz, 2H), 3.11 (septuplet, J=6.2 Hz, 1H), 3.07 (d, J=8.3 Hz, 2H), 1.01 (d, J=6.2 Hz, 6H).

Preparation of Intermediate 1-Benzhydryl-3-isopropylaminoazetidine-3-carboxylic Acid Amide (I-3A-1b)

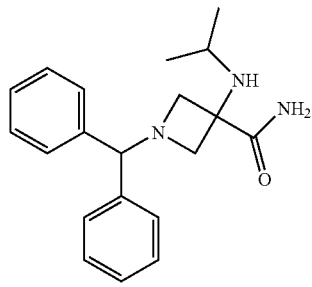

I-3A-1b

A solution of 1-benzhydryl-3-isopropylaminoazetidine-3-carbonitrile (I-3A-1a; 3.40 g, 11.1 mmol) in methylene chloride (25 ml) cooled in an ice bath was treated with $H_2SO_4$ (5.95 ml, 111 mmol), dropwise. After the reaction mixture was allowed to warm to room temperature and stir overnight, it was cooled in an ice bath and then carefully quenched with concentrated $NH_4OH$ to pH 11. The mixture was extracted with methylene chloride, the combined organic layers were dried ($Na_2SO_4$) and then concentrated, in vacuo, to afford a crude foam (3.3 g) that was then purified on a Biotage™ Flash 40M column using 0-2% methanol in methylene chloride as eluant to afford the title compound I-3A-1b (2.32 g, 64%) as a brown solid: +ESI MS (M+1) 324.4; $^1$H NMR (400 MHz, $CD_3OD$) δ 7.40 (d, J=7.5 Hz, 4H), 7.24 (t, J=7.5 Hz, 4H), 7.15 (t, J=7.1 Hz, 2H), 4.46 (s, 1H), 3.53 (d, J=8.7 Hz, 2H), 3.06 (d, J=8.7 Hz, 2H), 2.90 (septuplet, J=6.4 Hz, 1H), 0.97 (d, J=6.6 Hz, 6H).

Preparation of Intermediate 3-Isopropylaminoazetidine-3-carboxylic Acid Amide, Hydrochloride Salt (I-3A-1c)

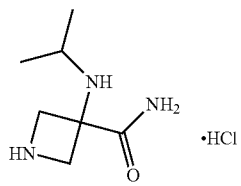

I-3A-1c

To a solution of 1-benzhydryl-3-isopropylaminoazetidine-3-carboxylic acid amide (I-3A-1b; 2.28 g, 7.05 mmol) in methanol (100 ml) was added 1M HCl in ether (14.8 ml, 14.8 mmol) and then water (10 ml). After the addition of 20% $Pd(OH)_2$ on carbon (60% water; 1.43 g), the mixture was placed on a Parr® shaker and then reduced (50 psi $H_2$) at room temperature overnight. The mixture was filtered through a pad of Celite®, and then concentrated, in vacuo. The residue was then concentrated, in vacuo, from toluene (2×), acetonitrile (2×) and then methanol to give I-3A-1c (1.59 g, 98%) as a tan solid: +APcI MS (M+1) 158.1; $^1$H NMR (400 MHz, $CD_3OD$) δ 4.71 (d, J=13.3 Hz, 2H), 4.60 (d, J=13.3 Hz, 2H), 3.49 (septuplet, J=6.6 Hz, 1H), 1.34 (d, J=6.6 Hz, 6H).

Preparation of Intermediate 1-Benzhydryl-3-methylaminoazetidine-3-carbonitrile (I-3A-2a)

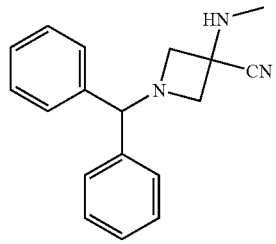

I-3A-2a

To a solution of 1-benzhydrylazetidin-3-one (2.13 g, 8.98 mmol) in methanol (17 ml) was added methylamine hydrochloride (1.21 g, 18.0 mmol) and then acetic acid (1.03 ml, 18.0 mmol) at room temperature. After stirring for 5 minutes, solid KCN (1.17 g, 18.0 mmol) was added and the mixture was heated to 60° C. for 19 hours. The reaction was cooled; the solid product was collected by vacuum filtration, rinsed with methanol, and then dried, in vacuo, to afford I-3A-2a as a colorless solid (2.50 g, quantitative): +ESI MS (M+1) 278.3; $^1$H NMR (400 MHz, $CD_2Cl_2$) δ 7.43 (d, J=7.5 Hz, 4H), 7.29 (t, J=7.5 Hz, 4H), 7.23 (t, J=7.3 Hz, 2H), 4.45 (s, 1H), 3.55 (d, J=7.5 Hz, 2H), 3.15 (d, J=7.1 Hz, 2H), 2.40 (s, 3H).

Preparation of Intermediate 1-Benzhydryl-3-methylaminoazetidine-3-carboxylic Acid Amide (I-3A-2b)

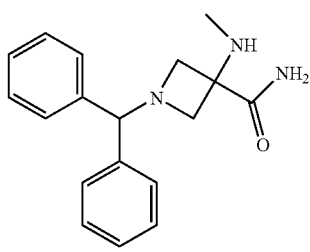

I-3A-2b

A vigorously stirred solution of 1-benzhydryl-3-methylaminoazetidine-3-carbonitrile (I-3A-2a; 2.10 g, 7.57 mmol) in methylene chloride (25 ml) cooled in an ice bath was treated with $H_2SO_4$ (4.0 ml, 76 mmol), dropwise. After the reaction mixture was allowed to warm to room temperature and stir overnight, it was cooled in an ice bath and then carefully quenched with concentrated $NH_4OH$ to pH 11. The mixture was extracted with methylene chloride, the combined organic layers were dried ($Na_2SO_4$) and then concentrated, in vacuo, to afford I-3A-2b (1.2 g, 54%) as an off-white solid: +ESI MS (M+1) 296.3; $^1$H NMR (400 MHz, $CD_3OD$) δ 7.41 (d, J=7.5 Hz, 4H), 7.25 (t, J=7.5 Hz, 4H), 7.16 (t, J=7.1 Hz, 2H), 4.48 (s, 1H), 3.41 (d, J=8.7 Hz, 2H), 3.09 (d, J=8.7 Hz, 2H), 2.24 (s, 3H).

Preparation of Intermediate 3-Methylaminoazetidine-3-carboxylic Acid Amide, Hydrochloride Salt (I-3A-2c)

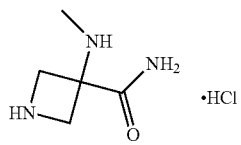

I-3A-2c

To a suspension of 1-benzhydryl-3-methylaminoazetidine-3-carboxylic acid amide (I-3A-2b; 13.5 g, 45.8 mmol) in methanol (90 ml) was added concentrated aqueous HCl (8.0 ml, 96 mol), dropwise, to give a homogeneous solution. After the addition of 20% Pd(OH)$_2$ on carbon (50% water; 4.1 g), the mixture was placed on a Parr® shaker and then reduced (50 psi H$_2$) at room temperature for 7 hours. The mixture was filtered through a pad of Celite®, washing with copious amount of 9:1 methanol/water, and then 9:1 tetrahydrofuran/water until no product eluted (determined with ninhydrin stain). The filtrate was then concentrated, in vacuo, and the residue was then triturated from diethyl ether to give I-3A-2c (9.3 g, quantitative) as a brown solid: +APcI MS (M+1) 129.9; $^1$H NMR (400 MHz, CD$_3$OD) δ 4.50 (d, J=12.0 Hz, 2H), 4.43 (d, J=12.9 Hz, 2H), 2.64 (s, 3H).

Preparation of Intermediate 1-Benzhydryl-3-dimethylaminoazetidine-3-carbonitrile (I-3A-3a)

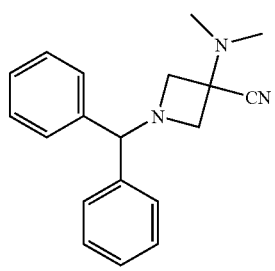

I-3A-3a

A solution of 2M dimethylamine in THF (3.92 ml, 7.83 mmol) was added to 1-benzhydrylazetidin-3-one (1.43 g, 6.03 mmol). After stirring 5 minutes, acetic acid (0.450 ml, 7.83 mmol), solid KCN (0.510 g, 7.83 mmol), and methanol (0.5 ml) were added at room temperature. After stirring for 5 minutes, the mixture was heated to 60° C. for 19 hours. The reaction was cooled and extracted from saturated aqueous NaHCO$_3$ with ethyl acetate. The combined extracts were dried (Na$_2$SO$_4$), and concentrated, in vacuo, to afford I-3A-3a as a foam (1.77 g, quantitative): +ESI MS (M+1) 292.3; $^1$H NMR (400 MHz, CD$_2$Cl$_2$) δ 7.44 (d, J=7.5 Hz, 4H), 7.29 (t, J=7.5 Hz, 4H), 7.21 (t, J=7.3 Hz, 2H), 4.41 (s, 1H), 3.58 (d, J=8.3 Hz, 2H), 3.05 (d, J=8.3 Hz, 2H), 2.13 (s, 6H).

Preparation of Intermediate 1-Benzhydryl-3-dimethylaminoazetidine-3-carboxylic Acid Amide (I-3A-3b)

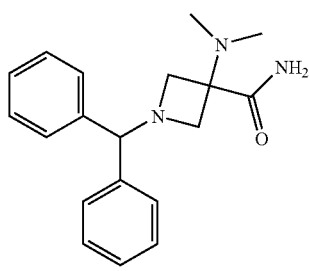

I-3A-3b

A vigorously stirred solution of 1-benzhydryl-3-dimethylaminoazetidine-3-carbonitrile (I-3A-3a; 1.55 g, 5.32 mmol) in methylene chloride (30 ml) cooled in an ice bath was treated with H$_2$SO$_4$ (3.0 ml, 54 mmol), dropwise. After warming to room temperature and stirring overnight, the reaction was cooled in an ice bath and then carefully quenched with concentrated aqueous NH$_4$OH to pH 11. The mixture was extracted with methylene chloride. The combined organic layers were dried (Na$_2$SO$_4$) and then concentrated. The crude product (4:1 product to starting material) was then purified on a Biotage™ Flash 40M column using 3% methanol in methylene chloride as eluant. The residue (1.04 g) was then triturated from ether to afford I-3A-3b (0.75 g, 45%): +ESI MS (M+1) 310.3; $^1$H NMR (400 MHz, CD$_3$OD) δ 7.40 (d, J=7.5 Hz, 4H), 7.24 (t, J=7.5 Hz, 4H), 7.17 (t, J=7.3 Hz, 2H), 4.42 (s, 1H), 3.41 (d, J=8.7 Hz, 2H), 3.12 (d, J=8.7 Hz, 2H), 2.26 (s, 6H).

Preparation of Intermediate 3-Diethylaminoazetidine-3-carboxylic Acid Amide, Hydrochloride Salt (I-3A-3c)

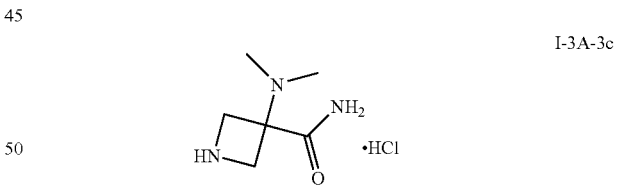

I-3A-3c

To a solution of 1-benzhydryl-3-dimethylaminoazetidine-3-carboxylic acid amide (I-3A-3b; 730 mg, 2.36 mmol) in methanol/methylene chloride was added excess 1 M HCl in diethyl ether (5.0 ml). The solvent was removed, in vacuo, and the resultant hydrochloride salt dissolved in methanol (30 ml). After the addition of 20% Pd(OH)$_2$ on carbon (50% water; 365 mg), the mixture was placed on a Parr® shaker and then reduced (50 psi H$_2$) at room temperature for 5 hours. The reaction was filtered through a 0.45 μM disk, and then concentrated, in vacuo, to give I-3A-3c (224 mg, 44%) as an off-white solid: +APcI MS (M+1) 144.0; $^1$H NMR (400 MHz, CD$_3$OD) δ 4.52 (d, J=12.5 Hz, 2H), 4.39 (d, J=12.9 Hz, 2H), 2.70 (s, 6H).

Preparation of Intermediate 2-Benzhydryl-5-methyl-2,5,7-triazaspiro[3.4]oct-6-en-8-one (I-3A-4a)

Preparation of Intermediate 2-Benzhydryl-5-benzyl-2,5,7-triazaspiro[3.4]oct-6-en-8-one (I-3A-5a)

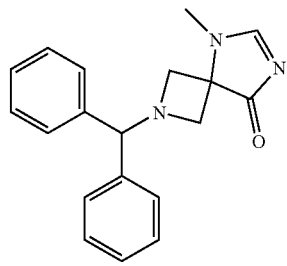

I-3A-4a

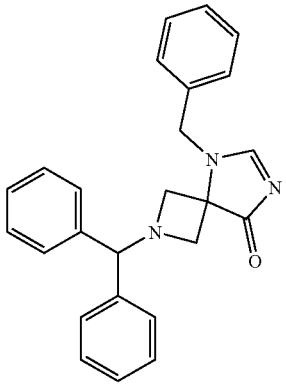

I-3A-5a

N,N-Dimethylformamide dimethyl acetal (1.1 ml, 8.3 mmol) was combined with 1-benzhydryl-3-methylaminoazetidine-3-carboxylic acid amide (I-3A-2b; 153 mg, 0.52 mmol) and heated to reflux. After 3 hours, the suspension was cooled and extracted from saturated aqueous NaHCO$_3$ with ethyl acetate. The combined extracts were dried (Na$_2$SO$_4$), and concentrated, in vacuo, to afford I-3A-4a as a solid (152 mg, 96%): +ESI MS (M+1) 306.3; $^1$H NMR (400 MHz, CD$_3$OD) δ 8.42 (s, 1H), 7.47 (d, J=7.5 Hz, 4H), 7.27 (t, J=7.5 Hz, 4H), 7.17 (t, J=7.5 Hz, 2H), 4.57 (s, 1H), 3.58 (s, 3H), 3.55 (d, J=10.0 Hz, 2H), 3.34 (d, J=10.0 Hz, 2H).

Preparation of Intermediate
5-Methyl-2,5,7-triazaspiro[3.4]octan-8-one, Hydrochloride Salt (I-3A-4b)

N,N-Dimethylformamide dimethyl acetal (16 ml, 121 mmol) was combined with 1-benzhydryl-3-benzylaminoazetidine-3-carboxylic acid amide (I-2A-1d; 3.03 g, 8.16 mmol) and heated to reflux. After 4 hours, the suspension was cooled and extracted from saturated aqueous NaHCO$_3$ with ethyl acetate. The combined extracts were dried (Na$_2$SO$_4$), and concentrated, in vacuo, to the crude solid (3.50 g). Purification of the residue on a Biotage™ Flash 40M column using 0-3% methanol in methylene chloride as eluant afforded I-3A-5a as a yellowish solid (1.92 g, 62%): +ESI MS (M+1) 382.3; $^1$H NMR (400 MHz, CD$_3$OD) δ 8.66 (s, 1H), 7.59 (d, J=7.1 Hz, 2H), 7.49-7.11 (m, 13H), 5.12 (s, 2H), 4.44 (s, 1H), 3.31 (d, J=9.6 Hz, 2H), 3.20 (d, J=9.6 Hz, 2H).

Preparation of Intermediate
2,5,7-Triazaspiro[3.4]octan-8-one, Hydrochloride Salt (I-3A-5b)

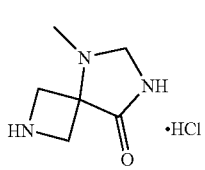

I-3A-4b

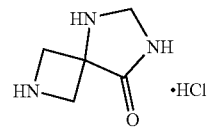

I-3A-5b

To a solution of 2-benzhydryl-5-methyl-2,5,7-triazaspiro[3.4]oct-6-en-8-one (I-3A-4a; 189 mg, 0.619 mmol) in methanol (30 ml) was added 1 M HCl in diethyl ether (1.3 ml). After the addition of 20% Pd(OH)$_2$ on carbon (50% water; 95 mg), the mixture was placed on a Parr® shaker and then reduced (50 psi H$_2$) at room temperature for 5 hours. The reaction was filtered through a 0.45 μM disk, and then concentrated, in vacuo, to give a solid. Trituration from diethyl ether afforded I-3A-4b (124 mg, 94%) as an off-white solid: +APcI MS (M+1) 142.0; $^1$H NMR (400 MHz, CD$_3$OD) δ 4.38 (d, J=12.0 Hz, 2H), 4.17 (s, 2H), 4.13 (d, J=12.5 Hz, 2H), 2.71 (s, 3H).

To a solution of 2-benzhydryl-5-benzyl-2,5,7-triazaspiro [3.4]oct-6-en-8-one (I-3A-5a; 1.83 g, 4.80 mmol) in methanol/methylene chloride was added excess 1 M HCl in diethyl ether (10 ml). After stirring for 10 minutes, the solvent was removed, in vacuo, and the resultant hydrochloride salt dissolved in methanol (50 ml). After the addition of 20% Pd(OH)$_2$ on carbon (50% water; 1.1 g), the mixture was placed on a Parr® shaker and then reduced (50 psi H$_2$) at room temperature for 22 hours. The reaction was filtered through a 0.45 μM disk, and then concentrated, in vacuo, to give a gummy solid. This material was triturated from methanol to afford I-3A-5b (450 mg, 47%) as a tan solid: +APcI MS (M+1) 127.9; $^1$H NMR (400 MHz, CD$_3$OD) δ 4.51 (s, 2H), 4.41-4.33 (m, 4H).

Preparation of Intermediate
3-Aminoazetidine-3-carboxylic Acid Amide,
Hydrochloride Salt (I-3A-6a)

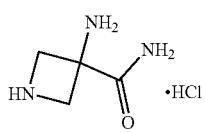

I-3A-6a

To a solution of 1-benzhydryl-3-benzylaminoazetidine-3-carboxylic acid amide (I-2A-1d; 1.83 g, 4.80 mmol) in methanol/methylene chloride was added excess 1 M HCl in diethyl ether (3.5 ml). After stirring for 10 minutes, the solvent was removed, in vacuo, and the resultant hydrochloride salt dissolved in 10:1 methanol/water (55 ml). After the addition of 20% Pd(OH)$_2$ on carbon (50% water; 0.37 g), the mixture was placed on a Parr®) shaker and then reduced (50 psi H$_2$) at room temperature for 23 hours. The reaction was diluted with methanol (50 ml), filtered through a 0.45 μM disk, and the disk rinsed with methanol (2×100 ml). The combined methanolic solutions were concentrated, in vacuo, and then triturated from diethyl ether to afford I-3A-6a (262 mg, 85%) as a tan solid: +APcI MS (M+1) 115.8; $^1$H NMR (400 MHz, CD$_3$OD) δ 4.58 (d, J=13.3 Hz, 2H), 4.47 (d, J=13.3 Hz, 2H).

Preparation of Intermediate 5-(2-Chlorophenyl)-2H-pyrazol-3-ylamine (I-3A-9a)

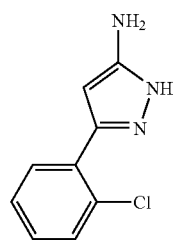

I-3A-9a

A solution of 2-chlorobenzoylacetonitrile (15.9 g, 89 mmol) and hydrazine hydrate (8.9 g, 0.18 mol) in ethanol (2 ml) was heated at reflux for 22 hr. After cooling to room temperature, the reaction was concentrated, in vacuo. The residue was dissolved in ethyl acetate, washed with water and brine, dried (MgSO$_4$), and concentrated, in vacuo, to a brown oil. Flash chromatography using 10% ethyl acetate in methylene chloride, changing to 5% methanol in methylene chloride as eluant afforded title product I-3A-9a (17.3 g, quantitative): +ESI MS (M+1) 194.2; $^1$H NMR (400 MHz, CD$_3$OD) δ 7.60-7.25 (m, 4H), 5.99 (br s, 1H).

Preparation of Intermediate N-[5-(2-Chlorophenyl)-2H-pyrazol-3-yl]-formamidine, Acetate Salt (I-3A-9b)

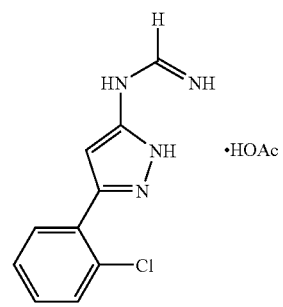

I-3A-9b

To a vigorously stirred solution of saturated aqueous Na$_2$CO$_3$ (50 mL) and methylene chloride (50 ml) was added solid ethylformimidate hydrochloride salt (8.98 g, 82 mol). After stirring for several minutes the aqueous layer was separated and extracted with additional methylene chloride (3×50 ml). The combined organic layers were dried (MgSO$_4$) and filtered. To the stirred solution was added 5-(2-chlorophenyl)-2H-pyrazol-3-ylamine (I-3A-9a; 5.27 g, 27 mmol) in methylene chloride (50 mL) and then glacial acetic acid (2.67 ml, 46.6 mmol), dropwise. A cloudy precipitate began to form as the acetic acid was added. After stirring overnight, the solids were collected by vacuum filtration, washed with methylene chloride, and then dried, in vacuo, to give intermediate I-3A-9b, contaminated with ~25% of the corresponding dimer (MW=396; 2 pyrazoles+1 formamidine), as a solid (5.7 g, 75%): +APcI MS (M+1) 221.1; $^1$H NMR (400 MHz, CD$_3$OD) δ 8.02 (s, 1H), 7.62-7.30 (m, 4H), 6.48 (s, 1H), 1.92 (s, 3H).

Preparation of Intermediate 7-(2-Chlorophenyl)-3H-pyrazolo[1,5-a][1,3,5]-triazin-4-one (I-3A-9c)

I-3A-9c

To an ethanolic solution of sodium ethoxide, generated by portionwise addition of sodium metal (4.2 g, 185 mmol) to stirred ethanol (250 ml), was added N-[5-(2-chlorophenyl)-2H-pyrazol-3-yl]-formamidine, acetate salt (I-3A-9b; 5.2 g, 18.5 mmol) in one portion. Diethylcarbonate (17.8 ml, 148 mmol) was added, dropwise, and the mixture was heated at reflux for 2 hours. After cooling to room temperature, the reaction was concentrated, in vacuo, and then extracted with ethyl acetate from water after adjusting to pH 7 with 3 M aqueous HCL. The combined organic layers were washed with water and then brine, dried (MgSO$_4$), filtered, and then concentrated, in vacuo, to one-third volume at which time a precipitate began to form. After stirring overnight, the product was collected by vacuum filtration and then dried, in vacuo, to afford I-3A-9c as a solid (2.61 g, 57%). A second crop of the intermediate was collected from the filtrate after standing an additional 24 hours (600 mg, 19%): +ESI MS (M+1) 247.1; $^1$H NMR (400 MHz, CD$_3$OD) δ 7.97 (s, 1H), 7.86-7.82 (m, 1H), 7.55-7.51 (m, 1H), 7.45-7.39 (m, 2H), 6.92 (s, 1H).

Preparation of Intermediate 7-(2-Chlorophenyl)-8-iodo-3H-pyrazolo[1,5-a][1,3,5]triazin-4-one (I-3A-9d)

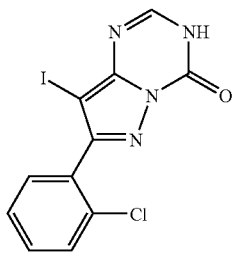

I-3A-9d

To a suspension of 7-(2-chlorophenyl)-3H-pyrazolo[1,5-a][1,3,5]-triazin-4-one (I-3A-9c; 2.59 g, 10.5 mmol) in chloroform (115 ml) cooled in an ice bath was added N-iodosuccinimide (2.36 g, 10.5 mmol), portionwise, over 15 minutes. After stirring for 3 hours, the reaction was added to stirring water and methylene chloride. A solution of saturated aqueous Na$_2$S$_2$O$_4$ was added until the color remained light yellow. The solid precipitate that was dispersed in the aqueous phase was collected by vacuum filtration and then dried, in vacuo, to afford intermediate I-3A-9d as a solid (3.78 g, 97%): +APcI MS (M+1) 372.9; $^1$H NMR (400 MHz, CD$_3$OD) δ 8.05 (s, 1H), 7.55-7.40 (m, 4H).

Preparation of Intermediate 7-(2-Chlorophenyl)-8-(4-chlorophenyl)-3H-pyrazolo[1,5-a][1,3,5]triazin-4-one (I-3A-9e)

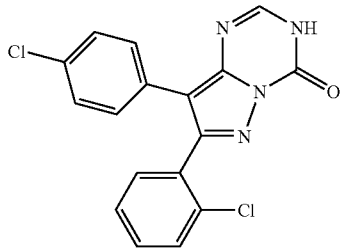

I-3A-9e

A mixture of 7-(2-chlorophenyl)-8-iodo-3H-pyrazolo[1,5-a][1,3,5]-triazin-4-one (I-3A-9d; 500 mg, 1.34 mmol), 4-chlorophenylboronic acid (315 mg, 2.01 mmol), and tetrakis(triphenylphosphine)palladium (50 mg, 0.043 mmol) under an argon atmosphere in ethanol (12 ml) and 2M aqueous Na$_2$CO$_3$ (2.5 ml) was degassed (3×) by pulling a vacuum followed by refilling with argon gas. The mixture was heated at 68° C. for 7 hours and then cooled to room temperature. The mixture was extracted from water with ethyl acetate, the combined organic layers were washed with brine, dried (MgSO$_4$), and concentrated, in vacuo, to afford a dark, viscous oil (690 mg). The product was crystallized from methanol and then collected by vacuum filtration to afford, after rinsing with methanol, intermediate I-3A-9e (218 mg, 45%) as a solid: +APcI MS (M+1) 357.0; $^1$H NMR (400 MHz, CD$_3$OD) δ 8.02 (s, 1H), 7.54-7.41 (m, 4H), 7.34 (d, J=8.7 Hz, 2H), 7.23 (d, J=8.7 Hz, 2H).

Preparation of Intermediate 4-Chloro-7-(2-chlorophenyl)-8-(4-chlorophenyl)-pyrazolo[1,5-a][1,3,5]triazine (I-3A-9f) and Di-[7-(2-chlorophenyl)-8-(4-chlorophenyl)-pyrazolo[1,5-a][1,3,5]triazin-4-yl] Ether (I-5A-1a)

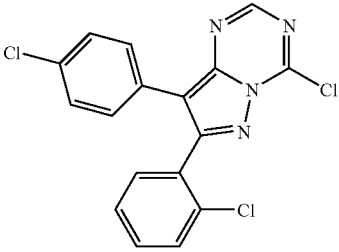

I-3A-9f

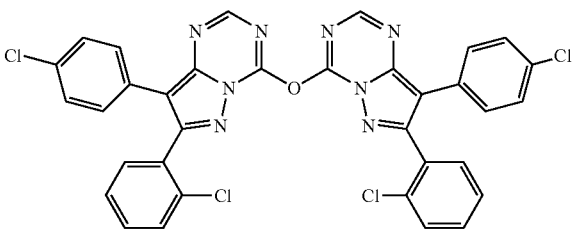

I-5A-1a

To a suspension of 7-(2-chlorophenyl)-8-(4-chlorophenyl)-3H-pyrazolo[1,5-a][1,3,5]triazin-4-one (I-3A-9e; 0.18 g, 0.51 mmol) in toluene (5 ml) was added POCl$_3$ (0.78 ml, 5.1 mmol) and then diisopropylethylamine (0.13 ml, 1.0 mmol), dropwise. The mixture was heated at 98° C. for 8 hours, cooled to room temperature, and then concentrated, in vacuo. Purification of the residue by silica gel chromatography using 30-0% hexanes in methylene chloride as eluant provided I-3A-9f (58 mg, 31%) and I-5A-1a (85 mg, 48%) as solids. I-3A-9f: +APcI MS (M+1) 375.1; $^1$H NMR (400 MHz, CD$_2$Cl$_2$) δ 8.53 (s, 1H), 7.53-7.40 (m, 6H), 7.30 (d, J=8.7 Hz, 2H). I-5A-1a: +APcI MS (M+1) 694.9; $^1$H NMR (400 MHz, CD$_2$Cl$_2$) δ 8.83 (s, 1H), 8.27 (s, 1H), 7.56-7.28 (m, 16H).

Preparation of Intermediate 1-[7-(2-Chlorophenyl)-8-iodo-2-methylpyrazolo[1,5-a][1,3,5]triazin-4-yl]-3-ethylaminoazetidine-3-carboxylic Acid Amide (I-6A-1)

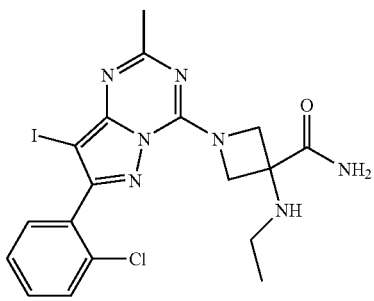

I-6A-1a

To a solution of 3-ethylaminoazetidine-3-carboxylic acid amide (I-2A-1g; 0.55 g, 2.5 mmol) and diisopropylethylamine (1.3 ml, 7.6 mmol) in DMF (10 ml) was added a solution of 4-chloro-7-(2-chlorophenyl)-8-iodo-2-methylpyrazolo[1,5-a][1,3,5]triazine (I-1A-1e; 0.93 g, 2.3 mmol) in methylene chloride (10 ml). After stirring 2 hours, the methylene chloride was removed, in vacuo, and the mixture was extracted from water, adjusted to pH 8 with saturated aqueous NaHCO$_3$, with ethyl acetate. The combined organic layers were washed with water and brine, dried (MgSO$_4$), and then concentrated, in vacuo, to afford a yellow solid. The material was then triturated from methylene chloride/methanol to afford I-6A-1a (0.73 g, 62%) as a colorless solid: +APcI MS (M+1) 512.0; $^1$H NMR (400 MHz, CDCl$_3$) δ 7.51 (d, J=7.9 Hz, 1H), 7.43-7.34 (m, 3H), 6.99 (d, J=4.7 Hz, 1H), 5.42 (d, J=4.7 Hz, 1H), 5.24 (br d, J=9.5 Hz, 1H), 4.81 (br d, J=9.5 Hz, 1H), 4.69 (br d, J=9.5 Hz, 1H), 4.13 (br d, J=9.5 Hz, 1H), 2.68-2.58 (m, 2H), 2.54 (s, 3H), 1.16 (t, J=7.0 Hz, 3H).

Example 1

Preparation of 1-[7-(2-Chlorophenyl)-8-(4-fluorophenyl)-2-methylpyrazolo[1,5-a][1,3,5]triazin-4-yl]-4-ethylaminopiperidine-4-carboxylic Acid Amide (1A-1)

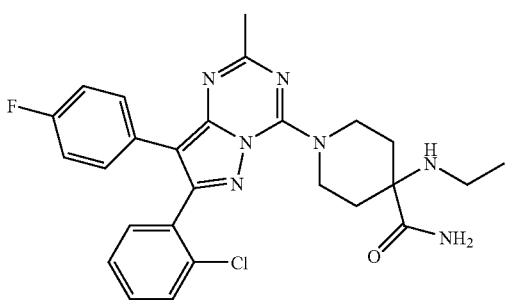

1A-1

A mixture of 1-[7-(2-chlorophenyl)-8-iodo-2-methylpyrazolo[1,5-a][1,3,5]triazin-4-yl]4-ethylaminopiperidine-4-carboxylic acid amide (I-1A-1i; 20 mg, 0.037 mmol) and 4-fluorophenylboronic acid (7.8 mg, 0.056 mmol) in ethanol (1.3 ml), toluene (1.3 ml) and 2M aqueous Na$_2$CO$_3$ (0.3 ml) was degassed (3×) by pulling a vacuum followed by refilling with nitrogen gas. Tetrakis(triphenylphosphine)palladium (6 mg, 0.005 mmol) was added and the mixture was heated at 80° C. for 5 hours. After cooling to room temperature, the mixture was extracted from water with ethyl acetate, the combined organic layers were washed with brine, dried (MgSO$_4$), filtered through a 0.45 μm filter disk, and then concentrated, in vacuo, to afford the crude product (50 mg). Purification on a Chromatotron using 0-3% methanol in methylene chloride as eluant afforded a light yellow oil, which was crystallized from diethyl ether, and dried, in vacuo, to afford 1A-1 (11 mg, 58%) as a colorless solid: +ESI MS (M+1) 508.4; $^1$H NMR (400 MHz, CD$_3$OD) δ 7.46-7.34 (m, 4H), 7.32 (dd, J=8.7, 5.4 Hz, 2H), 6.96 (t, J=8.7 Hz), 4.70-4.58 (br m, 2H), 4.40-4.25 (br m, 2H), 2.51 (q, J=7.1 Hz, 2H), 2.46 (s, 3H), 2.20-2.12 (br m, 2H), 1.83-1.75 (m, 2H), 1.10 (t, J=7.1 Hz, 3H).

The hydrochloride salt of compound 1A-1 may be prepared using the following procedure To a solution of 1-[7-(2-chlorophenyl)-8-(4-fluorophenyl)-2-methylpyrazolo[1,5-a][1,3,5]triazin-4-yl]-4-ethylaminopiperidine-4-carboxylic acid amide (1A-1; 10 mg, 0.020 mmol) in methanol (1 ml) was added 1M HCl in diethyl ether (0.050 ml). After stirring for 5 minutes, the reaction was concentrated, in vacuo, to a glassy solid that was then triturated from diethyl ether. The solid precipitate was isolated by decanting off the ether layer, washed with addition ether (3×), and then dried, in vacuo, to afford the hyrdrochloride salt of 1A-1 as an off-white solid (10 mg, 90%): +APcI MS (M+1) 508.5; $^1$H NMR (400 MHz, CD$_3$OD) δ 7.48-7.35 (m, 4H), 7.31 (dd, J=8.7, 5.4 Hz, 2H), 7.04 (t, J=8.9 Hz), 5.05-4.95 (br m, 2H), 4.35-4.23 (br m, 2H), 3.06 (q, J=7.2 Hz, 2H), 2.67-2.59 (br m, 2H), 2.56 (s, 3H), 2.22-2.14 (m, 2H), 1.35 (t, J=7.3 Hz, 3H).

The compounds listed in Table 1 below were prepared using procedures analogous to those described above for the synthesis of Compound 1A-1 using the appropriate starting materials which are available commercially, prepared using preparations well-known to those skilled in the art, or prepared in a manner analogous to routes described above for other intermediates. The compounds listed below were isolated initially as the free base and then generally converted to their corresponding hydrochloride salt for testing.

TABLE 1

| Example No. | X | —NRR' | MS (M + H)+ |
|---|---|---|---|
| 1A-2 | Cl | ![structure with piperidine-ethylamine-carboxamide] | 524.4 |
| 1A-3 | Cl | ![structure with piperidine-isopropylamine-carboxamide] | 538.3 |

Example 2

Preparation of 1-[7-(2-Chlorophenyl)-8-(4-chlorophenyl)-2-methylpyrazolo[1,5-a][1,3,5]triazin-4-yl]-3-ethylaminoazetidine-3-carboxylic Acid Amide (2A-1):

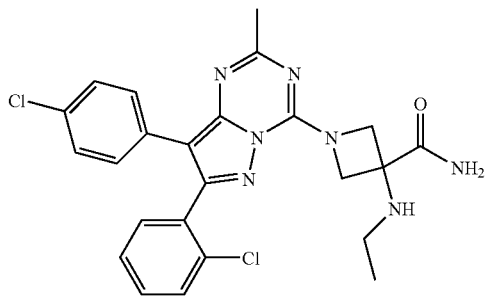

To a stirred solution of 4-chloro-7-(2-chlorophenyl)-8-(4-chlorophenyl)-2-methylpyrazolo[1,5-a][1,3,5]triazine (I-2A-1b; 2.00 g, 5.13 mmol) in DME (30 ml) at 23° C. was added diisopropylethylamine (0.940 ml, 5.36 mmol) over 5 minutes. In a separate flask, a solution of 3-ethylaminoazetidine-3-carboxylic acid amide hydrochloride salt (I-2A-1h; 1.16 g, 5.37 mmol) in water (10 ml) was treated with diisopropylethylamine (1.90 ml, 10.8 mmol) over 5 minutes. The aqueous solution was then added to the DME solution over a 10-minute period while maintaining the reaction temperature below 28° C. After 2 hours, water (20 ml) was added over 5 minutes, and an orange solid precipitated from the reaction. The solid product was collected by filtration, washed with additional water, and then air dried by pulling low house vacuum across the sample to afford 2A-1 (2.15 g, 84%) as an off-white solid: +ESI MS (M+1) 496.4; $^1$H NMR (400 MHz, CD$_3$OD) δ 7.46-7.35 (m, 4H), 7.31 (d, J=7.7 Hz, 2H), 7.21 (d, J=7.7 Hz, 2H), 5.14 (br d, J=8.3 Hz, 1H), 4.77 (br d, J=8.3 Hz, 1H), 4.61 (br d, J=8.3 Hz, 1H), 4.22 (br d, J=8.3 Hz, 1H), 2.54 (q, J=7.1 Hz, 2H), 2.45 (s, 3H), 1.14 (t, J=7.1 Hz, 3H).

The hydrochloride salt of compound 2A-1 may be prepared using the following procedure To a solution of 1-[7-(2-chlorophenyl)-8-(4-chlorophenyl)-2-methylpyrazolo[1,5-a][1,3,5]triazin-4-yl]-3-ethylaminoazetidine-3-carboxylic acid amide (2A-1; 100 mg, 0.201 mmol) in methanol (2 ml) was added 1M HCl in diethyl ether (0.20 ml). After stirring for 15 minutes, the reaction was concentrated, in vacuo, to a foam. The solid was triturated in 95/5 diethyl ether/ethanol (2 mL) and then stirred over night. The supernate was decanted away, the solids were rinsed with additional ether, and the isolated solid dried, in vacuo, to afford the hydrochloride salt of 2A-1 as a colorless solid (98 mg, 91%): +ESI MS (M+1) 496.1; $^1$H NMR (400 MHz, CD$_3$OD) δ 7.48-7.36 (m, 4H), 7.34 (d, J=8.7 Hz, 2H), 7.23 (d, J=8.7 Hz, 2H), 3.22 (q, J=7.3 Hz, 2H), 2.51 (s, 3H), 1.38 (t, J=7.3 Hz, 3H).

The benzenesulfonate salt of compound 2A-1 may be prepared using the following procedure A solution of 1-[7-(2-chlorophenyl)-8-(4-chlorophenyl)-2-methylpyrazolo[1,5-a][1,3,5]triazin-4-yl]-3-ethylaminoazetidine-3-carboxylic acid amide (2A-1; 0.50 g, 1.01 mmol) in methylene chloride (25 ml) was filtered through a medium sintered glass funnel to remove fine, suspended solids. The solution was concentrated, in vacuo, to an orange oil, and then redesolved in methylene chloride (10 ml). Benezenesulfonic acid (153 mg, 0.87 mmol) was added, portionwise, to give a pale green mixture that was filtered through a cotton plug to give a colorless solution. After stirring overnight a precipitate formed. The mixture was cooled to 0° C., stirred an additional hour, and the solids were collected on a sintered glass funnel to afford, after drying, in vacuo, the benzenesulfonic acid salt of 2A-1 as a colorless solid (515 mg, 90%): +ESI MS (M+1) 496.5; $^1$H NMR (400 MHz, CD$_3$OD) δ 7.81-7.78 (m, 2H), 7.48-7.33 (m, 9H), 7.23 (d, J=8.7 Hz, 2H), 5.5-4.5 (v br m, 4H), 3.18 (q, J=7.3 Hz, 2H), 2.46 (s, 3H), 1.36 (t, J=7.3 Hz, 3H).

A suspension of the benzenesulfonic acid salt of 1-[7-(2-chlorophenyl)-8-(4-chlorophenyl)-2-methylpyrazolo[1,5-a][1,3,5]triazin-4-yl]-3-ethylaminoazetidine-3-carboxylic acid amide (1.20 g, 1.83 mmol) in acetonitrile (24 ml) and water (0.62 ml) was repulped at 75° C. for 16 hours. The mixture was cooled and stirred an additional 8 hours at room temperature. The solids were collected were collected on a sintered glass funnel to afford, after drying, in vacuo, the benzenesulfonic acid salt of 2A-1 as a colorless solid (1.08 mg, 90%).

The methanenesulfonate salt of compound 2A-1 may be prepared using the following procedure To a suspension of 1-[7-(2-chlorophenyl)-8-(4-chlorophenyl)-2-methylpyrazolo[1,5-a][1,3,5]triazin-4-yl]-3-ethylaminoazetidine-3-carboxylic acid amide (2A-1; 75 mg, 0.15 mmol) in acetonitrile (5 ml) was added a solution of methanesulfonic acid in acetonitrile (1 M, 0.16 ml), dropwise. After stirring overnight, the precipitate was collected on a sintered glass funnel (86 mg). The solids were resuspended in 20:1 isopropyl ether/water (4 ml) and then stirred overnight at 60° C. After cooling, the precipitate was collected on a sintered glass funnel and then dried overnight, in vacuo, at 56° C. to afford the methanesulfonic acid salt of 2A-1 as a colorless solid (83 mg, 93%): $^1$H NMR (400 MHz, CD$_3$OD) δ 7.48-7.38 (m, 4H), 7.34 (d, J=8.7 Hz, 2H), 7.22 (d, J=8.7 Hz, 2H), 3.23-315 (br m, 2H), 2.67 (s, 3H), 2.50 (s, 3H), 1.37 (t, J=7.3 Hz, 3H).

Example 3

Preparation of 1-[7-(2-Chlorophenyl)-8-(4-chlorophenyl)-2-methylpyrazolo[1,5-a][1,3,5]triazin-4-yl]-3-isopropylaminoazetidine-3-carboxylic Acid Amide (3A-1)

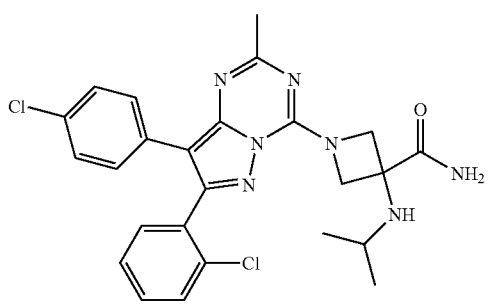

3A-1

To a mixture of 3-isopropylaminoazetidine-3-carboxylic acid amide hydrochloride salt (I-3A-1c; 72 mg, 0.361 mmol) and 4-chloro-7-(2-chlorophenyl)-8-(4-chlorophenyl)-2-methylpyrazolo[1,5-a][1,3,5]triazine (I-2A-1b; 102 mg, 0.261 mmol) in methylene chloride (1.3 ml) was added diisopropylethylamine (0.16 ml, 0.91 mmol), dropwise. After stirring for 90 minutes, the reaction was extracted from saturated aqueous NaHCO$_3$ with methylene chloride. The combined extracts were dried (MgSO$_4$), concentrated, in vacuo, and then purified on a Biotage™ Flash 12M column using 0-5% methanol in methylene chloride as eluant. The resultant solid was triturated from methanol and then dried, in vacuo, to afford 3A-1 (104 mg, 78%) as a colorless solid: +ESI MS (M+1) 510.1; $^1$H NMR (400 MHz, CD$_2$Cl$_2$) δ 7.47-7.34 (m, 6H), 7.21 (d, J=8.7 Hz, 2H), 6.96 (br s, 1H), 5.42 (br s, 1H), 5.22 (br m, 1H), 4.73 (br m, 2H), 4.18 (br m, 1H), 3.11 (septuplet, J=6.2 Hz, 1H), 2.48 (s, 3H), 1.06 (d, J=6.2 Hz, 6H).

The hydrochloride salt of compound 3A-1 may be prepared using the following procedure To a solution of 1-[7-(2-chlorophenyl)-8-(4-chlorophenyl)-2-methylpyrazolo[1,5-a][1,3,5]triazin-4-yl]-3-isopropylaminoazetidine-3-carboxylic acid amide (3A-1; 104 mg, 0.204 mmol) in methylene chloride (7 ml) was added 1M HCl in diethyl ether (0.22 ml). After stirring for 10 minutes, a precipitate began to form. The mixture was concentrated, in vacuo, to afford the hydrochloride salt of 3A-1 as an off-white solid (106 mg, 96%): +ESI MS (M+1) 510.1; $^1$H NMR (400 MHz, CD$_3$OD) δ 7.48-7.37 (m, 4H), 7.33 (d, J=8.7 Hz, 2H), 7.23 (d, J=8.7 Hz, 2H), 3.71 (septuplet, J=6.6 Hz, 1H), 2.52 (s, 3H), 1.36 (d, J=6.6 Hz, 6H).

The compounds listed in Table 2 below were prepared using procedures analogous to those described above for the synthesis of Compound 3A-1 using the appropriate starting materials which are available commercially, prepared using preparations well-known to those skilled in the art, or prepared in a manner analogous to routes described above for other intermediates. The compounds listed below were isolated initially as the free base and then generally converted to their corresponding hydrochloride salt for testing.

TABLE 2

| Example No. | R$^2$ | R$^3$ | —NRR' | MS (M + H)+ |
|---|---|---|---|---|
| 3A-2 | Cl-C$_6$H$_4$- | CH$_3$ | 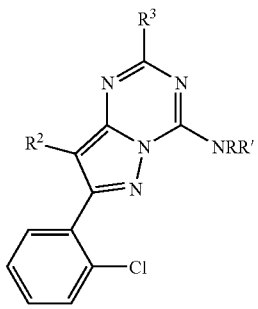 | 482.1 |

TABLE 2-continued

| Example No. | R² | R³ | —NRR' | MS (M + H)+ |
|---|---|---|---|---|
| 3A-3 | 4-Cl-C₆H₄ | CH₃ | azetidine-N, 3-N(CH₃)₂, 3-C(O)NH₂ | 496.2 |
| 3A-4 | 4-Cl-C₆H₄ | CH₃ | 1-methyl-2,6-diazaspiro[3.4]-7-one | 494.2 |
| 3A-5 | 4-Cl-C₆H₄ | CH₃ | 2,6-diazaspiro[3.4]-7-one | 480.1 |
| 3A-6 | 4-Cl-C₆H₄ | CH₃ | azetidine-N, 3-NH₂, 3-C(O)NH₂ | 468.1 |
| 3A-7 | 4-Cl-C₆H₄ | CH₃ | 1-isopropyl-2,8-diazaspiro[4.5]decan-3-one | 550.2 |
| 3A-8 | 4-Cl-C₆H₄ | CH₃ | piperidine-N, 4-NHCH₃, 4-C(O)NH₂ | 510.1 |

TABLE 2-continued
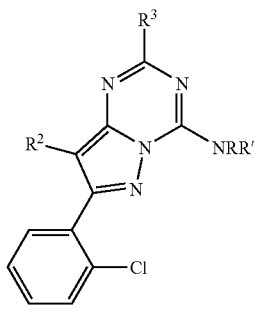
| Example No. | R² | R³ | —NRR' | MS (M + H)+ |
|---|---|---|---|---|
| 3A-9 | 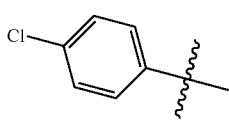 | H | 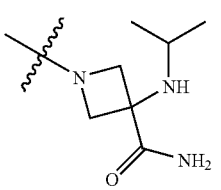 | 496.2 |
| 3A-10 | 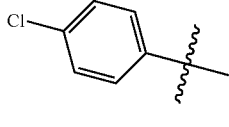 | H | 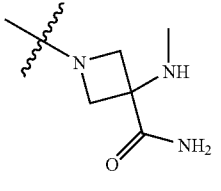 | 468.0 |
| 3A-11 | 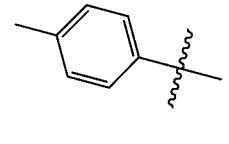 | CH₃ | 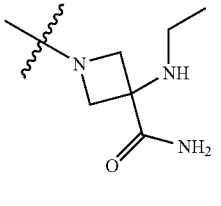 | 476.3 |
| 3A-12 | 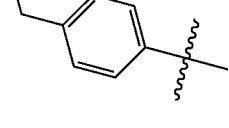 | CH₃ | 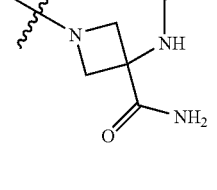 | 490.3 |
| 3A-13 | 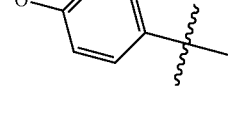 | CH₃ | 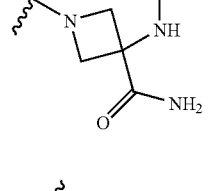 | 492.2 |
| 3A-14 | 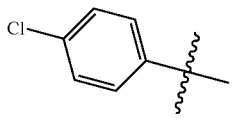 | CH₃ | 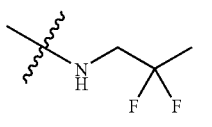 | 448.0 |

Example 4

Preparation of 2-[7-(2-chlorophenyl)-8-(4-chlorophenyl)-2-methylpyrazolo[1,5-a][1,3,5]triazin-4-yl]-6,6-dimethyl-2,5,7-triazaspiro[3.4]octan-8-one (4A-1)

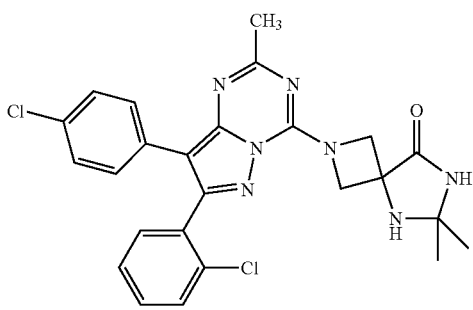

To a mixture of 3-amino-1-[7-(2-chlorophenyl)-8-(4-chlorophenyl)-2-methylpyrazolo[1,5-a][1,3,5]triazin-4-yl]-azetidine-3-carboxylic acid amide (3A-6; 27 mg, 0.057 mmol) and 2,2-dimethoxypropane (0.75 ml, 6.1 mmol) in toluene (1.3 ml) was added acetic acid (5 drops). After stirring at reflux for 18 hours, the reaction was cooled and extracted from saturated aqueous NaHCO₃ with ethyl acetate. The combined extracts were dried (MgSO₄), concentrated, in vacuo, and then purified on a Biotage™ Flash 12S column using 0-5% methanol in methylene chloride as eluant to afford after drying, in vacuo, 4A-1 (16 mg, 55%) as an off-white solid: +ESI MS (M+1) 508.1; ¹H NMR (400 MHz, DMSO-d₆) δ 8.60 (s, 1H), 7.56-7.42 (m, 4H), 7.34-7.30 (m, 4H), 4.92 (d, J=10.4 Hz, 1H), 4.73 (d, J=10.4 Hz, 1H), 4.43 (d, J=10.4 Hz, 1H), 4.19 (d, J=10.4 Hz, 1H), 2.40 (s, 3H), 1.23 (s, 3H), 1.20 (s, 3H).

Example 5

Preparation of 1-[7-(2-Chlorophenyl)-8-(4-chlorophenyl)-pyrazolo[1,5-a][1,3,5]triazin-4-yl]-4-ethylaminopiperidine-4-carboxylic Acid Amide (5A-1)

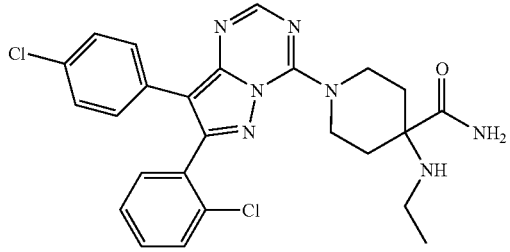

To a mixture of 4-ethylaminopiperidine-4-carboxylic acid amide (I-1A-1h; 25 mg, 0.15 mmol) in dimethylformamide (1.5 ml) was added diisopropylethylamine (0.032 ml, 0.18 mmol) and then di-[7-(2-chlorophenyl)-8-(4-chlorophenyl)-pyrazolo[1,5-a][1,3,5]triazin-4-yl]ether (I-5A-1a; 85 mg, 0.12 mmol), portionwise. After stirring overnight, the reaction was extracted from water with ethyl acetate. The combined extracts were washed with brine, dried (MgSO₄), concentrated, in vacuo, and then purified on a Chromatotron using 8-7/2/0.02 methylene chloride/ethyl acetate/acetic acid as eluant. The resultant solid was extracted from saturated aqueous NaHCO₃ with ethyl actate, the combined extracts were then washed with brine, dried (MgSO₄) and concentrated, in vacuo, to afford 5A-1 (55 mg, 88%) as a solid: +APcI MS (M+1) 510.3; ¹H NMR (400 MHz, CD₃OD) δ 8.14-8.12 (m, 1H), 7.50-7.37 (m, 6H), 7.26-7.20 (m, 2H), 4.30-4.58 (v br m, 2H), 4.45-4.32 (v br m, 2H), 2.59-2.51 (m, 2H), 2.23-2.14 (m, 2H), 1.88-1.79 (m, 2H), 1.15-1.09 (m, 3H).

The hydrochloride salt of compound 5A-1 may be prepared using the following procedure To a solution of 1-[7-(2-chlorophenyl)-8-(4-chlorophenyl)-pyrazolo[1,5-a][1,3,5]triazin-4-yl]-4-ethylaminopiperidine-4-carboxylic acid amide (5A-1; 52 mg, 0.10 mmol) in methanol (1.5 ml) was added 1M HCl in diethyl ether (0.10 ml). After stirring for 30 minutes, the mixture was concentrated, in vacuo, and the residue triturated from diethyl ether to give the hydrochloride salt of 5A-1 as a solid (46 mg, 83%): +ESI MS (M+1) 510.3; ¹H NMR (400 MHz, CD₃OD) δ 8.22-8.21 (m, 1H), 7.52-7.32 (m, 6H), 7.27-7.20 (m, 2H), 4.35-4.23 (br m, 2H), 3.05 (br q, J=7.1 Hz, 2H), 2.62-2.54 (m, 2H), 2.11 (br t, J=10.8 Hz, 2H), 1.37-1.32 (m, 3H).

Preparation of 1-[7-(2-Chlorophenyl)-8-(4-chlorophenyl)-pyrazolo[1,5-a][1,3,5]triazin-4-yl]-3-ethylaminoazetidine-3-carboxylic Acid Amide (5A-2)

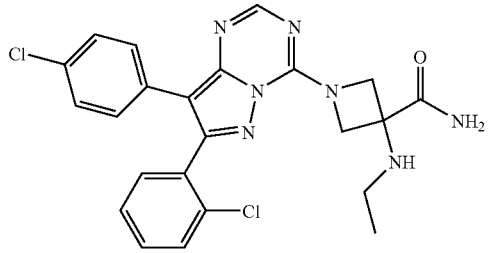

1-[7-(2-Chlorophenyl)-8-(4-chlorophenyl)-pyrazolo[1,5-a][1,3,5]triazin-4-yl]-3-ethylaminoazetidine-3-carboxylic (5A-2) was prepared using procedures analogous to those described above for the synthesis of Compound 5A-1. The compound was isolated initially as the free base and then converted to the corresponding hydrochloride salt for testing: +APcI MS (M+1) 482.1.

Example 6

Preparation of 1-[7-(2-Chlorophenyl)-8-(4-cyanophenyl)-2-methylpyrazolo[1,5-a][1,3,5]triazin-4-yl]-3-ethylaminoazetidine-3-carboxylic Acid Amide (6A1)

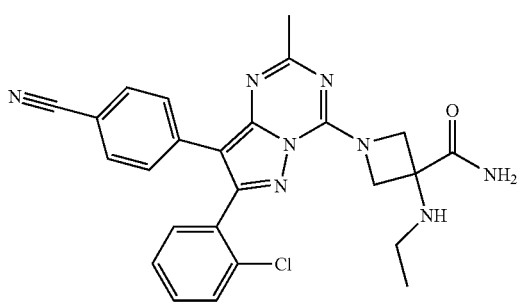

6A-1

A mixture of 1-[7-(2-chlorophenyl)-8-iodo-2-methylpyrazolo[1,5-a][1,3,5]triazin-4-yl]-3-ethylaminoazetidine-3-carboxylic acid amide (I-6A-1a; 50 mg, 0.098 mmol) and 4-cyanophenylboronic acid (22 mg, 0.15 mmol) in dioxane (0.8 ml) and 2M aqueous $Na_2CO_3$ (0.2 ml) was purged with nitrogen gas. Tetrakis(triphenylphosphine)palladium (12.5 mg, 0.01 mmol) was added and the mixture was heated at 68° C. for 4 days. After cooling to room temperature, the mixture was extracted from water with chloroform, the combined organic layers were washed with brine, dried ($MgSO_4$), and then concentrated, in vacuo, to afford the crude product. Purification on a Combiflash® using 0.4% methanol/1% aqueous ammonium hydroxide in chloroform as eluant afforded 6A-1 (23 mg, 48%) as a solid: +ESI MS (M+1) 487.1; $^1$H NMR (400 MHz, $CDCl_3$) δ 7.57 (d, J=8.7 Hz, 2H), 7.51 (d, J=8.7 Hz, 2H), 7.47-7.34 (m, 4H), 7.01 (d, J=4.6 Hz, 1H), 5.39 (d, J=4.6 Hz, 1H), 5.30 (br d, J=9.5 Hz, 1H), 4.80 (br d, J=8.7 Hz, 1H), 4.73 (br d, J=9.5 Hz, 1H), 4.18 (br d, J=8.7 Hz, 1H), 2.64 (t, J=7.0 Hz, 2H), 2.53 (s, 3H), 1.17 (t, J=7.0 Hz, 3H).

The compounds listed in Table 3 below were prepared using procedures analogous to those described above for the synthesis of Compound 6A-1 using the appropriate starting materials which are available commercially, prepared using preparations well-known to those skilled in the art, or prepared in a manner analogous to routes described above for other intermediates. For the preparation of Compound 6A-4, the Pd-mediated coupling was performed overnight in dimethoxyethane using (1,1'-bis(diphenylphosphino)ferrocene)dichloropalladium(II), dichloromethane complex as catalyst.

TABLE 3

| Example No. | $R^2$ | —NRR' | MS (M + H)+ |
|---|---|---|---|
| 6A-2 | 2,4-dichlorophenyl | 3-(ethylamino)-3-carbamoylazetidin-1-yl | 532.0 |
| 6A-3 | 2-chlorophenyl | 3-(ethylamino)-3-carbamoylazetidin-1-yl | 496.1 |
| 6A-4 | 3-chlorophenyl | 3-(ethylamino)-3-carbamoylazetidin-1-yl | 496.1 |

Example 7

Preparation of Butyl-[7-(2-chlorophenyl)-8-(4-chlorophenyl)-2-methylpyrazolo[1,5-a][1,3,5]triazin-4-yl]-amine (7A-1)

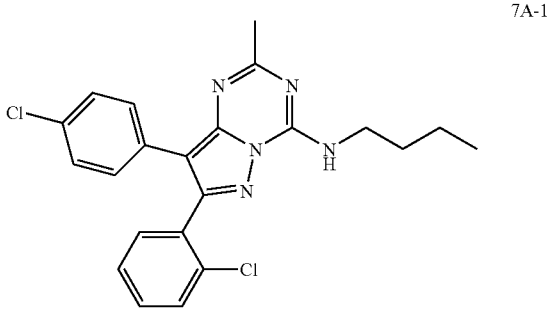

7A-1

To a mixture of butylamine (0.17 ml, 0.15 mmol) and diisopropylethylamine (0.037 ml, 0.21 mmol) in DMF (0.75 ml) was added a solution of 4-chloro-7-(2-chlorophenyl)-8-(4-chlorophenyl)-2-methylpyrazolo[1,5-a][1,3,5]triazine (I-2A-1b; 54 mg, 0.14 mmol) in DMF (1.3 ml). After stirring for 40 hours, the reaction was treated with water, dropwise, until a precipitate formed. After several more hours of stirring, the resultant solid was collected by vacuum filtration, and then washed with water and a small amount of isopropyl alcohol to afford 7A-1 (46 mg, 77%) as a solid: +APcI MS (M+1) 426.2; $^1$H NMR (400 MHz, CD$_3$OD) δ 7.51-7.30 (m, 6H), 7.22-7.18 (m, 2H), 3.63 (t, J=7.1 Hz, 2H), 2.50 (s, 3H), 1.70 (quintet, J=7.3 Hz, 2H), 1.44 (hextuplet, J=7.5 Hz, 2H), 0.98 (t, J=7.5 Hz, 2H).

The compounds listed in Table 4 below were prepared using procedures analogous to those described above for the synthesis of Compound 7A-1 using the appropriate starting materials which are available commercially, prepared using preparations well-known to those skilled in the art, or prepared in a manner analogous to routes described above for other intermediates.

TABLE 4

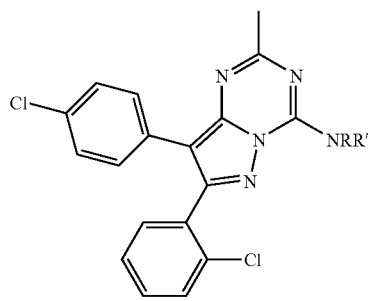

| Example No. | —NRR' | MS (M + H)+ |
|---|---|---|
| 7A-2 | morpholine | 440.1 |
| 7A-3 | 4-methylpiperazine | 453.1 |
| 7A-4 | NH-(6-methoxypyridin-3-yl) | 477.1 |
| 7A-5 | NH-CH2CH2-morpholine | 483.1 |
| 7A-6 | 4-(pyrimidin-2-yl)piperazine | 517.4 |
| 7A-7 | 4-(4-fluorophenyl)-4-hydroxypiperidine | 548.1 |
| 7A-8 | NH-CH2CH2-(4-fluorophenyl) | 492.4 |
| 7A-9 | 4-acetyl-4-phenylpiperidine | 556.2 |
| 7A-10 | 4-benzyl-4-hydroxypiperidine | 544.5 |

Example 8

Preparation of (1S,4S)-5-[7-(2-Chlorophenyl)-8-(4-chlorophenyl)-2-methylpyrazolo[1,5-a][1,3,5]triazin-4-yl]-2,5-diazabicyclo[2.2.1]heptane-2-carboxylic Acid tert-Butyl Ester (8A-1)

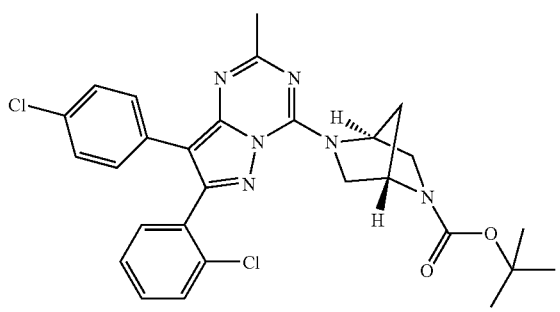

8A-1

To a mixture of 2,5-diazabicyclo[2.2.1]heptane-2-carboxylic acid tert-butyl ester (78 mg, 0.40 mmol) and diisopropylethylamine (0.094 ml, 0.52 mmol) in methylene chloride (2.5 ml) was added 4-chloro-7-(2-chlorophenyl)-8-(4-chlorophenyl)-2-methylpyrazolo[1,5-a][1,3,5]triazine (I-2A-1b; 135 mg, 0.35 mmol), portionwise. After stirring overnight, the reaction was concentrated, in vacuo, to ½ volume and then purified on a Biotage™ Flash 12M column using 0-3% ethyl acetate in methylene chloride to afford 8A-1 (200 mg, quantitative) as a solid: +APcI MS (M+1) 551.2; $^1$H NMR (400 MHz, CD$_3$OD) δ 7.50-7.34 (m, 4H), 7.32 (d, J=8.3 Hz, 2H), 7.21 (d, J=8.3 Hz, 2H), 4.60 (br s, 1H), 2.46 (s, 3H), 2.10-1.99 (br m, 2H), 1.50-1.40 (m, 9H).

The compounds listed in Table 5 below were prepared using procedures analogous to those described above for the synthesis of Compound 8A-1 using the appropriate starting materials which are available commercially, prepared using preparations well-known to those skilled in the art, or prepared in a manner analogous to routes described above for other intermediates. The compounds listed below were isolated initially as the free base and then generally converted to their corresponding hydrochloride salt for testing.

TABLE 5

| Example No. | —NRR' | MS (M + H)+ |
|---|---|---|
| 8A-2 | ![structure: N-methyl-N-(2,2,2-trifluoroethyl)amine] | 466.4 |

TABLE 5-continued

| Example No. | —NRR' | MS (M + H)+ |
|---|---|---|
| 8A-3 | ![structure: N-(2,2,2-trifluoroethyl)amine] | 452.0 |
| 8A-4 | ![structure: N-isopropylamine] | 412.1 |

Example 9

Preparation of 7-(2-Chlorophenyl)-8-(4-chlorophenyl)-4-[(1S,4S)-2,5-diazabicyclo[2.2.1]hept-2-yl]-2-methylpyrazolo[1,5-a][1,3,5]triazine, Hydrochloride Salt (9A-1)

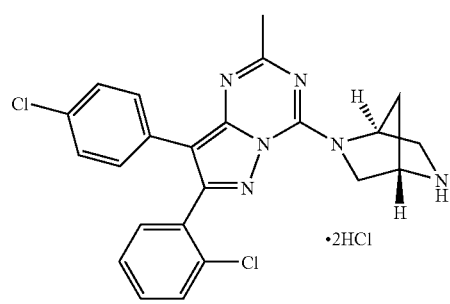

9A-1

To a solution of (1S,4S)-5-[7-(2-chlorophenyl)-8-(4-chlorophenyl)-2-methylpyrazolo[1,5-a][1,3,5]triazin-4-yl]-2,5-diazabicyclo[2.2.1]heptane-2-carboxylic acid tert-butyl ester (8A-1; 200 mg, 0.36 mmol) in methylene chloride (3 ml) and methanol (3 ml) was added 1M HCl in diethyl ether (1.8 ml, 1.8 mmol). After stirring overnight, the reaction was concentrated, in vacuo, and then triturated from diethyl ether to afford 9A-1 (180 mg, 96%) as a solid: +ESI MS (M+1) 451.3; $^1$H NMR (400 MHz, CD$_3$OD) δ 7.48-7.36 (m, 4H), 7.32 (d, J=8.7 Hz, 2H), 7.26 (d, J=8.7 Hz, 2H), 4.64 (s, 1H), 3.68 (d, J=10.8 Hz, 1H), 3.55 (dd, J=10.8, 1.6 Hz, 1H), 2.58 (s, 3H), 2.41 br d, J=11.2 Hz, 1H), 2.18 (d, J=11.2 Hz, 1H).

The compounds listed in Table 6 below were prepared using procedures analogous to those described above for the synthesis of Compound 9A-1 using the appropriate materials which are available commercially, prepared using preparations well-known to those skilled in the art, or prepared in a manner analogous to routes described above for other intermediates.

TABLE 6

| Example No. | —NRR' | MS (M + H)+ |
|---|---|---|
| 9A-2 | piperazine | 439.2 |
| 9A-3 | 3-amino-azabicyclo[3.1.0]hexane | 451.3 |

Example 10

Preparation of (1S,4S)-7-(2-Chlorophenyl)-8-(4-chlorophenyl)-2-methyl-4-[5-(ethanesulfonyl)-2,5-diazabicyclo[2.2.1]hept-2-yl]-pyrazolo[1,5-a][1,3,5]triazine (10A-1)

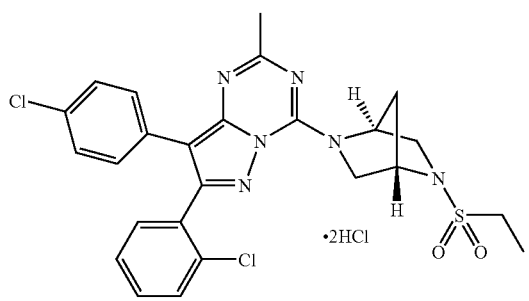

10A-1

To a suspension of (1S,4S)-7-(2-chlorophenyl)-8-(4-chlorophenyl)-4-(2,5-diazabicyclo[2.2.1]hept-2-yl)-2-methylpyrazolo[1,5-a][1,3,5]triazine, hydrochloride salt (9A-1; 24.3 mg, 0.0463 mmol) in methylene chloride (1 ml) was added diisopropylethylamine (0.028 ml, 0.16 mmol), followed by a 0.56 M solution of ethanesulfonyl chloride in methylene chloride (0.1 ml, 0.056 mmol). After stirring overnight, the reaction directly loaded and then purified on a Biotage™ Flash 12S column using 0-20% methanol in methylene chloride as eluant to afford 10A-1 (18 mg, 72%) as a solid: +ESI MS (M+1) 543.3; $^1$H NMR (400 MHz, CD$_3$OD) δ 7.50-7.36 (m, 4H), 7.32 (d, J=8.3 Hz, 2H), 7.21 (d, J=8.3 Hz, 2H), 4.58 (br s, 1H), 3.62 (s, 2H), 3.11 (q, J=7.5 Hz, 2H), 2.46 (s, 3H), 2.18-2.21 (br m, 2H), 1.30 (t, J=7.5 Hz, 2H).

The compounds listed in Table 7 below were prepared using procedures analogous to those described above for the synthesis of Compound 10A-1 using the appropriate starting materials which are available commercially, prepared using preparations well-known to those skilled in the art, or prepared in a manner analogous to routes described above for other intermediates. Compounds 10A-9 and 10A-10 were isolated initially as the free base and then converted to their corresponding hydrochloride salt for testing.

TABLE 7

| Example No. | —NRR' | MS (M + H)+ |
|---|---|---|
| 10A-2 | acetyl-diazabicyclo[2.2.1]heptane | 493.4 |
| 10A-3 | isobutyryl-diazabicyclo[2.2.1]heptane | 521.4 |
| 10A-4 | benzoyl-diazabicyclo[2.2.1]heptane | 555.4 |
| 10A-5 | methanesulfonyl-diazabicyclo[2.2.1]heptane | 529.3 |

TABLE 7-continued

| Example No. | —NRR' | MS (M + H)+ |
|---|---|---|
| 10A-6 | (4-isopropylsulfonyl-2,5-diazabicyclo[2.2.1]heptane) | 557.3 |
| 10A-7 | (4-(N,N-dimethylcarbamoyl)-2,5-diazabicyclo[2.2.1]heptane) | 543.3 |
| 10A-8 | (4-isopropylsulfonylpiperazine) | 545.4 |
| 10A-9 | (4-ethylsulfonylpiperazine) | 531.4 |
| 10A-10 | (4-methylsulfonylpiperazine) | 517.4 |

Example 11

Preparation of 4-(1-tert-Butylazetidin-3-yloxy)-7-(2-chlorophenyl)-8-(4-chlorophenyl)-2-methylpyrazolo [1,5-a][1,3,5]triazine (11A-1)

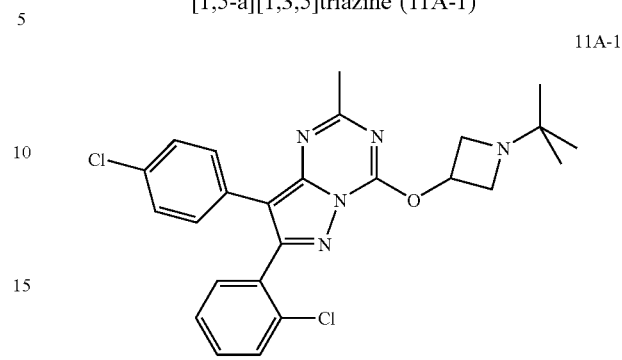

11A-1

To a solution of 1-tert-butylazetidin-3-ol (19 mg, 0.15 mmol), 1,4-diazabicyclo[2.2.2]octane (11 mg, 0.10 mmol), and diisopropylethylamine (0.026 ml, 0.15 mmol) in tetrahydrofuran (1 ml) was added 4-chloro-7-(2-chlorophenyl)-8-(4-chlorophenyl)-2-methylpyrazolo[1,5-a][1,3,5]triazine (I-2A-1b; 39 mg, 0.10 mmol), portionwise. After stirring for 2 days, the reaction was concentrated, in vacuo, and the residue purified on a Biotage™ Flash 12S column using 20-40% ethyl acetate in hexanes to afford 11A-1 (25 mg, 52%) as a solid: +APcI MS (M+1) 482.3; $^1$H NMR (400 MHz, CD$_3$OD) δ 7.52-7.42 (m, 4H), 7.39 (d, J=8.3 Hz, 2H), 7.24 (d, J=8.3 Hz, 2H), 5.58 (quintet, J=6.2 Hz, 1H), 3.80-3.75 (m, 2H), 3.63-3.58 (m, 2H), 2.60 (s, 3H), 1.04 (s, 9H).

The compounds listed in Table 8 below were prepared using procedures analogous to those described above for the synthesis of Compound 11A-1 using the appropriate starting materials which are available commercially, prepared using preparations well-known to those skilled in the art, or prepared in a manner analogous to routes described above for other intermediates.

TABLE 8

| Example No. | —OR | MS (M + H)+ |
|---|---|---|
| 11A-2 | (3-(cyclohexylamino)azetidin-1-yl)oxy | 508.4 |
| 11A-3 | (3-(isopropylamino)azetidin-1-yl)oxy | 468.4 |

TABLE 8-continued

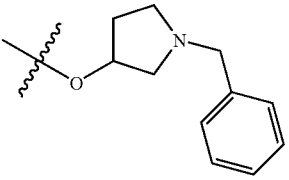

| Example No. | —OR | MS (M + H)+ |
|---|---|---|
| 11A-4 | 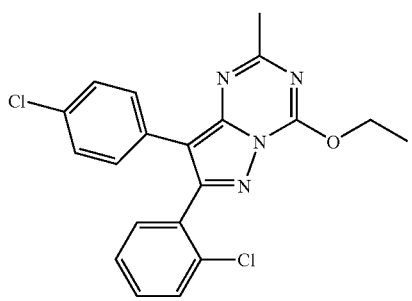 | 530.2 |

Example 12

Preparation of 7-(2-Chlorophenyl)-8-(4-chlorophenyl)-4-ethoxy-2-methylpyrazolo[1,5-a][1,3,5]triazine (12A-1)

12A-1

To a solution of 4-chloro-7-(2-chlorophenyl)-8-(4-chlorophenyl)-2-methylpyrazolo[1,5-a][1,3,5]triazine (I-2A-1b; 20 mg, 0.051 mmol) in ethanol (1 ml) was added NaH (60% dispersion in oil, 2 mg, 0.05 mmol), portionwise. After stirring for 6 hours, the reaction was concentrated, in vacuo. The residue was redisolved in methylene chloride, filtered through a 0.45 μm disk, and then concentrated to afford 12A-1 (18 mg, 88%) as a solid: +APcI MS (M+1) 399.1; $^1$H NMR (400 MHz, CD$_2$Cl$_2$) δ 7.50-7.37 (m, 6H), 7.24 (d, J=8.7 Hz, 2H), 4.80 (q, J=7.2 Hz, 2H), 2.63 (s, 3H), 1.57 (t, J=7.1 Hz, 3H).

Example 13

Preparation of 7-(2-Chlorophenyl)-8-(4-chlorophenyl)-4-isopropoxy-2-methylpyrazolo[1,5-a][1,3,5]triazine (13A-1)

13A-1

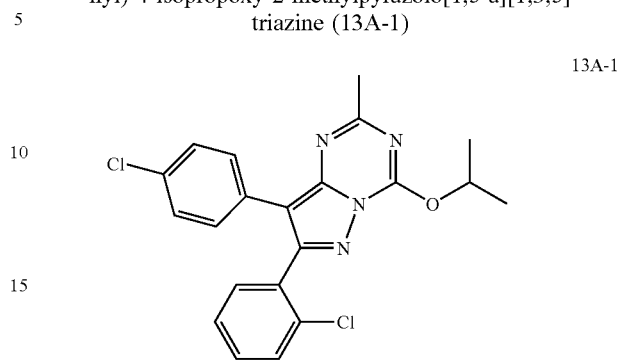

To a suspension of 4-chloro-7-(2-chlorophenyl)-8-(4-chlorophenyl)-2-methylpyrazolo[1,5-a][1,3,5]triazine (I-2A-1b; 150 mg, 0.384 mmol) in isopropanol (5 ml) was added solid NaHCO$_3$ (129 mg, 1.5 mmol), and the mixture was heated at 80° C. overnight. After cooling, the suspended solids (150 mg) were collected by filtration and the filtrate was concentrated, in vacuo, to give a solid (95 mg). The suspended solids were extracted from saturated aqueous NaHCO$_3$ with ethyl acetate, the organic layers were dried (MgSO$_4$) and then concentrated, in vacuo, to give a solid. The combined solids were then purified on a Biotage™ Flash 12M column using 0-10% ethyl acetate in hexanes to afford 13A-1 (91 mg, 60%) as an off-white solid: +ESI MS (M+1) 413.4; $^1$H NMR (400 MHz, CD$_2$Cl$_2$) δ 7.50-7.34 (m, 6H), 7.24 (d, J=8.7 Hz, 2H), 5.73 (septuplet, J=6.2 Hz, 1H), 2.62 (s, 3H), 1.55 (d, J=6.2 Hz, 6H).

The compounds listed in Table 9 below were prepared using procedures analogous to those described above for the synthesis of Compound 13A-1 using the appropriate starting materials which are available commercially, prepared using preparations well-known to those skilled in the art, or prepared in a manner analogous to routes described above for other intermediates.

TABLE 9

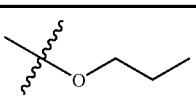

| Example No. | —OR | MS (M + H)+ |
|---|---|---|
| 13A-2 | 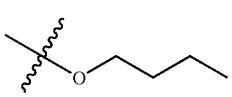 | 413.4 |
| 13A-3 | 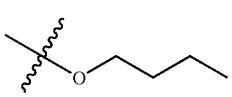 | 427.4 |

Example 14

Preparation of 7-(2-Chlorophenyl)-8-(4-chlorophenyl)-4-(1-ethoxyvinyl)-2-methylpyrazolo[1,5-a][1,3,5]triazine (14A-1)

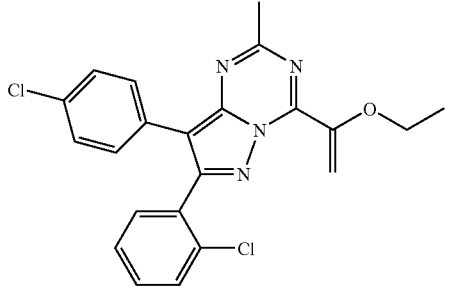

14A-1

To a mixture of 4-chloro-7-(2-chlorophenyl)-8-(4-chlorophenyl)-2-methylpyrazolo[1,5-a][1,3,5]triazine (I-2A-1b; 100 mg, 0.257 mmol) and tetrakis(triphenylphosphine)palladium(0) (15 mg, 0.013 mmol) in DMF (0.8 ml) was added tributyl(1-ethoxyvinyl)tin (130 mg, 0.36 mmol) in DMF (1.5 ml). The reaction was degassed (3×) by pulling a vacuum and refilling with nitrogen. After heating at 100° C. for 1 hour under nitrogen, the reaction was cooled and then extracted from water with ethyl acetate. The organic layer was washed with ½ saturated brine and then brine. After drying (MgSO$_4$), the mixture was concentrated, in vacuo, and purified on a Biotage™ Flash 12M column using 10% ethyl acetate in hexanes to afford product 14A-1 as a solid (53 mg, 49%): +APcI MS (M+1) 425.1; $^1$H NMR (400 MHz, CD$_3$OD) δ 7.50-7.38 (m, 6H), 7.27 (d, J=8.7 Hz, 2H), 6.20 (d, J=3.3 Hz, 1H), 5.19 (d, J=3.3 Hz, 1H), 4.05 (q, J=7.1 Hz, 2H), 2.75 (s, 3H), 1.45 (t, J=7.1 Hz, 3H).

Pharmacological Testing

The utility of the compounds of the present invention in the practice of the instant invention can be evidenced by activity in at least one of the protocols described hereinbelow. The following acronyms are used in the protocols described below.

BSA—bovine serum albumin
DMSO—dimethylsulfoxide
EDTA—ethylenediamine tetracetic acid
PBS—phosphate-buffered saline
EGTA—ethylene glycol-bis(β-aminoethyl ether) N,N,N',N'-tetraacetic acid
GDP—guanosine diphosphate
sc—subcutaneous
po—orally
ip—intraperitoneal
icv—intra cerebro ventricular
iv—intravenous
[$^3$H]SR141716A—radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.
[$^3$H]CP-55940—radiolabled 5-(1,1-dimethylheptyl)-2-[5-hydroxy-2-(3-hydroxypropyl)-cyclohexyl]-phenol available from NEN Life Science Products, Boston, Mass.
AM251—N-(piperidin-1-yl)-1-(2,4-dichlorophenyl)-5-(4-iodophenyl)-4-methyl-1H-pyrazole-3-carboxamide available from Tocris™, Ellisville, Mo.

All of the compounds listed in the Example section above were tested in the CB-1 receptor binding assay below. The compounds provided a range of binding activities from 0.1 nM to 590 nM. Those compounds having an activity <20 nM were then tested in the CB-1 GTPγ [$^{35}$S] Binding Assay and the CB-2 binding assay described below in the Biological Binding Assays section. Selected compounds were then tested in vivo using one or more of the functional assays described in the Biological Functional Assays section below.

In Vitro Biological Assays

Bioassay systems for determining the CB-1 and CB-2 binding properties and pharmacological activity of cannabinoid receptor ligands are described by Roger G. Pertwee in "Pharmacology of Cannabinoid Receptor Ligands" *Current Medicinal Chemistry*, 6, 635-664 (1999) and in WO 92/02640 (U.S. application Ser. No. 07/564,075 filed Aug. 8, 1990, incorporated herein by reference).

The following assays were designed to detect compounds that inhibit the binding of [$^3$H] SR141716A (selective radiolabeled CB-1 ligand) and [$^3$H] 5-(1,1-dimethyl heptyl)-2-[5-hydroxy-2-(3-hydroxypropyl)-cyclohexyl]-phenol ([$^3$H] CP-55940; radiolabeled CB-1/CB-2 ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM MgCl$_2$, and 1 mM EDTA) per brain used. A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [$^3$H] SR141716A was diluted in a ligand buffer (0.5% BSA plus TME) and 25 μl were added to the plate. A BCA protein assay was used to determine the appropriate tissue concentration and then 200 μl of rat brain tissue at the appropriate concentration was added to the plate. The plates were covered and placed in an incubator at 20° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×g for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM $MgCl_2$ and 1 mM EDTA). A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [3H] SR141716A was diluted in a ligand buffer (0.5% BSA plus TME) and 25 μl were added to the plate. The plates were covered and placed in an incubator at 30° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

CB-2 Receptor Binding Protocol

Chinese hamster ovary-K1 (CHO-K1) cells transfected with CB-2 cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM $MgCl_2$ and 1 mM EDTA) per brain used. A protein assay was performed and 200 μl of tissue totaling 10 μg was added to the assay.

The test compounds were diluted in drug buffer (0.5% BSA, 10% DMSO, and 80.5% TME) and then 25 μl were added to the deep well polypropylene plate. [3H] CP-55940 was diluted a ligand buffer (0.5% BSA and 99.5% TME) and then 25 μl were added to each well at a concentration of 1 nM. A BCA protein assay was used to determine the appropriate tissue concentration and 200 μl of the tissue at the appropriate concentration was added to the plate. The plates were covered and placed in an incubator at 30° C. for 60 minutes. At the end of the incubation period 250 μl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 GTPγ [$^{35}$S] Binding Assay

Membranes were prepared from CHO-K1 cells stably transfected with the human CB-1 receptor cDNA. Membranes were prepared from cells as described by Bass et al, in "Identification and characterization of novel somatostatin antagonists," *Molecular Pharmacology*, 50, 709-715 (1996). GTPγ [$^{35}$S] binding assays were performed in a 96 well FlashPlate™ format in duplicate using 100 pM GTPγ[$^{35}$S] and 10 μg membrane per well in assay buffer composed of 50 mM Tris HCl, pH 7.4, 3 mM $MgCl_2$, pH 7.4, 10 mM $MgCl_2$, 20 mM EGTA, 100 mM NaCl, 30 μM GDP, 0.1% bovine serum albumin and the following protease inhibitors: 100 μg/ml bacitracin, 100 μg/ml benzamidine, 5 μg/ml aprotinin, 5 μg/ml leupeptin. The assay mix was then incubated with increasing concentrations of antagonist ($10^{-10}$ M to $10^{-5}$ M) for 10 minutes and challenged with the cannabinoid agonist CP-55940 (10 μM). Assays were performed at 30° C. for one hour. The FlashPlates™ were then centrifuged at 2000×g for 10 minutes. Stimulation of GTPγ[$^{35}$S] binding was then quantified using a Wallac Microbeta. $EC_{50}$ calculations done using Prism™ by Graphpad.

Inverse agonism was measured in the absense of agonist.

CB-1 FLIPR-based Functional Assay Protocol

CHO-K1 cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4 μM Fluo-4 AM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 min the plates were added to the FLIPR individually and fluorescence levels was continuously monitored over an 80 second period. Compound additions were made simultaneously to all 384 wells after 20 seconds of baseline. Assays were performed in triplicate and 6 point concentration-response curves generated. Antagonist compounds were subsequently challenged with 3 μM WIN 55,212-2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000-14,000 cells per well at a concentration of 100 μl per well. The plates were incubated for 24 hours in a 37° C. incubator. The media was removed and media lacking serum (100 μl) was added. The plates were then incubated for 18 hours at 37° C.

Serum free medium containing 1 mM IBMX was added to each well followed by 10 μl of test compound (1:10 stock solution (25 mM compound in DMSO) into 50% DMSO/PBS) diluted 10× in PBS with 0.1% BSA. After incubating for 20 minutes at 37° C., 2 μM of Forskolin was added and then incubated for an additional 20 minutes at 37° C. The media was removed, 100 μl of 0.01N HCl was added and then incubated for 20 minutes at room temperature. Cell lysate (75 μl) along with 25 μl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agoinists such as $\Delta^9$-tetrahydrocannabinol ($\Delta^9$-THC) and CP-55940 have been shown to affect four characteristic behaviors in mice, collectively known as the Tetrad. For a description of these behaviors see: Smith, P. B., et al. in "The pharmacological activity of anandamide, a putative endogenous cannabinoid, in mice." J. Pharmacol. Exp. Ther., 270(1), 219-227 (1994) and Wiley, J., et al. in "Discriminative stimulus effects of anandamide in rats," Eur.

J. Pharmacol., 276(1-2), 49-54 (1995). Reversal of these activities in the Locomotor Activity, Catalepsy, Hypothermia, and Hot Plate assays described below provides a screen for in vivo activity of CB-1 antagonists.

All data is presented as % reversal from agonist alone using the following formula: (CP/agonist—vehicle/agonist)/(vehicle/vehicle—vehicle/agonist). Negative numbers indicate a potentiation of the agonist activity or non-antagonist activity. Positive numbers indicate a reversal of activity for that particular test.

Locomotor Activity

Male ICR mice (n=6; 17-19 g, Charles River Laboratories, Inc., Wilmington, Mass.) were pre-treated with test compound (sc, po, ip, or icv). Fifteen minutes later, the mice were challenged with CP-55940 (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6; 17-19 g upon arrival) were pre-treated with test compound (sc, po, ip or icv). Fifteen minutes later, the mice were challenged with CP-55940 (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5; 17-19 g upon arrival) were pre-treated with test compounds (sc, po, ip or icv). Fifteen minutes later, mice were challenged with the cannabinoid agonist CP-55940 (sc). Sixty-five minutes post agonist injection, rectal body temperatures were taken. This was done by inserting a small thermostat probe approximately 2-2.5 cm into the rectum. Temperatures were recorded to the nearest tenth of a degree Hot Plate Male ICR mice (n=7; 17-19 g upon arrival) are pre-treated with test compounds (sc, po, ip or iv). Fifteen minutes later, mice were challenged with a cannabinoid agonist CP-55940 (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats were individually housed and fed powdered chow. They were maintained on a 12-hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li, T.-K., et al., "Indiana selection studies on alcohol related behaviors" in *Development of Animal Models as Pharmacogenetic Tools* (eds McClearn C. E., Deitrich R. A. and Erwin V. G.), Research Monograph 6, 171-192 (1981) NIAAA, ADAMHA, Rockville, Md.; Lumeng, L, et al., "New strains of rats with alcohol preference and nonpreference" *Alcohol And Aldehyde Metabolizing Systems*, 3, Academic Press, New York, 537-544 (1977); and Lumeng, L, et al., "Different sensitivities to ethanol in alcohol-preferring and nonpreferring rats," *Pharmacol. Biochem Behav.*, 16, 125-130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n=8); Group 2—positive control (e.g., 5.6 mg/kg AM251; n=8); Group 3—low dose test compound (n=8); and Group 4—high dose of test compound (n=8). Test compounds were generally mixed into a vehicle of 30%

(w/v) β-cyclodextrin in distilled water at a volume of 1-2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between drug and vehicle-treated animals to determine effects of the compounds on alcohol drinking behavior.

Additional drinking studies were done utilizing female C57BI/6 mice (Charles River). Several studies have shown that this strain of mice will readily consume alcohol with little to no manipulation required (Middaugh et al., "Ethanol Consumption by C57BL/6 Mice: Influence of Gender and Procedural Variables" *Alcohol,* 17 (3), 175-183, 1999; Le et al., "Alcohol Consumption by C57BL/6, BALA/c, and DBA/2 Mice in a Limited Access Paradigm" *Pharmacology Biochemisrty and Behavior,* 47, 375-378, 1994).

For our purposes, upon arrival (17-19 g) mice were individually housed and given unlimited access to powdered rat chow, water and a 10% (w/v) alcohol solution. After 2-3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7-10) so that all groups had equivocal alcohol intake. On day 2 and 3, mice were injected with vehicle or test compound and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e., sc, ip, iv). Drugs are prepared in methylcellulose, water or other specified vehicle (examples include PEG400, 30% beta-cyclodextran and propylene glycol). Oxygen consumption and ambulatory activity are measured every 10 minutes for an additional 1-6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min $O_2$ consumption values, excluding periods of high ambulatory activity (ambulatory activity count>100) and excluding the first 5 values of the pre-dose period and the first value from the post-dose period. Change in oxygen consumption is reported as percent and is calculated by dividing the post-dosing resting oxygen consumption by the pre-dose oxygen consumption*100. Experiments will typically be done with n=4-6 rats and results reported are mean+/−SEM.

Interpretation:

An increase in oxygen consumption of >10% is considered a positive result. Historically, vehicle-treated rats have no change in oxygen consumption from pre-dose basal.

What is claimed is:

1. A compound of Formula (I)

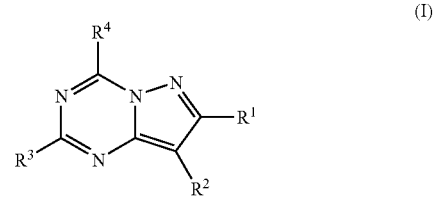

(I)

wherein
$R^1$ is an optionally substituted aryl or an optionally substituted heteroaryl;
$R^2$ is an optionally substituted aryl;
$R^3$ is hydrogen, $(C_1-C_4)$alkyl, halo-substituted $(C_1-C_4)$ alkyl, or $(C_1-C_4)$alkoxy;
$R^4$ is
(i) a group having Formula (IA)

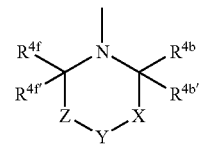

IA where
$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —$C(R^{4d})(R^{4d'})$—, where $R^{4d}$ and $R^{4d'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated heterocyclic ring, a 5-6 membered lactone ring, or a 4-6 membered lactam ring, where said heterocyclic ring, said lactone ring and said lactam ring are optionally substituted with one or more substituents and said lactone ring and said lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said moiety is optionally substituted with one or more substituents;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

a pharmaceutically acceptable salt thereof.

2. The compound of claim 1 wherein $R^4$ is a group having Formula (IA)

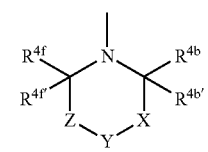

IA where, $R^{4b}$ and $R^{4b'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl$)_2$N—C(O)—, aryl, heteroaryl, a partially or fully saturated 3-6 membered heterocycle, and a 3-6 membered partially or fully saturated carbocyclic ring, where said moiety is optionally substituted with one or more substituents, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl$)_2$N—C(O)—, aryl, heteroaryl, a 3-6 membered partially or fully saturated heterocycle, and a 3-6 membered partially or fully saturated carbocyclic ring, where said moiety is optionally substituted with one or more substituents, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —C($R^{4d}$)($R^{4d'}$)—, where $R^{4d}$ is hydrogen, cyano, hydroxy, amino, $H_2NC(O)$—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, ($C_1$-$C_4$)alkyl)$_2$N—C(O)—, ($C_1$-$C_6$)alkylamino-, (($C_1$-$C_4$)alkyl)$_2$amino-, ($C_3$-$C_6$)cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a 3-6 membered partially or fully saturated carbocyclic ring, where said moiety is optionally substituted with one or more substituents, and $R^{4d'}$ is hydrogen, $H_2NC(O)$—, or a chemical moiety selected from the group consisting of ($C_1$-$C_6$)alkyl, acyl, ($C_1$-$C_3$)alkyl-O—C(O)—, ($C_1$-$C_4$)alkyl-NH—C(O)—, ($C_1$-$C_4$)alkyl)$_2$N—C(O)—, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated heterocyclic ring, a 5-6 membered lactone ring, or a 4-6 membered lactam ring, where said heterocyclic ring, said lactone ring and said lactam ring are optionally substituted with one or more substituents and said lactone ring and said lactam ring optionally contain an additional heteroatom selected from oxygen, nitrogen or sulfur, or Y is —NR$^{4d''}$—, where $R^{4d''}$ is a hydrogen or a chemical moiety selected from the group consisting of ($C_1$-$C_6$) alkyl, ($C_3$-$C_6$)cycloalkyl, ($C_1$-$C_3$)alkylsulfonyl-, ($C_1$-$C_3$)alkylaminosulfonyl-, di($C_1$-$C_3$)alkylaminosulfonyl-, acyl, ($C_1$-$C_6$)alkyl-O—C(O)—, aryl, and heteroaryl, where said moiety is optionally substituted with one or more substituents;

Z is a bond, —$CH_2CH_2$—, or —C($R^{4e}$)($R^{4e'}$)—, where $R^{4e}$ is hydrogen, cyano, hydroxy, amino, $H_2NC(O)$—, or a chemical moiety selected from the group consisting of ($C_1$-$C_6$)alkyl, ($C_1$-$C_6$)alkoxy, acyloxy, acyl, ($C_1$-$C_3$)alkyl-O—C(O)—, ($C_1$-$C_4$)alkyl-NH—C(O)—, ($C_1$-$C_4$)alkyl)$_2$N—C(O)—, ($C_1$-$C_6$)alkylamino-, (($C_1$-$C_4$)alkyl)$_2$amino-, ($C_3$-$C_6$)cycloalkylamino-, acylamino-, aryl($C_1$-$C_4$)alkylamino-, heteroaryl($C_1$-$C_4$) alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4e}$ taken together with $R^{4b}$, $R^{4b'}$, $R^{4c}$ or $R^{4c'}$ forms a bond, a methylene bridge, or an ethylene bridge, and $R^{4e'}$ is hydrogen, $H_2NC(O)$—, or a chemical moiety selected from the group consisting of ($C_1$-$C_6$)alkyl, acyl, ($C_1$-$C_3$)alkyl-O—C(O)—, ($C_1$-$C_4$)alkyl-NH—C(O)—, ($C_1$-$C_4$)alkyl)$_2$N—C(O)—, aryl, heteroaryl, a 3-6 membered partially or fully saturated heterocycle, and a 3-6 membered partially or fully saturated carbocyclic ring, where said moiety is optionally substituted with one or more substituents, or $R^{4e'}$ taken together with $R^{4b}$, $R^{4b'}$, $R^{4c}$ or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of ($C_1$-$C_6$)alkyl, acyl, ($C_1$-$C_3$)alkyl-O—C(O)—, ($C_1$-$C_4$)alkyl-NH—C(O)—, ($C_1$-$C_4$)alkyl)$_2$N—C(O)—, aryl, heteroaryl, a 3-6 membered partially or fully saturated heterocycle, and a 3-6 membered partially or fully saturated carbocyclic ring, where said moiety is optionally substituted with one or more substituents, or $R^{4f}$ or $R^{4f'}$ taken together with $R^{4b}$, $R^{4b'}$, $R^{4c}$ or $R^{4c'}$ forms a bond, a methylene bridge, or an ethylene bridge;

a pharmaceutically acceptable salt thereof.

3. The compound of claim of 2 wherein $R^1$ and $R^2$ are each independently a substituted phenyl;

$R^{4b}$ is hydrogen, an optionally substituted ($C_1$-$C_3$)alkyl, or taken together with $R^{4e}$, $R^{4e'}$, $R^{4f}$, or $R^{4f'}$ forms a bond, a methylene bridge, or an ethylene bridge;

$R^{4b'}$ is hydrogen, an optionally substituted ($C_1$-$C_3$)alkyl, or taken together with $R^{4e}$, $R^{4e'}$, $R^{4f}$, or $R^{4f'}$ forms a bond, a methylene bridge, or an ethylene bridge;

$R^{4f}$ is hydrogen, an optionally substituted ($C_1$-$C_3$)alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted ($C_1$-$C_3$)alkyl, or taken together with $R^{4b}$, $R^{4b'}$, $R^{4c}$, or $R^{4c'}$ forms a bond, a methylene bridge, or an ethylene bridge;

a pharmaceutically acceptable salt thereof.

4. The compound of claim 3 wherein

X is —C($R^{4c}$)($R^{4c'}$)—, where $R^{4c}$ and $R^{4c'}$ are each independently hydrogen, $H_2NC(O)$—, or a chemical moiety selected from ($C_1$-$C_6$)alkyl, ($C_1$-$C_4$)alkyl-NH—C(O)—, or (($C_1$-$C_4$)alkyl)$_2$N—C(O)—, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is —NR$^{4d''}$—, where $R^{4d''}$ is a hydrogen or a chemical moiety selected from the group consisting of ($C_1$-$C_6$) alkyl, ($C_3$-$C_6$)cycloalkyl, ($C_1$-$C_3$)alkylsulfonyl, ($C_1$-$C_3$)alkylaminosulfonyl, di($C_1$-$C_3$)alkylaminosulfonyl, acyl, ($C_1$-$C_6$)alkyl-O—C(O)—, aryl, and heteroaryl, where said moiety is optionally substituted with one or more substituents;

Z is —C($R^{4e}$)($R^{4e'}$)—, where $R^{4e}$ and $R^{4e'}$ are each independently hydrogen, $H_2NC(O)$—, or a chemical moiety selected from $C_1$-$C_6$)alkyl, ($C_1$-$C_4$)alkyl-NH—C(O)—, or (($C_1$-$C_4$)alkyl)$_2$N—C(O)—, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge;

a pharmaceutically acceptable salt thereof.

5. The compound of claim 4 wherein $R^{4d''}$ is a hydrogen or a chemical moiety selected from the group consisting of ($C_1$-$C_3$)alkyl, ($C_1$-$C_3$)alkylsulfonyl, ($C_1$-$C_3$)alkylaminosulfonyl, di($C_1$-$C_3$)alkylaminosulfonyl, acyl, ($C_1$-$C_6$)alkyl-O—C(O)—, and heteroaryl, where said moiety is optionally substituted with one or more substituents;

a pharmaceutically acceptable salt thereof.

6. The compound of claim 5 wherein $R^{4d''}$ is a hydrogen or a chemical moiety selected from the group consisting of ($C_1$-$C_3$)alkyl, ($C_1$-$C_3$)alkylsulfonyl, ($C_1$-$C_3$)alkylaminosulfonyl, di($C_1$-$C_3$)alkylaminosulfonyl, acyl, and ($C_1$-$C_6$)alkyl-O—C(O)—, where said moiety is optionally substituted with 1-3 fluorines, or $R^{4d''}$ is a heteroaryl, where said heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl;

a pharmaceutically acceptable salt thereof.

7. The compound of claim 4, 5 or 6 wherein $R^1$ and $R^2$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof.

8. The compound of claim 7 wherein $R^1$ and $R^2$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl, and cyano;

a pharmaceutically acceptable salt thereof.

9. The compound of claim 8 wherein $R^1$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^2$ is 4-chlorophenyl or 4-fluorophenyl;

a pharmaceutically acceptable salt thereof.

10. The compound of claim 9 selected from the group consisting of 7-(2-chlorophenyl)-8-(4-chlorophenyl)-2-methyl-4-(4-methylpiperazin-1-yl)-pyrazolo[1,5-a][1,3,5]triazine;

7-(2-chlorophenyl)-8-(4-chlorophenyl)-2-methyl-4-(4-pyrimidin-2-ylpiperazin-1-yl)-pyrazolo[1,5-a][1,3,5]triazine;

7-(2-chlorophenyl)-8-(4-chlorophenyl)-4-[(1S,4S)-5-methanesulfonyl-2,5-diazabicyclo[2.2.1]hept-2-yl]-2-methylpyrazolo[1,5-a][1,3,5]triazine;

7-(2-chlorophenyl)-8-(4-chlorophenyl)-2-methyl-4-[4-(propane-2-sulfonyl)-piperazin-1-yl]-pyrazolo[1,5-a][1,3,5]triazine;

7-(2-chlorophenyl)-8-(4-chlorophenyl)-2-methyl-4-(4-ethanesulfonyl)piperazin-1-yl)-pyrazolo[1,5-a][1,3,5]triazine;

7-(2-chlorophenyl)-8-(4-chlorophenyl)-2-methyl-4-piperazin-1-yl-pyrazolo[1,5-a][1,3,5]triazine;

7-(2-chlorophenyl)-8-(4-chlorophenyl)-2-methyl-4-(4-methanesulfonyl)-piperazin-1-yl)-pyrazolo[1,5-a][1,3,5]triazine;

(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]heptane-2-carboxylic acid tert-butyl ester;

7-(2-chlorophenyl)-8-(4-chlorophenyl)-4-[(1S,4S)-2,5-diazabicyclo[2.2.1]hept-2-yl]-2-methylpyrazolo[1,5-a][1,3,5]triazine;

1-{(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]hept-2-yl}-ethanone;

1-{(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]hept-2-yl}-2-methylpropan-1-one;

1-{(1S,4S)-5-[7-(2-chlorophenyl)-8-(4-chlorophenyl)-2-methylpyrazolo[1,5-a][1,3,5]triazin-4-yl]-2,5-diazabicyclo[2.2.1]hept-2-yl}-phenylmethanone;

7-(2-chlorophenyl)-8-(4-chlorophenyl)-4-[(1S,4S)-5-ethanesulfonyl-2,5-diazabicyclo[2.2.1]hept-2-yl]-2-methylpyrazolo[1,5-a][1,3,5]triazine;

7-(2-chlorophenyl)-8-(4-chlorophenyl)-2-methyl-4-[(1S,4S)-5-(propane-2-sulfonyl)-2,5-diazabicyclo[2.2.1]hept-2-yl]-pyrazolo[1,5-a][1,3,5]triazine; and (1S,4S)-5-[7-(2-chlorophenyl)-8-(4-chlorophenyl)-2-methylpyrazolo[1,5-a][1,3,5]triazin-4-yl]-2,5-diazabicyclo[2.2.1]heptane-2-sulfonic acid dimethylamide;

a pharmaceutically acceptable salt thereof.

11. The compound of claim 3 wherein Y is $—C(R^{4d})(R^{4d'})—$, where $R^{4d}$ is hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, $R^{4d'}$ is hydrogen, $H_2NC(O)—$, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated heterocyclic ring, a 5-6 membered lactone ring, or a 4-6 membered lactam ring, where said heterocyclic ring, said lactone ring and said lactam ring are optionally substituted with one or more substituents and said lactone ring and said lactam ring optionally contain an additional heteroatom selected from oxygen, nitrogen or sulfur;

a pharmaceutically acceptable salt thereof.

12. The compound of claim 11 wherein $R^{4b}$, $R^{4b'}$, $R^{4f}$, and $R^{4f'}$ are all hydrogen;

$R^{4d}$ is amino, $(C_1-C_6)$alkylamino, di$(C_1-C_4)$alkylamino, $(C_3-C_6)$cycloalkylamino, acylamino, aryl$(C_1-C_4)$alkylamino-, heteroaryl$(C_1-C_4)$alkylamino-; and $R^{4d'}$ is $(C_1-C_6)$alkyl, $H_2NC(O)—$, $(C_1-C_4)$alkyl-NH—C(O)—, or $((C_1-C_4)$alkyl)$_2$N—C(O)—, or aryl;

a pharmaceutically acceptable salt thereof.

13. The compound of claim 12 wherein

X is a bond or $—C(R^{4c})(R^{4c'})—$, where $R^{4c}$ and $R^{4c'}$ are each hydrogen; and Z is a bond or $—C(R^{4e})(R^{4e'})—$, where $R^{4e}$ and $R^{4e'}$ are each hydrogen;

a pharmaceutically acceptable salt thereof.

14. The compound of claim 13 wherein $R^{4d}$ is amino, $(C_1-C_6)$alkylamino, di$(C_1-C_4)$alkylamino, $(C_3-C_6)$cycloalkylamino; and $R^{4d'}$ is $H_2NC(O)—$, $(C_1-C_4)$alkyl-NH—C(O)—, or $((C_1-C_4)$alkyl)$_2$N—C(O)—;

a pharmaceutically acceptable salt thereof.

15. The compound of claim 11, 12, 13 or 14 wherein $R^1$ and $R^2$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof.

16. The compound of claim 15 wherein $R^1$ and $R^2$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof.

17. The compound of claim 16 selected from the group consisting of

1-[7-(2-chlorophenyl)-8-(2,4-dichlorophenyl)-2-methylpyrazolo[1,5-a][1,3,5]triazin-4-yl]-3-ethylaminoazetidine-3-carboxylic acid amide;

1-[7,8-bis-(2-chlorophenyl)-2-methylpyrazolo[1,5-a][1,3,5]triazin-4-yl]-3-ethylaminoazetidine-3-carboxylic acid amide;

1-[7-(2-chlorophenyl)-8-(4-cyanophenyl)-2-methylpyrazolo[1,5-a][1,3,5]triazin-4-yl]-3-ethylaminoazetidine-3-carboxylic acid amide;

1-[7-(2-chlorophenyl)-8-(4-methylphenyl)-2-methylpyrazolo[1,5-a][1,3,5]triazin-4-yl]-3-ethylaminoazetidine-3-carboxylic acid amide;

1-[7-(2-chlorophenyl)-8-(4-ethylphenyl)-2-methylpyrazolo[1,5-a][1,3,5]triazin-4-yl]-3-ethylaminoazetidine-3-carboxylic acid amide; and 1-[7-(2-chlorophenyl)-8-(4-methoxyphenyl)-2-methylpyrazolo[1,5-a][1,3,5]triazin-4-yl]-3-ethylaminoazetidine-3-carboxylic acid amide;

a pharmaceutically acceptable salt thereof.

18. The compound of claim 16 wherein $R^1$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^2$ is 4-chlorophenyl or 4-fluorophenyl;

a pharmaceutically acceptable salt thereof.

19. The compound of claim 18 selected from the group consisting of

1-[7-(2-chlorophenyl)-8-(4-chlorophenyl)-2-methylpyrazolo[1,5-a][1,3,5]triazin-4-yl]-4-methylaminopiperidine-4-carboxylic acid amide;

1-[7-(2-chlorophenyl)-8-(4-fluorophenyl)-2-methylpyrazolo[1,5-a][1,3,5]triazin-4-yl]-4-ethylaminopiperidine-4-carboxylic acid amide;

1-[7-(2-chlorophenyl)-8-(4-chlorophenyl)-2-methylpyrazolo[1,5-a][1,3,5]triazin-4-yl]4-ethylaminopiperidine-4-carboxylic acid amide;

1-[7-(2-chlorophenyl)-8-(4-chlorophenyl)-2-methylpyrazolo[1,5-a][1,3,5]triazin-4-yl]-4-isopropylaminopiperidine-4-carboxylic acid amide;

1-[7-(2-chlorophenyl)-8-(4-chlorophenyl)-2-methylpyrazolo[1,5-a][1,3,5]triazin-4-yl]-3-ethylaminoazetidine-3-carboxylic acid amide;

1-[7-(2-chlorophenyl)-8-(4-chlorophenyl)-2-methylpyrazolo[1,5-a][1,3,5]triazin-4-yl]-3-isopropylaminoazetidine-3-carboxylic acid amide;

3-amino-1-[7-(2-chlorophenyl)-8-(4-chlorophenyl)-2-methylpyrazolo[1,5-a][1,3,5]triazin-4-yl]-azetidine-3-carboxylic acid amide;

1-[7-(2-chlorophenyl)-8-(4-chlorophenyl)-2-methylpyrazolo[1,5-a][1,3,5]triazin-4-yl]-3-methylaminoazetidine-3-carboxylic acid amide;

1-[7-(2-chlorophenyl)-8-(4-chlorophenyl)-2-methylpyrazolo[1,5-a][1,3,5]triazin-4-yl]-3-dimethylaminoazetidine-3-carboxylic acid amide;

1-[7-(2-chlorophenyl)-8-(4-chlorophenyl)-pyrazolo[1,5-a][1,3,5]triazin-4-yl]-3-isopropylaminoazetidine-3-carboxylic acid amide;

1-[7-(2-chlorophenyl)-8-(4-chlorophenyl)-pyrazolo[1,5-a][1,3,5]triazin-4-yl]-4-ethylaminopiperidine-4-carboxylic acid amide;

1-[7-(2-chlorophenyl)-8-(4-chlorophenyl)-pyrazolo[1,5-a][1,3,5]triazin-4-yl]-3-ethylaminoazetidine-3-carboxylic acid amide; and 1-[7-(2-chlorophenyl)-8-(4-chlorophenyl)-pyrazolo[1,5-a][1,3,5]triazin-4-yl]-3-methylaminoazetidine-3-carboxylic acid amide;

a pharmaceutically acceptable salt thereof.

20. The compound of claim 19 selected from the group consisting of

1-[7-(2-chlorophenyl)-8-(4-chlorophenyl)-2-methylpyrazolo[1,5-a][1,3,5]triazin-4-yl]-4-ethylaminopiperidine-4-carboxylic acid amide;

1-[7-(2-chlorophenyl)-8-(4-chlorophenyl)-2-methylpyrazolo[1,5-a][1,3,5]triazin-4-yl]-3-ethylaminoazetidine-3-carboxylic acid amide;

1-[7-(2-chlorophenyl)-8-(4-chlorophenyl)-2-methylpyrazolo[1,5-a][1,3,5]triazin-4-yl]-3-isopropylaminoazetidine-3-carboxylic acid amide;

3-amino-1-[7-(2-chlorophenyl)-8-(4-chlorophenyl)-2-methylpyrazolo[1,5-a][1,3,5]triazin-4-yl]-azetidine-3-carboxylic acid amide;

1-[7-(2-chlorophenyl)-8-(4-chlorophenyl)-2-methylpyrazolo[1,5-a][1,3,5]triazin-4-yl]-3-methylaminoazetidine-3-carboxylic acid amide;

1-[7-(2-chlorophenyl)-8-(4-chlorophenyl)-pyrazolo[1,5-a][1,3,5]triazin-4-yl]-3-isopropylaminoazetidine-3-carboxylic acid amide;

1-[7-(2-chlorophenyl)-8-(4-chlorophenyl)-pyrazolo[1,5-a][1,3,5]triazin-4-yl]-4-ethylaminopiperidine-4-carboxylic acid amide; and 1-[7-(2-chlorophenyl)-8-(4-chlorophenyl)-pyrazolo[1,5-a][1,3,5]triazin-4-yl]-3-ethylaminoazetidine-3-carboxylic acid amide;

a pharmaceutically acceptable salt thereof.

21. The compound of claim 11 wherein $R^{4b}$, $R^{4b'}$, $R^{4f}$, and $R^{4f'}$ are all hydrogen;

$R^{4d}$ is hydrogen, hydroxy, amino, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_6)$alkylamino-, and di$(C_1-C_4)$alkylamino-, where said moiety is optionally substituted with one or more substituents; and $R^{4d'}$ is hydrogen, or a chemical moiety selected from the group consisting of $(C_1-C_6)$alkyl, aryl and heteroaryl, where said moiety is optionally substituted with one or more substituents;

a pharmaceutically acceptable salt thereof.

22. The compound of claim 21 wherein

X is a bond or —C($R^{4c}$)($R^{4c'}$)—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and Z is a bond or —C($R^{4e}$)($R^{4e'}$)—, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;

a pharmaceutically acceptable salt thereof.

23. The compound of claim 22 wherein $R^{4c}$ and $R^{4c'}$ are each hydrogen or either $R^{4c}$ or $R^{4c'}$ taken together with $R^{4e}$ or $R^{4e'}$ forms a bond;

$R^{4d}$ is hydrogen, hydroxy, amino, or a chemical moiety selected from the group consisting of $(C_1-C_6)$alkoxy, acyl, $(C_1-C_6)$alkylamino-, and di$(C_1-C_4)$alkylamino-;

$R^{4d'}$ is hydrogen, or a chemical moiety selected from the group consisting of $(C_1-C_6)$alkyl and aryl, where said moiety is optionally substituted with one or more substituents; and $R^{4e}$ and $R^{4e'}$ are hydrogen or either $R^{4e}$ or $R^{4e'}$ taken together with $R^{4c}$ or $R^{4c'}$ forms a bond;

a pharmaceutically acceptable salt thereof.

24. The compound of claim 21, 22, or 23 wherein $R^1$ and $R^2$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof.

25. The compound of claim 24 wherein $R^1$ and $R^2$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof.

26. The compound of claim 25 wherein $R^1$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^2$ is 4-chlorophenyl or 4-fluorophenyl;

a pharmaceutically acceptable salt thereof.

27. The compound of claim 26 selected from the group consisting of
1-{1-[7-(2-chlorophenyl)-8-(4-chlorophenyl)-2-methylpyrazolo[1,5-a][1,3,5]triazin-4-yl]-4-phenylpiperidin-4-yl}-ethanone;
3-[7-(2-chlorophenyl)-8-(4-chlorophenyl)-2-methylpyrazolo[1,5-a][1,3,5]triazin-4-yl]-3-azabicyclo[3.1.0]hex-6-ylamine;
1-[7-(2-chlorophenyl)-8-(4-chlorophenyl)-2-methylpyrazolo[1,5-a][1,3,5]triazin-4-yl]-4-(4-fluorophenyl)-piperidin-4-ol; and
4-benzyl-1-[7-(2-chlorophenyl)-8-(4-chlorophenyl)-2-methylpyrazolo[1,5-a][1,3,5]triazin-4-yl]-piperidin-4-ol;

a pharmaceutically acceptable salt thereof.

28. The compound of claim 11 wherein
$R^{4b}$, $R^{4b'}$, $R^{4f}$, and $R^{4f'}$ are all hydrogen; and
$R^{4d}$ and $R^{4d'}$ taken together form a 3-6 membered partially or fully saturated heterocyclic ring, a 5-6 membered lactone ring, or a 4-6 membered lactam ring, where said heterocyclic ring, said lactone ring and said lactam ring are optionally substituted with one or more substituents and said lactone ring or said lactam ring optionally contains an additional heteroatom selected from oxygen, nitrogen or sulfur;

a pharmaceutically acceptable salt thereof.

29. The compound of claim 28 wherein
X is a bond, —CH$_2$CH$_2$— or —C($R^{4c}$)($R^{4c'}$)—, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and
Z is a bond, —CH$_2$CH$_2$— or —C($R^{4e}$)($R^{4e'}$)—, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;

a pharmaceutically acceptable salt thereof.

30. The compound of claim 28 wherein $R^{4d}$ and $R^{4d'}$ taken together form a 5-6 membered lactam ring, where said lactam ring is optionally substituted with one or more substituents and optionally contains an additional heteroatom selected from nitrogen or oxygen;

a pharmaceutically acceptable salt thereof.

31. The compound of claim 30 wherein
X is a bond or —C($R^{4c}$)($R^{4c'}$)—, where $R^{4c}$ and $R^{4c'}$ are each hydrogen; and Z is a bond or —C($R^{4e}$)($R^{4e'}$)—, where $R^{4e}$ and $R^{4e'}$ are each hydrogen;

a pharmaceutically acceptable salt thereof.

32. The compound of claim 28, 29, 30 or 31 wherein $R^1$ and $R^2$ are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof.

33. The compound of claim 32 wherein $R^1$ and $R^2$ are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof.

34. The compound of claim 33 wherein $R^1$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^2$ is 4-chlorophenyl or 4-fluorophenyl;

a pharmaceutically acceptable salt thereof.

35. The compound of claim 34 selected from the group consisting of
2-[7-(2-chlorophenyl)-8-(4-chlorophenyl)-2-methylpyrazolo[1,5-a][1,3,5]triazin-4-yl]-5-methyl-2,5,7-triazaspiro[3.4]octan-8-one;
2-[7-(2-chlorophenyl)-8-(4-chlorophenyl)-2-methylpyrazolo[1,5-a][1,3,5]triazin-4-yl]-2,5,7-triazaspiro[3.4]octan-8-one;
8-[7-(2-chlorophenyl)-8-(4-chlorophenyl)-2-methylpyrazolo[1,5-a][1,3,5]triazin-4-yl]-1-isopropyl-1,3,8-triazaspiro[4.5]decan-4-one; and
2-[7-(2-chlorophenyl)-8-(4-chlorophenyl)-2-methylpyrazolo[1,5-a][1,3,5]triazin-4-yl]-6,6-dimethyl-2,5,7-triazaspiro[3.4]octan-8-one;

a pharmaceutically acceptable salt thereof.

36. The compound of claim 35 which is
8-[7-(2-chlorophenyl)-8-(4-chlorophenyl)-2-methylpyrazolo[1,5-a][1,3,5]triazin-4-yl]-1-isopropyl-1,3,8-triazaspiro[4.5]decan-4-one;

a pharmaceutically acceptable salt thereof.

37. A compound of Formula (II)

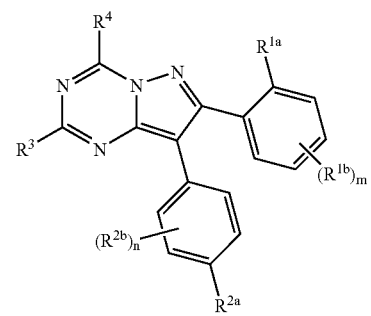

(II)

wherein
$R^{1a}$, $R^{1b}$, $R^{2a}$, and $R^{2b}$ are each independently halo, $(C_1-C_4)$alkoxy, $(C_1-C_4)$alkyl, halo-substituted $(C_1-C_4)$alkyl, or cyano;
n and m are each independently 0, 1 or 2;
$R^3$ is hydrogen, $(C_1-C_4)$alkyl, halo-substituted $(C_1-C_4)$alkyl, or $(C_1-C_4)$alkoxy; and $R^4$ is
(i) a group having Formula (IA)

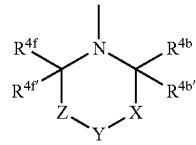

where $R^{4a}$ is hydrogen or $(C_1\text{-}C_3)$alkyl;

$R^{4b}$ and $R^{4b'}$ are each independently hydrogen, cyano, hydroxy, amino, $H_2NC(O)$—, or a chemical moiety selected from the group consisting of $(C_1\text{-}C_6)$alkyl, $(C_1\text{-}C_6)$alkoxy, acyloxy, acyl, $(C_1\text{-}C_3)$alkyl-O—C(O)—, $(C_1\text{-}C_4)$alkyl-NH—C(O)—, $((C_1\text{-}C_4)\text{alkyl})_2$N—C(O)—, $(C_1\text{-}C_6)$alkylamino-, $((C_1\text{-}C_4)\text{alkyl})_2$amino-, $(C_3\text{-}C_6)$cycloalkylamino-, acylamino-, aryl$(C_1\text{-}C_4)$alkylamino-, heteroaryl$(C_1\text{-}C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —CH$_2$CH$_2$— or —C(R$^{4c}$)(R$^{4c'}$)—, where $R^{4c}$ and $R^{4c'}$ are each independently hydrogen, cyano, hydroxy, amino, $H_2NC(O)$—, or a chemical moiety selected from the group consisting of $(C_1\text{-}C_6)$alkyl, $(C_1\text{-}C_6)$alkoxy, acyloxy, acyl, $(C_1\text{-}C_3)$alkyl-O—C(O)—, $(C_1\text{-}C_4)$alkyl-NH—C(O)—, $((C_1\text{-}C_4)\text{alkyl})_2$N—C(O)—, $(C_1\text{-}C_6)$alkylamino-, di$(C_1\text{-}C_4)$alkylamino-, $(C_3\text{-}C_6)$cycloalkylamino-, acylamino-, aryl$(C_1\text{-}C_4)$alkylamino-, heteroaryl$(C_1\text{-}C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —C(R$^{4d}$)(R$^{4d'}$)—, where $R^{4d}$ and $R^{4d'}$ are each independently hydrogen, cyano, hydroxy, amino, $H_2NC(O)$—, or a chemical moiety selected from the group consisting of $(C_1\text{-}C_6)$alkyl, $(C_1\text{-}C_6)$alkoxy, acyloxy, acyl, $(C_1\text{-}C_3)$alkyl-O—C(O)—, $(C_1\text{-}C_4)$alkyl-NH—C(O)—, $((C_1\text{-}C_4)\text{alkyl})_2$N—C(O)—, $(C_1\text{-}C_6)$alkylamino-, di$(C_1\text{-}C_4)$alkylamino-, $(C_3\text{-}C_6)$cycloalkylamino-, acylamino-, aryl$(C_1\text{-}C_4)$alkylamino-, heteroaryl$(C_1\text{-}C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where the carbocyclic ring, the heterocyclic ring, the lactone ring and the lactam ring are optionally substituted with one or more substituents and the lactone ring and the lactam ring optionally contain an additional heteroatom selected from oxygen, nitrogen or sulfur, or Y is —NR$^{4d''}$—, where R$^{4d''}$ is a hydrogen or a chemical moiety selected from the group consisting of $(C_1\text{-}C_6)$alkyl, $(C_3\text{-}C_6)$cycloalkyl, $(C_1\text{-}C_3)$alkylsulfonyl-, $(C_1\text{-}C_3)$alkylaminosulfonyl-, di$(C_1\text{-}C_3)$alkylaminosulfonyl-, acyl, $(C_1\text{-}C_6)$alkyl-O—C(O)—, aryl, and heteroaryl, where said moiety is optionally substituted with one or more substituents;

Z is a bond, —CH$_2$CH$_2$—, or —C(R$^{4e}$)(R$^{4e'}$)—, where $R^{4e}$ and $R^{4e'}$ are each independently hydrogen, cyano, hydroxy, amino, $H_2NC(O)$—, or a chemical moiety selected from the group consisting of $(C_1\text{-}C_6)$alkyl, $(C_1\text{-}C_6)$alkoxy, acyloxy, acyl, $(C_1\text{-}C_3)$alkyl-O—C(O)—, $(C_1\text{-}C_4)$alkyl-NH—C(O)—, $((C_1\text{-}C_4)\text{alkyl})_2$N—C(O)—, $(C_1\text{-}C_6)$alkylamino-, di$(C_1\text{-}C_4)$alkylamino-, $(C_3\text{-}C_6)$cycloalkylamino-, acylamino-, aryl$(C_1\text{-}C_4)$alkylamino-, heteroaryl$(C_1\text{-}C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1\text{-}C_6)$alkyl, $(C_1\text{-}C_6)$alkoxy, acyloxy, acyl, $(C_1\text{-}C_3)$alkyl-O—C(O)—, $(C_1\text{-}C_4)$alkyl-NH—C(O)—, $((C_1\text{-}C_4)\text{alkyl})_2$N—C(O)—, $(C_1\text{-}C_6)$alkylamino-, di$(C_1\text{-}C_4)$alkylamino-, $(C_3\text{-}C_6)$cycloalkylamino-, acylamino-, aryl$(C_1\text{-}C_4)$alkylamino-, heteroaryl$(C_1\text{-}C_4)$alkylamino-, aryl, heteroaryl, a 3-6 membered partially or fully saturated heterocycle, and a 3-6 membered partially or fully saturated carbocyclic ring, where said moiety is optionally substituted with one or more substituents, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

a pharmaceutically acceptable salt thereof.

38. The compound of claim of 37 wherein
$R^{4b}$ is hydrogen, an optionally substituted $(C_1\text{-}C_3)$alkyl, or taken together with $R^{4e}$, $R^{4e'}$, $R^{4f}$, or $R^{4f'}$ forms a bond, a methylene bridge, or an ethylene bridge;
$R^{4b'}$ is hydrogen, an optionally substituted $(C_1\text{-}C_3)$alkyl, or taken together with $R^{4e}$, $R^{4e'}$, $R^{4f}$, or $R^{4f'}$ forms a bond, a methylene bridge, or an ethylene bridge;
$R^{4f}$ is hydrogen, an optionally substituted $(C_1\text{-}C_3)$alkyl, or taken together with $R^{4b}$, $R^{4b'}$, $R^{4c}$, or $R^{4c'}$ forms a bond, a methylene bridge, or an ethylene bridge; and
$R^{4f'}$ is hydrogen, an optionally substituted $(C_1\text{-}C_3)$alkyl, or taken together with $R^{4b}$, $R^{4b'}$, $R^{4c}$, or $R^{4c'}$ forms a bond, a methylene bridge, or an ethylene bridge;
a pharmaceutically acceptable salt thereof.

39. The compound of claim 38 wherein
X is —C(R$^{4c}$)(R$^{4c'}$)—, where $R^{4c}$ and $R^{4c'}$ are each independently hydrogen, $H_2NC(O)$—, or a chemical moiety selected from $(C_1\text{-}C_6)$alkyl, $(C_1\text{-}C_4)$alkyl-NH—C(O)—, or $((C_1\text{-}C_4)\text{alkyl})_2$N—C(O)—, where said moiety is optionally substituted with one or more substituents, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is —$NR^{4d''}$—, $R^{4d''}$ is a hydrogen or a chemical moiety selected from the group consisting of $(C_1$-$C_6)$alkyl, $(C_3$-$C_6)$cycloalkyl, $(C_1$-$C_3)$alkylsulfonyl, $(C_1$-$C_3)$alkylaminosulfonyl, di$(C_1$-$C_3)$alkylaminosulfonyl, acyl, $(C_1$-$C_6)$alkyl-O—C(O)—, aryl, and heteroaryl, where said moiety is optionally substituted with one or more substituents;

Z is —C($R^{4e}$)($R^{4e'}$)—, where $R^{4e}$ and $R^{4e'}$ are each independently hydrogen, $H_2NC(O)$—, or a chemical moiety selected from $(C_1$-$C_6)$alkyl, $(C_1$-$C_4)$alkyl-NH—C(O)—, or (($C_1$-$C_4)$alkyl)$_2$N—C(O)—, where said moiety is optionally substituted with one or more substituents, or either $R^{4e}$ or $R^{4e'}$ taken together with $R^{4b}$, $R^{4b'}$, $R^{4c}$, or $R^{4c'}$ forms a bond, a methylene bridge or an ethylene bridge;

a pharmaceutically acceptable salt thereof.

40. The compound of claim 39 wherein $R^{4d''}$ is a hydrogen or a chemical moiety selected from the group consisting of $(C_1$-$C_3)$alkylsulfonyl, $(C_1$-$C_3)$alkylaminosulfonyl, di($C_1$-$C_3)$alkylaminosulfonyl, acyl, $(C_1$-$C_6)$alkyl-O—C(O)—, and heteroaryl, where said moiety is optionally substituted with one or more substituents;

a pharmaceutically acceptable salt thereof.

41. The compound of claim 40 wherein $R^{4d''}$ is a hydrogen or a chemical moiety selected from the group consisting of $(C_1$-$C_3)$alkylsulfonyl, $(C_1$-$C_3)$alkylaminosulfonyl, di($C_1$-$C_3)$alkylaminosulfonyl, acyl, and $(C_1$-$C_6)$alkyl-O—C(O)—, where said moiety is optionally substituted with 1-3 fluorines, or $R^{4d''}$ is a heteroaryl, where said heteroaryl is optionally substituted with 1 to 2 substituents independently selected from the group consisting of chloro, fluoro, $(C_1$-$C_3)$alkoxy, $(C_1$-$C_3)$alkyl, and fluoro-substituted $(C_1$-$C_3)$alkyl;

a pharmaceutically acceptable salt thereof.

42. The compound of claim 39, 40, or 41 wherein $R^{1a}$, $R^{1b}$, $R^{2a}$ and $R^{2b}$ are each independently selected from the group consisting of halo, $(C_1$-$C_4)$alkoxy, $(C_1$-$C_4)$alkyl, halo-substituted $(C_1$-$C_4)$alkyl, and cyano;

a pharmaceutically acceptable salt thereof.

43. The compound of claim 42 wherein $R^{1a}$, $R^{1b}$, $R^{2a}$ and $R^{2b}$ are each independently selected from the group consisting of chloro, fluoro, $(C_1$-$C_4)$alkoxy, $(C_1$-$C_4)$alkyl, fluoro-substituted $(C_1$-$C_4)$alkyl), and cyano; and n and m are each independently 0 or 1;

a pharmaceutically acceptable salt thereof.

44. The compound of claim 38 wherein Y is —C($R^{4d}$)($R^{4d'}$)—, where $R^{4d}$ is hydrogen, cyano, hydroxy, amino, $H_2NC(O)$—, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_4)$alkyl-NH—C(O)—, (($C_1$-$C_4)$alkyl)$_2$N—C(O)—, $(C_1$-$C_6)$alkylamino-, (($C_1$-$C_4)$alkyl)$_2$amino-, $(C_3$-$C_6)$cycloalkylamino-, acylamino-, aryl($C_1$-$C_4$)alkylamino-, heteroaryl($C_1$-$C_4$)alkylamino-, aryl, heteroaryl, a 3-6 membered partially or fully saturated heterocycle, and a partially or fully saturated carbocyclic ring, where said moiety is optionally substituted with one or more substituents, $R^{4d'}$ is hydrogen, $H_2NC(O)$—, or a chemical moiety selected from the group consisting of $(C_1$-$C_6)$alkyl, acyl, $(C_1$-$C_3)$alkyl-O—C(O)—, $(C_1$-$C_4)$alkyl-NH—C(O)—, (($C_1$-$C_4)$alkyl)$_2$N—C(O)—, aryl, heteroaryl, a 3-6 membered partially or fully saturated heterocycle, and a partially or fully saturated carbocyclic ring, where said moiety is optionally substituted with one or more substituents, or $R^{4d}$ and $R^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring and said lactam ring optionally contain an additional heteroatom selected from oxygen, nitrogen or sulfur;

a pharmaceutically acceptable salt thereof.

45. The compound of claim 44 wherein $R^{4b}$, $R^{4b'}$, $R^{4f}$, and $R^{4f'}$ are all hydrogen;

$R^{4d}$ is amino, $(C_1$-$C_6)$alkylamino, di($C_1$-$C_4)$alkylamino, $(C_3$-$C_6)$cycloalkylamino, acylamino, aryl($C_1$-$C_4$)alkylamino-, heteroaryl($C_1$-$C_4$)alkylamino-; and $R^{4d'}$ is $(C_1$-$C_6)$alkyl, $H_2NC(O)$—, $(C_1$-$C_4)$alkyl-NH—C(O)—, or (($C_1$-$C_4)$alkyl)$_2$N—C(O)—, or aryl;

a pharmaceutically acceptable salt thereof.

46. The compound of claim 45 wherein

X is a bond or —C($R^{4c}$)($R^{4c'}$)—, where $R^{4c}$ and $R^{4c'}$ are each hydrogen; and Z is a bond or —C($R^{4e}$)($R^{4e'}$)—, where $R^{4e}$ and $R^{4e'}$ are each hydrogen;

a pharmaceutically acceptable salt thereof.

47. The compound of claim 46 wherein $R^{4d}$ is amino, $(C_1$-$C_6)$alkylamino, di($C_1$-$C_4)$alkylamino, $(C_3$-$C_6)$cycloalkylamino; and $R^{4d'}$ is $H_2NC(O)$—, $(C_1$-$C_4)$alkyl-NH—C(O)—, or (($C_1$-$C_4)$alkyl)$_2$N—C(O)—;

a pharmaceutically acceptable salt thereof.

48. The compound of claim 44, 45, 46 or 47 wherein $R^{1a}$, $R^{1b}$, $R^{2a}$, and $R^{2b}$ are each independently selected from the group consisting of halo, $(C_1$-$C_4)$alkoxy, $(C_1$-$C_4)$alkyl, halo-substituted $(C_1$-$C_4)$alkyl, and cyano;

a pharmaceutically acceptable salt thereof.

49. The compound of claim 48 wherein $R^{1a}$, $R^{1b}$, $R^{2a}$, and $R^{2b}$ are each independently selected from the group consisting of chloro, fluoro, $(C_1$-$C_4)$alkoxy, $(C_1$-$C_4)$alkyl, fluoro-substituted $(C_1$-$C_4)$alkyl), and cyano; and n and m are each independently selected from 0 or 1;

a pharmaceutically acceptable salt thereof.

50. The compound of claim 44 wherein $R^{4b}$, $R^{4b'}$, $R^{4f}$, and $R^{4f'}$ are all hydrogen;

$R^{4d}$ is hydrogen, hydroxy, amino, or a chemical moiety selected from the group consisting of $(C_1$-$C_6)$alkyl, $(C_1$-$C_6)$alkoxy, acyloxy, acyl, $(C_1$-$C_3)$alkyl-O—C(O)—, $(C_1$-$C_6)$alkylamino-, and di($C_1$-$C_4)$alkylamino-, where said moiety is optionally substituted with one or more substituents; and $R^{4d'}$ is hydrogen, or a chemical moiety selected from the group consisting of $(C_1$-$C_6)$alkyl, aryl and heteroaryl, where said moiety is optionally substituted with one or more substituents;

a pharmaceutically acceptable salt thereof.

51. The compound of claim 50 wherein

X is a bond or —C($R^{4c}$)($R^{4c'}$)—, where $R^{4c}$ and $R^{4c'}$ are each independently hydrogen or an optionally substituted $(C_1$-$C_6)$alkyl, or either $R^{4c}$ or $R^{4c'}$ taken together with $R^{4e}$ or $R^{4e'}$ forms a bond, a methylene bridge or an ethylene bridge; and Z is a bond or —C($R^{4e}$)($R^{4e'}$)—, where $R^{4e}$ and $R^{4e'}$ are each independently hydrogen or an optionally substituted (C$_1$-C$_6$)alkyl, or either R$^{4e}$ or R$^{4e'}$ taken together with R$^{4c}$ or R$^{4c'}$ forms a bond, a methylene bridge or an ethylene bridge;

a pharmaceutically acceptable salt thereof.

52. The compound of claim 51 wherein

R$^{4c}$ and R$^{4c'}$ are each hydrogen or either R$^{4c}$ or R$^{4c'}$ taken together with R$^{4e}$ or R$^{4e'}$ forms a bond;

R$^{4d}$ is hydrogen, hydroxy, amino, or a chemical moiety selected from the group consisting of (C$_1$-C$_6$)alkoxy, acyl, (C$_1$-C$_6$)alkylamino-, and di(C$_1$-C$_4$)alkylamino-;

R$^{4d'}$ is hydrogen, or a chemical moiety selected from the group consisting of (C$_1$-C$_6$)alkyl and aryl, where said moiety is optionally substituted with one or more substituents; and R$^{4e}$ and R$^{4e'}$ are hydrogen or either R$^{4e}$ or R$^{4e'}$ taken together with R$^{4c}$ or R$^{4c'}$ forms a bond;

a pharmaceutically acceptable salt thereof.

53. The compound of claim 50, 51, or 52 wherein R$^{1a}$, R$^{1b}$, R$^{2a}$, and R$^{2b}$ are each independently selected from the group consisting of halo, (C$_1$-C$_4$)alkoxy, (C$_1$-C$_4$)alkyl, halo-substituted (C$_1$-C$_4$)alkyl, and cyano;

a pharmaceutically acceptable salt thereof.

54. The compound of claim 53 wherein R$^{1a}$, R$^{1b}$, R$^{2a}$, and R$^{2b}$ are each independently selected from the group consisting of chloro, fluoro, (C$_1$-C$_4$)alkoxy, (C$_1$-C$_4$)alkyl, fluoro-substituted (C$_1$-C$_4$)alkyl), and cyano; and n and m are each independently 0 or 1;

a pharmaceutically acceptable salt thereof.

55. The compound of claim 54 wherein

R$^{4b}$, R$^{4b'}$, R$^{4f}$, and R$^{4f'}$ are all hydrogen; and

R$^{4d}$ and R$^{4d'}$ taken together form a 3-6 membered partially or fully saturated carbocyclic ring, a 3-6 membered partially or fully saturated heterocyclic ring, a 5-6 membered lactone ring, or a 4-6 membered lactam ring, where said carbocyclic ring, said heterocyclic ring, said lactone ring and said lactam ring are optionally substituted with one or more substituents and said lactone ring or said lactam ring optionally contains an additional heteroatom selected from oxygen, nitrogen or sulfur;

a pharmaceutically acceptable salt thereof.

56. The compound of claim 55 wherein

X is a bond, —CH$_2$CH$_2$— or —C(R$^{4c}$)(R$^{4c'}$)—, where R$^{4c}$ and R$^{4c'}$ are each independently hydrogen or an optionally substituted (C$_1$-C$_6$)alkyl, or either R$^{4c}$ or R$^{4c'}$ taken together with R$^{4e}$ or R$^{4e'}$ forms a bond, a methylene bridge or an ethylene bridge; and Z is a bond, —CH$_2$CH$_2$— or —C(R$^{4e}$)(R$^{4e'}$)—, where R$^{4'}$ and R$^{4e'}$ are each independently hydrogen or an optionally substituted (C$_1$-C$_6$)alkyl, or either R$^{4e}$ or R$^{4e'}$ taken together with R$^{4c}$ or R$^{4c'}$ forms a bond, a methylene bridge or an ethylene bridge;

a pharmaceutically acceptable salt thereof.

57. The compound of claim 56 wherein R$^{4d}$ and R$^{4d'}$ taken together form a 5-6 membered lactam ring, where said lactam ring is optionally substituted with one or more substituents and optionally contains an additional heteroatom selected from nitrogen or oxygen;

a pharmaceutically acceptable salt thereof.

58. The compound of claim 57 wherein

X is a bond or —C(R$^{4c}$)(R$^{4c'}$)—, where R$^{4c}$ and R$^{4c'}$ are each hydrogen; and Z is a bond or —C(R$^{4e}$)(R$^{4e'}$)—, where R$^{4e}$ and R$^{4e'}$ are each hydrogen;

a pharmaceutically acceptable salt thereof.

59. The compound of claim 55, 56, 57 or 58 wherein R$^{1a}$, R$^{1b}$, R$^{2a}$, and R$^{2b}$ are each independently selected from the group consisting of halo, (C$_1$-C$_4$)alkoxy, (C$_1$-C$_4$)alkyl, halo-substituted (C$_1$-C$_4$)alkyl, and cyano;

a pharmaceutically acceptable salt thereof.

60. The compound of claim 59 wherein R$^{1a}$, R$^{1b}$, R$^{2a}$, and R$^{2b}$ are each independently selected from the group consisting of chloro, fluoro, (C$_1$-C$_4$)alkoxy, (C$_1$-C$_4$)alkyl, fluoro-substituted (C$_1$-C$_4$)alkyl), and cyano;

n and m are each independently 0 or 1;

a pharmaceutically acceptable salt thereof.

61. A pharmaceutical composition comprising (1) a compound of claim 1, a pharmaceutically acceptable salt thereof; and (2) a pharmaceutically acceptable excipient, diluent, or carrier.

62. A method for treating obesity in animals comprising the step of administering to an animal in need of such treatment a therapeutically effective amount of a compound of claim 1 a pharmaceutically acceptable salt thereof.

63. A method for treating obesity in animals comprising the step of administering to an animal in need of such treatment a therapeutically effective amount of a pharmaceutical composition of claim 61.

64. A compound having the structure

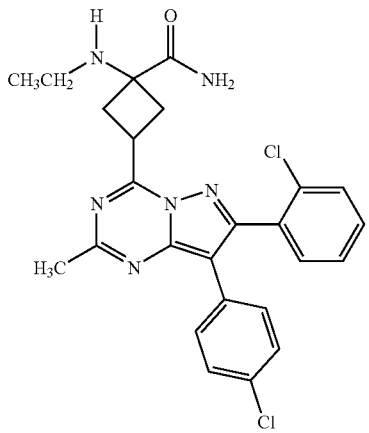

65. A compound which is 1-[7-(2-chlorophenyl)-8-(4-chlorophenyl)-2-methylpyrazolo[1,5-a][1,3,5]triazin-4-yl]-3-ethylaminoazetidine-3-carboxylic acid amide;

or a pharmaceutically acceptable salt thereof.

* * * * *